US008586814B2

(12) United States Patent
Fisher et al.

(10) Patent No.: US 8,586,814 B2
(45) Date of Patent: Nov. 19, 2013

(54) SQUALANE AND ISOSQUALANE COMPOSITIONS AND METHODS FOR PREPARING THE SAME

(75) Inventors: Karl Fisher, Petaluma, CA (US); Susan Jessica Schofer, San Francisco, CA (US); David B. Kanne, Corte Madera, CA (US)

(73) Assignee: Amyris, Inc., Emeryville, CA (US)

( * ) Notice: Subject to any disclaimer, the term of this patent is extended or adjusted under 35 U.S.C. 154(b) by 280 days.

(21) Appl. No.: 13/112,991

(22) Filed: May 20, 2011

(65) Prior Publication Data

US 2011/0287988 A1 Nov. 24, 2011

Related U.S. Application Data

(60) Provisional application No. 61/347,366, filed on May 21, 2010, provisional application No. 61/391,538, filed on Oct. 8, 2010, provisional application No. 61/447,689, filed on Feb. 28, 2011.

(51) Int. Cl.
*C10M 169/04* (2006.01)

(52) U.S. Cl.
USPC ......... 585/700; 585/310; 508/110; 106/130.1

(58) Field of Classification Search
USPC ................. 508/110; 585/310, 700; 106/130.1
See application file for complete search history.

(56) References Cited

U.S. PATENT DOCUMENTS

| 3,794,692 A | 2/1974 | Komatsu et al. |
| 3,843,742 A | 10/1974 | Yagi et al. |
| 3,859,374 A | 1/1975 | Komatsu et al. |
| 4,966,874 A | 10/1990 | Young et al. |
| 5,449,850 A | 9/1995 | Young et al. |
| 6,316,380 B1 | 11/2001 | Nolan et al. |
| 7,399,323 B2 | 7/2008 | Renninger et al. |
| 7,592,295 B1 | 9/2009 | Fisher et al. |
| 7,691,792 B1 | 4/2010 | Fisher et al. |

FOREIGN PATENT DOCUMENTS

| DE | 1 018 048 B | 10/1957 |
| EP | 0721053 | 7/1996 |
| WO | WO 2004/014550 A2 | 2/2004 |
| WO | WO 2010/042208 A2 | 4/2010 |

OTHER PUBLICATIONS

Akutagawa et al., "Metal-Assisted Terpenoid Sythesys II—Catalytic Conversion of Isoprene into Farnesene and its Isomer, 2,6-Dimethyl-10-Methylene-1,6-trans,11-Dodecatiene," Chemistry Letters, 1976, pp. 485-490.
Akutagawa et al., "Metal-Assisted Terpenoid Synthesis. V. The Catalytic Trimerization of Isoprene to trans-$\beta$-Farnesene and Its Synthetic Applications for Terpenoids," Bulletin of the Chemical Society of Japan, 1978, vol. 51, No. 4, pp. 1158-1162.
Berger et al., "Zur Telomerisierung von Isopren mit Palladium-Komplexen bei niedriger Temperatur," Journal f. prakt. Chemie. Band, 1985, vol. 327, No. 4, pp. 643-618.

(Continued)

*Primary Examiner* — Brian McCaig
(74) *Attorney, Agent, or Firm* — Squire Sanders (US) LLP

(57) ABSTRACT

Provided herein are methods comprising catalytic dimerization of $\beta$-farnesene to obtain squalane and/or isosqualane. Compositions comprising squalane and/or isosqualane are provided. In certain embodiments, squalane and isosqualane prepared by the methods provided herein can be useful for applications in cosmetic industry and/or in the lubricants industry.

16 Claims, 31 Drawing Sheets

(56) References Cited

OTHER PUBLICATIONS

Dzhemilev et al., "Linear Dimerization and Codimerization of Substituted 1,3-Dienes Catalyzed by Zirconium Complexes,"Russian Chemical Bulletin, 1979, vol. 28, No. 9, pp. 1909-1919.

Vostrikova et al., "Codimerization of $C_6$-$C_{10}$ α-Olefins with Butadiene Using Zirconium Complexes," Russian Chemical Bulletin, 1981, vol. 30, No. 6, pp. 1132-1134.

Young, David A., "Synthesis and Structure of Zirconium Tetrachloride Ester Complexes, Ethylene Oligomerization Catalyst Precursors," Journal of Molecular Catalysis, 1989, vol. 53, pp. 433-442.

International Search Report and Written Opinion dated Aug. 24, 2011, in application No. PCT/US2011/037341 (11 pages).

Mondon, "Die Synthese des Isosqualens," *Chem. Berichte* (1955) 88:724-732.

Nakano et al., "Squalene-hopene cyclase: insight into the role of the methyl group on the squalene backbone upon the polycyclization cascade. Enzymatic cyclization products of squalene analogs lacking a 26-methyl group and possessing a methyl group at C(7) or C(11)," *Org Biomol Chem.* (2004) 2(14):2012-2022.

SQUALANE AND ISOSQUALANE COMPOSITIONS AND METHODS FOR PREPARING THE SAME

REFERENCE TO RELATED APPLICATIONS

This application claims priority to U.S. provisional application No. 61/347,366 filed May 21, 2010, to U.S. provisional application No. 61/391,538 filed Oct. 8, 2010 and to U.S. provisional application No. 61/447,689 filed Feb. 28, 2011, each of which is incorporated by reference herein in its entirety.

STATEMENT REGARDING FEDERALLY SPONSORED RESEARCH

Some of the work described herein was funded by Award No. DE-EE0002869 awarded by the U.S. Department of Energy. Accordingly, the Government may have rights to some embodiments of this invention.

FIELD

Provided herein are compositions comprising squalane and isosqualane, and methods for preparing the same. The methods comprise catalytic dimerization of β-farnesene, and hydrogenation of the dimerization reaction product to obtain a composition comprising squalane and isosqualane. In certain embodiments, the compositions described herein are useful for applications in the cosmetic industry, e.g., as emollients. In certain embodiments, the compositions described herein may be used as lubricant base oils, lubricant additives, lubricants, or as components in finished lubricant formulations.

BACKGROUND

Squalane is widely used in preparation of many cosmetics including creams, especially nutrient creams and medicated creams, milky lotion, toilet lotion, lipstick, foundation, and face powder. In addition, squalane is used as a fatting agent for high quality soap, and also used for producing medical and pharmaceutical preparations such as ointments, suppositories and medical lubricating agents. Squalene is present in the bodies of all fish, and may be extracted, for example, from the liver oil of deep-sea shark. Squalene can also be extracted in a multi-step process from vegetable oils, such as olive oil. Squalane can be produced by hydrogenating squalene from fish or vegetable oils. Squalane may be produced synthetically, for example, by the coupling of two molecules of geranyl acetone with diacetylene, followed by dehydration and complete hydrogenation; or by the dimerization of dehydronerolidol, followed by dehydration and hydrogenation.

U.S. Pat. No. 3,794,692, U.S. Pat. No. 3,859,374 and Akutagawa et al. in *Bulletin of the Chemical Society of Japan*, v.51(4), p. 1158-62 (1978) reported dimerization of farnesene and hydrogenation of the linear dimer to form squalane. However, as is described in detail herein, the '692 and '374 patents do not provide sufficient information to demonstrate that squalane was in fact prepared. NMR data reported in Akutagawa et al. for β-farnesene are inconsistent with that of β-farnesene known to be >97% pure, and NMR data reported in Akutagawa et al. for their linear dimer are inconsistent with the structure put forth for that linear dimer.

International Patent Publication No. WO 2010/042208 entitled "Farnesene dimers and/or farnesane dimers and compositions thereof" and filed Oct. 9, 2009 describes certain dimers and hydrogenated dimers of β-farnesene, including squalane.

Despite previous efforts to produce squalane that have been reported in the literature, there exists a need for renewable sources of squalane. There exists a continuing need for cost-effective methods for preparing squalane (e.g., high purity squalane) on large scales. There exists a need for methods that allow control of relative amounts of squalane and isomers of squalane, such isosqualane. There exists a need for squalane as well as for isosqualane that can be manufactured on large scale for use in, for example, the lubricants industry or in the cosmetic industry.

SUMMARY

In some embodiments, provided herein are methods for manufacturing squalane compositions by catalytic dimerization of β-farnesene. In some variations, the methods can be used for large scale manufacture of squalane. In some variations, the squalane compositions comprise at least about 80% squalane, e.g., about 80%, 85%, 88%, 90%, 92%, or 93% squalane. The squalane compositions produced by the methods described herein are differentiated from squalane derived from sharks, olive oil, and the like by the presence of isosqualane. In some variations, β-farnesene used to make squalane as described herein is produced by genetically modified microorganisms using a renewable carbon source.

In some embodiments, provided herein are methods for manufacturing isosqualane compositions by catalytic dimerization of β-farnesene. In some variations, the methods can be used for large scale manufacture of isosqualane. In some variations, the isosqualane compositions produced by the methods described herein comprise at least about 80% or more isosqualane, e.g., about 80%, 85%, 88%, 90%, 92%, 95%, or 98% isosqualane. In some variations, β-farnesene used to make isosqualane as described herein is produced by genetically modified microorganisms using a renewable carbon source.

In certain embodiments, provided herein are methods for catalytic dimerization of β-farnesene to obtain isosqualene and/or one or more structural isomers of isosqualene. In certain embodiments, the methods comprise (a) catalytic dimerzation of β-farnesene to obtain a reaction product comprising isosqualene and one or more structural isomers of isosqualene, and (b) hydrogenation of the reaction product to obtain a composition comprising squalane and isosqualane. In some variations, isosqualane is present as at least about 10% of the composition.

In certain embodiments, the dimerization is conducted in the presence of a palladium catalyst. In certain embodiments, the dimerization reaction provided herein results in about 80% or greater conversion of β-farnesene to a linear dimer product in the dimerization reaction, based on the amount of β-farnesene present in the reactants. In certain embodiments, the dimerization reaction provided herein selectively produces about 80% or greater isosqualene, based on the total amount of linear dimer product formed.

In certain embodiments, the catalytic dimerization provided herein uses a palladium catalyst formed from a palladium precursor selected from [Pd(allyl)Cl]$_2$, Pd(cod)Cl$_2$, Pd$_2$(dba)$_3$, Pd(dba)$_2$, Pd(dba), Pd(acac)$_2$, or an equimolar mixture of Pd(dba)$_3$ and Pd$_2$(dba)$_3$.

In certain embodiments, the catalyst uses a ligand selected from triphenyl phosphine, triethyl phosphine and tritolyl phosphine. In certain embodiments, the ligand is in about one or more equivalents for each equivalent of the palladium precursor. In certain embodiments, the dimerization is carried out in the presence of a base. In certain embodiments, the base is in an amount from about 15-40 mol % or about 20 mol %. In certain embodiments, the dimerization is carried out without any base. In certain embodiments, the reaction is carried out in a protic solvent, such as a primary or a secondary alcohol.

In certain embodiments, methods for preparation of isosqualene comprise contacting β-farnesene with a palladium catalyst in the presence of a protic solvent, wherein the palladium catalyst comprises palladium(II) acetylacetonate and a triphenyl phosphine ligand, and a substrate to catalyst ratio is in a range from about 250/1 to 5000/1, e.g., about 250/1, 400/1, 500/1, 700/1, 800/1, 900/1, 1000/1, 1100/1, 1250/1, 1500/1, 1750/1, 2000/1, 2500/1, 3000/1, 3500/1, 4000/1, 4500/1 or 5000/1.

In certain embodiments, the catalytic dimerization provided herein is carried out in the presence of a palladium carbene. In certain embodiments, the palladium carbene is formed by reacting $Pd(acac)_2$ with an imidazolium salt. In certain embodiments, the imidazolium salt is 1,3-bis-(2,6-diisopropylphenyl)-4,5-dihydroimidazolium tetrafluoroborate.

In certain embodiments, the catalytic dimerization of β-farnesene is conducted in the presence of a nickel catalyst. In certain embodiments, the nickel catalyst used herein is selected from $Ni(cod)_2$, $Ni(PPh_3)_4$, $Ni(PPh_3)_2Cl_2$ and $Ni(acac)_2$. In certain embodiments, the nickel catalyzed dimerization reaction yields a mixture of squalane, isosqualane and neosqualane after hydrogenation. In certain variations, the nickel catalyzed dimerization reaction yields a mixture of squalane and isosqualane, wherein isosqualane is the predominant product.

In certain embodiments, provided herein are methods comprising dimerizing β-farnesene in the presence of a zirconium catalyst such as a zirconium alkoxide (e.g., zirconium tetrakis (tert-butoxide) or a zirconium halide (e.g., $ZrCl_4$) and a metal alkyl co-catalyst to form a dimerization product, and hydrogenating the dimerization product to produce a composition comprising isosqualane. Certain variations of these methods produce a composition comprising isosqualane and squalane. Certain variations of these methods produce a composition comprising isosqualane, squalane and neosqualane. The alkyl aluminum co-catalyst may, for example, be diethyl aluminum chloride.

In certain embodiments, provided here are methods for preparation of a composition, the method comprising contacting β-farnesene with i) a palladium carbene in the presence of a base in a protic solvent, or ii) a zirconium catalyst to form a dimerization product; and hydrogenating the product to produce a composition comprising squalane and isosqualane.

In certain embodiments, the hydrogenation reaction can be carried out in the presence of hydrogen with a catalyst such as Pd, Pd/C, Pt, $PtO_2$, $Ru(PPh_3)_3Cl_2$, Ru/C, $Rh(PPh_3)_3Cl$, Raney nickel, Ni, or any combination thereof.

In certain embodiments, the methods provided herein can cost-effectively produce high purity squalane. In certain embodiments, squalane obtained from the process herein has a purity of about 80%, 81%, 82%, 83%, 84%, 85%, 86%, 87%, 88%, 89%, 90%, 91%, 92%, 93%, 94%, 95%, 96%, 97%, or 98%. Such high purity squalane can be useful in, for example, cosmetic industry.

In certain embodiments, the methods provided herein can produce a composition comprising squalane and isosqualane, wherein a ratio (quantity squalane):(quantity isosqualane) is about 2:1 or higher, e.g., about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 26:1.

In certain embodiments, the methods provided herein can produce a composition comprising squalane and isosqualane, wherein a ratio (quantity isosqualane):(quantity squalane) is about 1:1 or greater, e.g., about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 40:1, 50:1, or 60:1.

In certain embodiments, provided herein are compositions comprising squalane and isosqualane, wherein the amount of isosqualane is about 10% or more (e.g., 10%, 20%, 30%, 40%, 50%, 60%, 70%, 80%, 90%, 92%, 94%, 96%, 98%, 99%, 99.5%, or 99.9%) and the amount of squalane is about 0.1% or more (e.g., 0.1%, 0.5%, 1%, 2%, 3%, 5%, 10%, 15%, 20%, 25%, 30%, 35%, 40%, 45%, 50%, 55%, 60%, 65%, 70%, 75%, 80%, 85%, 86%, 87%, 88%, 89% or 90%), based on the total composition. For example, in some variations, the quantity of squalane in a composition is about 90%, and the quantity of isosqualane in the composition is about 10%. In some variations, the quantity of squalane is about 80%, and the quantity of isosqualane is about 20%. In some variations, the quantity of squalane is about 70%, and the quantity of isosqualane is about 30%. In some variations, the quantity of squalane is about 60% and the quantity of isosqualane is about 40%. In some variations, the quantity of squalane is about 50% and the quantity of isosqualane is about 50%. In some variations, the quantity of squalane is about 40% and the quantity of isosqualane is about 60%. In some variations, the quantity of squalane is about 30% and the quantity of isosqualane is about 70%. In some variations, the quantity of squalane is about 20% and the quantity of isosqualane is about 80%. In some variations, the quantity of squalane is about 10% and the quantity of isosqualane is about 90%. In some variations, the quantity of squalane is about 5% and the quantity of isosqualane is about 95%. In some variations, the quantity of squalane is about 1% and the quantity of isosqualane is about 99%. In some variations, the quantity of squalane is about 0.1% and the quantity of isosqualane is about 99.9%. In certain variations, the compositions additionally comprise neosqualane.

In certain embodiments, provided herein are compositions comprising squalane and isosqualane, wherein a ratio of (quantity squalane):(quantity isosqualane) is about 20:1 or less, e.g., about 0.01:1, 0.05:1, 0.1:1, 0.5:1, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or 20:1. In some variations, the compositions comprising squalane and isosqualane further comprise neosqualane.

In some variations, any of the compositions described herein are used in cosmetic products, or as emollients. In certain variations, the cosmetic products or emollients may comprise at least about 90 wt % squalane and at least about 0.1 wt % isosqualane but less than or equal to about 10 wt % isosqualane. In certain variations, the cosmetic products or emollients may comprise at least about 90 wt % squalane and about 0.1-5 wt % isosqualane. In certain variations, the cosmetic products or emollients may comprise at least about 92 wt % squalane and about 0.1-5 wt % isosqualane. In certain variations, the cosmetic products or emollients may comprise at least about 10 wt % isosqualane, e.g., a cosmetic product or emollient may comprise about 10 wt %, 15 wt %, 20 wt %, 25 wt %, 30 wt %, 35 wt %, 40 wt %, 45 wt %. 50 wt %, 60 wt %, 65 wt %, 70 wt %, 75 wt %, 80 wt %, 85 wt %, 90 wt %, or 95 wt % isosqualane.

In some variations, the compositions described herein are used as vaccine adjuvants. In certain variations, the vaccine adjuvants may comprise at least about 90 wt % squalane and at least about 0.1 wt % isosqualane but less than or equal to about 10 wt % isosqualane. In certain variations, the vaccine adjuvants may comprise at least about 90 wt % squalane and about 0.1-5 wt % isosqualane. In certain variations, the vaccine adjuvants may comprise at least about 92 wt % squalane and about 0.1-5 wt % isosqualane.

In some variations, the compositions described herein are used as lubricant base stocks, as lubricants, or as a component in a lubricant formulation. Some variations of lubricant formulations comprise at least about 5 wt %, 10 wt %, 20 wt %, 30 wt %, 40 wt %, 50 wt %, 60 wt %, 70 wt %, 80 wt %, 90 wt %, or 100 wt % of a composition disclosed herein. The lubricant formulations may comprise an additive selected from the group consisting of a rust inhibitor, a viscosity modifier, an antioxidant, a flame retardant, an antiwear agent, a pour point modifier, a dispersant, a seal swell agent, a corrosion inhibitor, a demulsifier, a solubilizer, or any combination of two or more of the foregoing, in addition to a composition described herein.

DESCRIPTION

Figure 1:
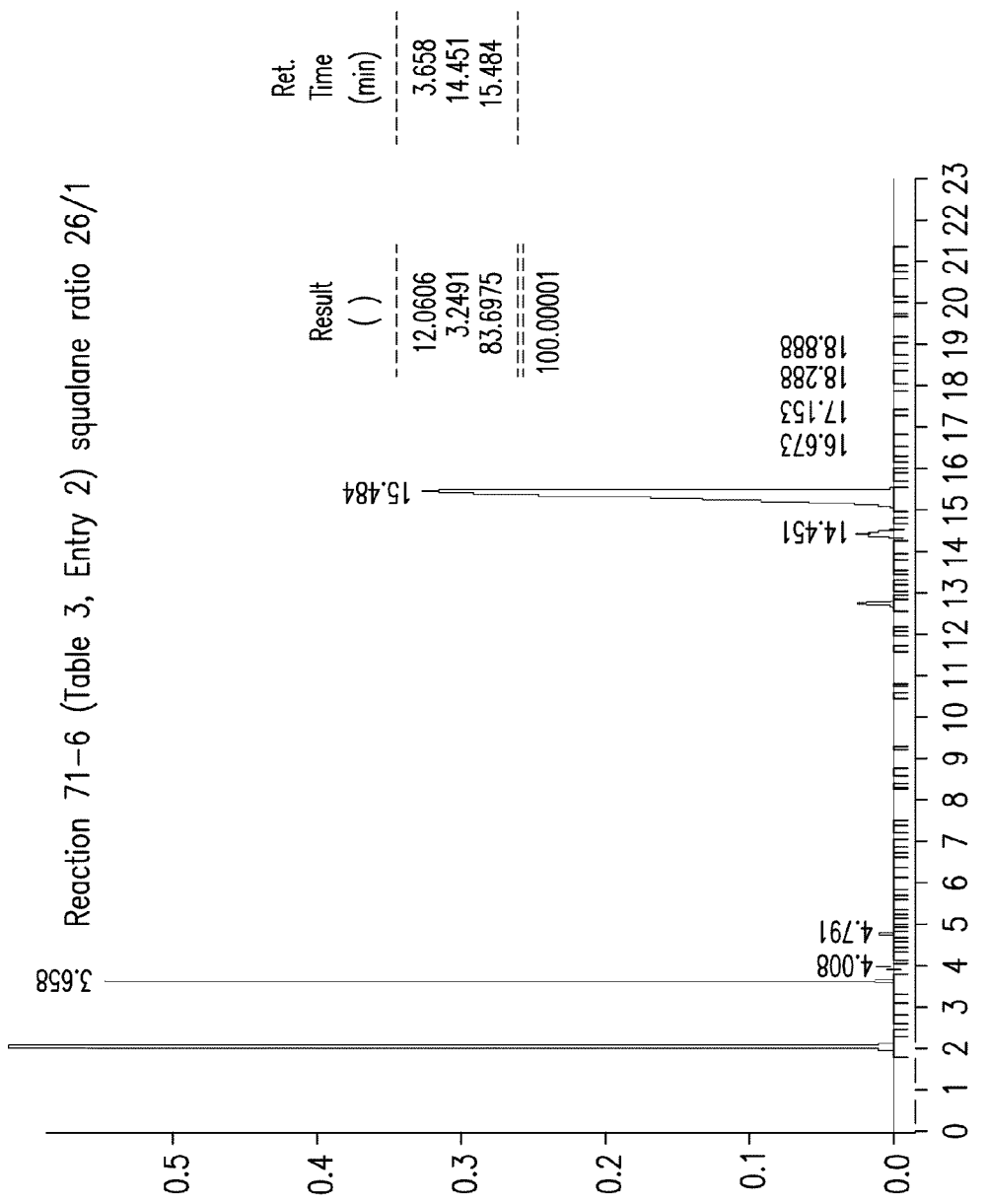
FIG. 1 provides a GC spectrum for the reaction described in Table 3, entry 2.

International Patent Publication No. WO 2010/042208 entitled "Farnesene dimers and/or farnesane dimers and compositions thereof" and filed Oct. 9, 2009 describes dimerization of β-farnesene to form a linear dimer, which is hydrogenated to make squalane. Described herein are methods employing alternate catalyst systems to produce squalane from β-farnesene, e.g., less expensive catalyst systems that can be used to manufacture squalane compositions on large scale. The squalane so produced is distinguishable from squalane derived from sharks or squalane derived from olive oil by the presence of isosqualane, and in some embodiments is suitable for use in cosmetics applications or for use in lubricants. Also described herein are compositions comprising squalane and isosqualane (e.g., at least about 10% isosqualane), and methods for making the same. The compositions comprising squalane and isosqualane described herein are suitable for use in lubricants in some variations. Further, described herein are compositions in which the relative amounts of squalane and isosqualane can be controlled, and methods for making the same.

In certain embodiments, provided herein are squalane compositions (e.g., squalane having a purity of about 80% or greater, e.g., about 80%, 85%, 88%, 90%, 92%, or 93% based on the total composition, where % refers to wt %, area % or vol %) produced by catalytic dimerization of β-farnesene. In some variations, the β-farnesene used to produce the squalane described herein is produced by genetically modified microorganisms using a renewable carbon source.

In certain embodiments, provided herein are compositions comprising squalane and isosqualane, which may for example, be produced by catalytic dimerization of β-farnesene. A wide range of compositions in which the relative quantities of squalane and isosqualane are varied are described herein. The relative amounts of squalane and isosqualane in compositions described herein can be tuned over a large range by appropriate selection of the dimerization catalyst. In some variations, the catalyst can be selected to produce predominantly squalane, and in certain variations, squalane having a purity of about 80% or greater (e.g., about 80%, 85%, 88%, 90%, 92, or 93%) can be achieved. In some variations, the catalyst can be selected to produce predominantly isosqualane, and in certain variations, isosqualane having a purity of greater than about 80% (e.g., about 80%, 85%, 88%, 90%, or 95%) can be achieved. In some variations, the β-farnesene is produced by genetically engineered microorganisms using a renewable carbon source. In some embodiments, provided herein are compositions comprising squalane, isosqualane and neosqualane.

In certain embodiments, methods for catalytic dimerization of β-farnesene to obtain a mixture comprising isosqualene and one or more isomers of isosqualene are provided herein. In certain embodiments, provided herein are methods for preparation of compositions comprising squalane and isosqualane from β-farnesene. In certain embodiments, provided herein are methods for preparation of compositions comprising squalane, isosqualane, and neosqualane from β-farnesene.

DEFINITIONS

In the following description, all numbers disclosed herein are approximate values, regardless whether the word "about" or "approximate" is used in connection therewith. Numbers may vary by 1 percent, 2 percent, 5 percent, or, sometimes, 10 to 20 percent. Whenever a numerical range with a lower limit, $R^L$, and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

As used herein, "β-farnesene" refers to a compound having the following formula:

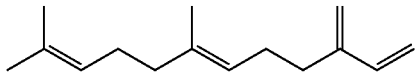

or a stereoisomer thereof. In some embodiments, the β-farnesene comprises a substantially pure stereoisomer of β-farnesene. In other embodiments, the β-farnesene comprises a mixture of stereoisomers, such as cis-trans isomers. In further embodiments, the amount of each of the stereoisomers in the β-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, from about 20 wt. % to about 80 wt. %, based on the total weight of the β-farnesene mixture.

As used herein, "squalane" refers to a compound having the following formula:

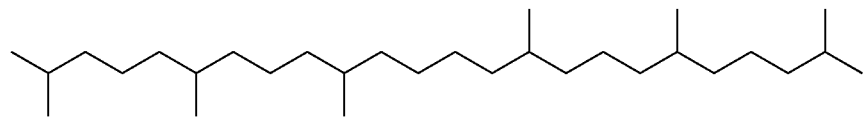

As used herein, "iso-squalane" or "isosqualane" refers to a compound having the following formula:

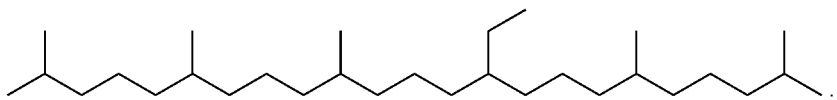 [SMILES: CCC(CCCC(C)CCCC(C)C)CCCC(C)CCCC(C)CCCC(C)C]

As used herein, "neosqualane" refers to a compound having the following formula:

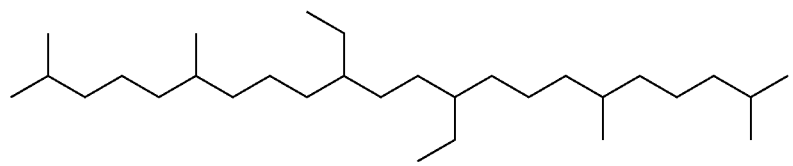

As used herein, "squalene" refers to a compound having the following formula:

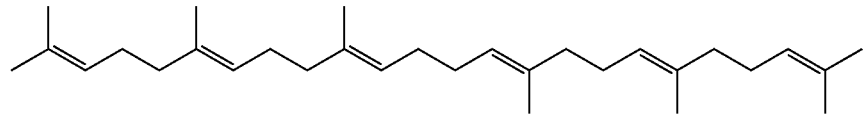

As used herein, "iso-squalene" or "isosqualene" refers to a compound having the following formula:

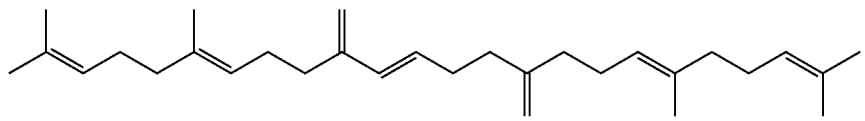

One or more isomers of isosqualene having the molecular formula $C_{30}H_{48}$ may be present in the reaction product that results from the dimerization of β-farnesene as described herein. One possible isomer of isosqualene that may be formed from a dimerization reaction of β-farnesene described herein and may be hydrogenated to form isosqualane has the following formula (and is also referred to as compound B1 herein):

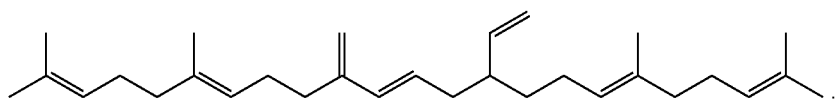 [SMILES: C=CC(C/C=C/C(=C)CC/C=C(\C)CCC=C(C)C)CC/C=C(\C)CCC=C(C)C]

The chemical name for compound B1 is (6E,11E,17E)-2,6,18,22-tetramethyl-10-methylene-14-vinyltricosa-2,6,11,17,21-pentaene.

Another possible isomer of isosqualene that may be formed from a dimerization reaction of β-farnesene described herein and may be hydrogenated to form isosqualane has the following formula (and is also referred to as compound D herein):

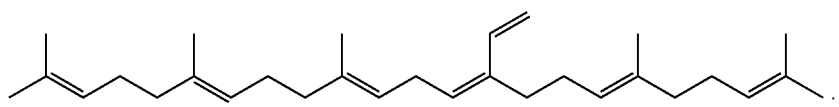 [SMILES: C=C/C(=C\C/C=C(\C)CC/C=C(\C)CCC=C(C)C)CC/C=C(\C)CCC=C(C)C]

Another possible isomer of isosqualene that may be formed in a dimerization reaction of β-farnesene described herein and may be hydrogenated to form neosqualane has the following formula (and is also referred to as compound A2 herein):

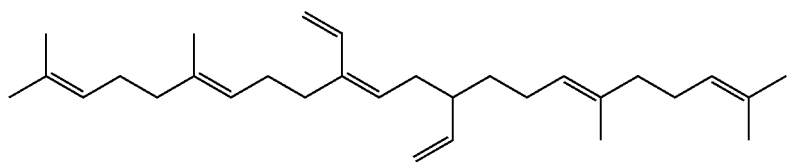

In some embodiments, the dimerization reaction product includes isosqualene and isosqualene isomers (e.g., compounds B1 and/or D) that are hydrogenated to form isosqualane. In some embodiments, the dimerization reaction product includes isosqualene, isosqualene isomers that are hydrogenated to form isosqualane (e.g., compound B1 and/or compound D), and isosqualene isomers that are hydrogenated to form neosqualane (e.g., compound A2).

As used herein, the term "phosphine ligand" refers to a ligand having the general formula $PR_3$, where R=alkyl, aryl, H, halide, etc. Phosphine ligands can afford reactive and versatile homogeneous catalysts in various reactions, including the catalytic dimerization reactions described herein.

The "imidazolium salt" and "imidazolinium (i.e., dihydroimidazolium) salt" for use herein include any imidazolium salt and dihydroimidazolium salt suitable for in situ generation of palladium carbenes, including, but not limited to salts selected from 1,3-bis(mesityl)-4,5-dimethylimidazolium chloride; 1,3-bis(mesityl)-4,5-dimethylimidazolinium chloride; 1,3-bis(2,6-diisopropylphenyl)-4,5-dimethylimidazolium chloride; 1,3-bis(2,6-diisopropylphenyl)-4,5-dimethylimidazolinium chloride; 1,3-bis(mesityl)-4,5-dichlorolimidazolium chloride; 1,3-bis-(mesityl)imidazolium chloride (IMes.HCl); 1,3-bis-(2,6-diisopropylphenyl)imidazolium chloride (IPr.HCl); 1,3-bis-(adamantly)imidazolium chloride (IAd.HCl); 1,3-bis-(cyclohexyl)imidazolium chloride (ICy.HCl); 1,3-bis-(2,6-dimethylphenyl)imidazolium chloride (IXy.HCl); 1,3-bis-(tolyl)imidazolium chloride (ITol.HCl); dispiro(cyclohexane-1,3'(2'H)-imidazo(5,1-b:4,3-b')bisoxazol(4)ium-7'(8'H),1"-cyclohexane)trifluoromethanesulfonic acid salt (IBiox6.HOTf); 1,3-bis-(mesityl)-4,5-dihydroimidazolium chloride (SIMes.HCl); 1,3-bis-(2,6-diisopropylphenyl)-4,5-dihydroimidazolium chloride (SIPr.HCl); 1,3-bis-(adamantyl)-4,5-dihydroimidazolium chloride (SIAd.HCl); 1,3-bis-(cyclohexyl)-4,5-dihydroimidazolium chloride (SICy.HCl); 1,3-bis-(2,6-dimethylphenyl)-4,5-dihydroimidazolium chloride (SIXy.HCl); 1,3-bis-(tolyl)-4,5-dihydroimidazolium chloride (SITol.HCl); 1,3-bis-(mesityl)-4,5-dihydroimidazolium tetrafluoroborate (SIMes.HBF$_4$); 1,3-bis-(2,6-diisopropylphenyl)-4,5-dihydroimidazolium tetrafluoroborate (SIPr.HBF$_4$); 1,3-bis-(adamantyl)-4,5-dihydroimidazolium tetrafluoroborate (SIAd.HBF$_4$); 1-(2,6-diisopropylphenyl)-3-(2,4,6-trimethylphenyl)-imidazolinium chloride; 2-(2,6-diisopropylphenyl)-5-methylimidazo[1,5-c]pyridinium hexafluorophosphate; 2-mesityl-5-methylimidazol[1,5-c]pyridinium chloride; 1-(1-adamantyl)-3-(2,4,6-trimethylphenyl)imidazolinium chloride; 1,3-di-tert-butylimidaolinium tetrafluoroborate; 1,3-di-tert-butylimidazolium tetrafluoroborate; and 4,5-dimethyl-1,3-bis-(2,6-diisopropylphenyl)imidazolium tetrafluoroborate.

As used herein, "% conversion of β-farnesene" refers to the amount of β-farnesene converted to a product in the dimerization reaction based on the amount of β-farnesene present in the reactants.

As used herein, "% selectivity for isosqualene" refers to the amount of isosqualene formed in the dimerization reaction based on the total amount of product formed. In certain embodiments, the dimerization reaction provided herein selectively produces about 80%, 81%, 82%, 83%, 84%, 85%, 86%, 87%, 88%, 89%, 90%, 91%, 92%, 93%, or 94% or greater isosqualene based on the total amount of product formed. In certain embodiments, the remaining fraction (about 20% or less) of the product in the dimerization reaction that is not isosqualene comprises unreacted farnesene and one or more isomers of isosqualene, such as compound B1, compound D and compound A2. In certain embodiments, the dimerization reaction forms thermal dimer (e.g., compounds DA1 and DA2 shown below) impurities, as described below. Other possible impurities present in the dimerization reaction product include unsaturated farnesol.

For determination of relative or absolute quantities of squalane, isosqualane and neosqualane in any of the compositions described herein, any suitable analytical method may be used, e.g., each of the squalane, isosqualane and neosqualane components of a composition may be quantified by chromatography such as gas chromatograph (e.g., GC-MS or GC-FID). Area per area percent (a/a % or area %) of elution peaks associated with each of squalane, isosqualane and neosqualane can be measured and quantified using known techniques, or weight per weight percent (w/w % or wt %) of each of squalane, isosqualane and neosqualane in a composition may be determined using known techniques for mass assay following GC-FID analysis, e.g., by using a standard squalane sample having a purity of greater than 99% (e.g., 99.7% pure) as a reference. Squalane having a purity of 99.7% derived from shark oil may be purchased from Jedwards, International, Quincy, Mass. For any of the compositions disclosed herein, quantities of squalane, isosqualane or neosqualane given as percentages refer to any of wt %, area %, or vol %, unless specifically indicated otherwise.

As used herein, the abbreviations for compounds, are, unless indicated otherwise, in accord with their common usage, recognized abbreviations, IUPAC Chemical Nomenclature, or the IUPAC-IUB Commission on Biochemical Nomenclature.

Compositions

Provided herein are squalane compositions comprising about 80% or more squalane (e.g., about 80%, 85%, 86%, 87%, 88%, 89%, 90%, 91%, 92% or 93%) produced by catalytic dimerization of β-farnesene, e.g., β-farnesene produced by genetically engineered microorganisms using a renewable carbon source. The squalane compositions described herein are differentiated from squalane derived from sharks or from olive oil by the presence of isosqualane.

Also provided herein are compositions comprising squalane and isosqualane (e.g., at least about 10% isosqualane). In certain variations, the compositions are produced by catalytic dimerization of β-farnesene. In some embodiments, the compositions comprise squalane, isosqualane and neosqualane. A wide range of compositions in which the relative quantities of squalane and isosqualane are varied are described herein. In some variations of the compositions, the quantity of squalane is greater than the quantity of isosqualane. For example, the dimerization catalyst can be selected to produce predominantly squalane, and in certain variations, squalane having a purity of about 80% or greater (e.g., about 80%, 85%, 88%, 90%, 92%, or 93%) can be achieved. In some variations of the compositions, the quantities of isosqualane and squalane are similar. In some variations of the compositions, the quantity of isosqualane is greater than the quantity of squalane in the compositions. For example, the dimerization catalyst can be selected to produce predominantly isosqualane, and in certain variations, isosqualane having a purity of about 80% or greater (e.g., about 80%, 85%, 90%, or 95%) can be achieved. Also provided herein are compositions comprising isosqualane and neosqualane. In some variations of the compositions, the quantity of isosqualane present is greater than the quantity of neosqualane present.

In some embodiments, the relative amounts of squalane and isosqualane in a composition are adjusted by blending two or more compositions together. For example, a first composition comprising 80% or more squalane can be blended with a substantially equal amount of a second composition comprising 80% or more isosqualane to produce a composition having similar amounts of squalane and isosqualane. By blending two or more compositions in such a manner, the relative quantities of squalane and isosqualane can be varied or tuned on a continuous basis.

In some variations of the compositions disclosed herein, a ratio of the quantity of squalane to the quantity of isosqualane is about 2:1 or greater, e.g., about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 26:1. In some variations of the compositions, the quantity of squalane is about the same as the quantity of isosqualane, so that the ratio (quantity squalane):(quantity isosqualane) is about 1:1. In some variations of the compositions, the quantity of isosqualane is greater than the quantity of squalane, e.g., the ratio (quantity squalane):(quantity isosqualane) is about 0.01:1, 0.02:1, 0.04:1, 0.06:1, 0.08:1, 0.1:1, 0.25:1, 0.33:1, or 0.5:1. Any one of the compositions described herein may additionally comprise neosqualane. In certain variations of those compositions comprising neosqualane, the ratio (quantity squalane+quantity isosqualane):(quantity neosqualane) may be about 10:1, 20:1, 50:1, 100:1, 500:1, or 1000:1.

In a composition, the combined quantities of squalane and isosqualane may comprise at least about 5% of the total quantity of the composition, with % being measured as wt %, vol %, or as area % determined by chromatography (e.g., GC such as GC-FID or GC-MS). For example, the combined quantities of squalane and isosqualane in a composition may comprise about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, or 98%, with % representing wt %, vol %, or area %, based on the total quantity of the composition. In a composition that comprises neosqualane, the combined quantities of squalane, isosqualane, and neosqualane may comprise at least about 5% of the total quantity of the composition, e.g., about 5%, 10%, 15%, 20%, 25%, 30%, 35%, 40%, 45%, 50%, 55%, 60%, 65%, 70%, 75%, 80%, 80%, 81%, 82%, 83%, 84%, 85%, 86%, 87%, 88%, 89%, 90%, 91%, 92%, 93%, 94%, 95%, 96%, 97%, or 98%, with % representing wt %, vol %, or area %, based on the total quantity of the composition. In certain embodiments, the combined weights of squalane, isosqualane and neosqualane (if present) may comprise less than about 5% (wt %, vol %, or area %) of the composition, e.g., about 0.5%, 1%, 2%, 3%, or 4%.

Also provided herein are compositions comprising squalane and isosqualane, wherein a quantity of squalane in the composition is about 5% or greater of the total composition (e.g., about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97% or 98%), and a quantity of isosqualane in the composition is greater than about 0.1% of the total composition, with quantities being measured as wt %, vol %, or area % by chromatography (e.g., GC-FID or GC-MS). In some variations, the quantity of squalane in a composition is about 5% or greater (e.g., about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97% or 98%), and the quantity of isosqualane in the composition is about 1% or greater. In some variations, the quantity of squalane in a composition is about 5% or greater (e.g., about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, or 98%) and the quantity of isosqualane in the composition is equal to or greater than about 0.1% but less than or equal to about 20% (e.g., about 20%, 15%, 10%, 9%, 8%, 7%, 6%, 5%, 4%, 3%, 2%, 1%, 0.8%, 0.5%, 0.3%, 0.2%, 0.1%). For example, in some variations, the quantity of squalane in a composition may be about 90% or greater of the total composition and the quantity of isosqualane in the composition may be greater than or equal to about 0.1% but less than or equal to about 10% (% measured as wt %, vol %, or area %). In some variations, the quantity of squalane in a composition is about 90% or greater and the quantity of isosqualane in the composition is greater than or equal to about 0.1% but less than or equal to about 5% (measured as wt %, vol %, or area %). In some variations, the quantity of squalane in a composition is about 92% or greater and the quantity of isosqualane in the composition is greater than or equal to about 0.1% but less than or equal to about 8% (measured as wt %, vol %, or area %). In some compositions, the quantity of squalane is about 92% or greater and the amount of isosqualane is greater than or equal to about 0.1% but less than or equal to about 5% (measured as wt %, vol %, or area %).

Also provided herein are compositions comprising squalane and isosqualane, wherein a quantity of isosqualane in the composition is about 10% or greater of the total composition (e.g., about 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97% or 98%), and a quantity of squalane in the composition is greater than about 0.1% of the total composition, with quantities being measured as wt %, vol %, or area % by chromatography (e.g., GC-FID or GC-MS). In some variations, the quantity of isosqualane in a composition is about 10% or greater (e.g., about 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97% or 98%), and the quantity of squalane in the composition is about 1% or greater. In some variations, the quantity of isosqualane in a composition is about 10% or greater (e.g., about 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, or 98%) and the quantity of squalane in the composition is about 10% or greater (e.g., about 10%, 15%, 20%, 25%, 30%, 35%, 40%, 45%, 50%, 55%, 60%, 65%, 70%, 75%, 80%, 85% or 90%). For example, in some variations, the quantity of squalane in a composition may be about 60% of the total composition and the quantity of isosqualane in the composition may be greater than or equal to about 10%. In some variations, the quantity of squalane in a composition is about 70% and the quantity of isosqualane is about 10% or greater. In some variations, the quantity of squalane in a composition is about 80% and the quantity of isosqualane in the composition is about 10% or greater. In some compositions, the quantity of squalane is about 90% and the amount of isosqualane is about 10% (measured as wt %, vol %, or area %).

Table 1A below provides some non-limiting examples of compositions comprising squalane and isosqualane, where each "X" specifically discloses a composition that comprises the quantity of squalane indicated in the row heading and the quantity of isosqualane indicated in the column heading. In Table 1A, the quantities of squalane and isosqualane as given as wt %, vol %, or area % measured by chromatography, e.g., GC such as GC-MS or GC-FID, based on the total composition. Each of the ranges in Table 1A specifically discloses the numerical values provided as lower limits $R^L$ and upper limits $R^U$, and also specifically discloses values within the range limits, e.g., each of the following numbers within each range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent.

Any of the compositions listed above or shown in Table 1A may additionally comprise neosqualane. In some variations of the compositions, the wt. %, area % or vol % of neosqualane in the compositions is about 0.1% or greater.

TABLE 1A

Exemplary compositions comprising squalane and isosqualane.

| | | % Isosqualane (% measured as wt %, vol % or area %) | | | | | | | | | | |
|---|---|---|---|---|---|---|---|---|---|---|---|---|
| | | 0.1-1 | 1-2 | 2-3 | 3-4 | 4-5 | 5-6 | 6-8 | 8-10 | 10-12 | 12-15 | 15-18 | 18-20 |
| % Squalane (% measured as wt %, vol % or | 5-10 | X | X | X | X | X | X | X | X | X | X | X |
| | 10-20 | X | X | X | X | X | X | X | X | X | X | X |
| | 20-30 | X | X | X | X | X | X | X | X | X | X | X |
| | 30-40 | X | X | X | X | X | X | X | X | X | X | X |

TABLE 1A-continued

Exemplary compositions comprising squalane and isosqualane.

| | | % Isosqualane (% measured as wt %, vol % or area %) | | | | | | | | | | |
|---|---|---|---|---|---|---|---|---|---|---|---|---|
| | | 0.1-1 | 1-2 | 2-3 | 3-4 | 4-5 | 5-6 | 6-8 | 8-10 | 10-12 | 12-15 | 15-18 | 18-20 |
| area %) | 40-50 | X | X | X | X | X | X | X | X | X | X | X | X |
| | 50-60 | X | X | X | X | X | X | X | X | X | X | X | X |
| | 60-70 | X | X | X | X | X | X | X | X | X | X | X | X |
| | 70-80 | X | X | X | X | X | X | X | X | X | X | X | X |
| | 80-84 | X | X | X | X | X | X | X | X | X | X | X | X |
| | 84-85 | X | X | X | X | X | X | X | X | X | X | X | |
| | 85-86 | X | X | X | X | X | X | X | X | X | X | X | |
| | 86-87 | X | X | X | X | X | X | X | X | X | X | | |
| | 87-88 | X | X | X | X | X | X | X | X | X | X | | |
| | 88-89 | X | X | X | X | X | X | X | X | X | X | | |
| | 89-90 | X | X | X | X | X | X | X | X | X | | | |
| | 90-91 | X | X | X | X | X | X | X | X | X | | | |
| | 91-92 | X | X | X | X | X | X | X | X | | | | |
| | 92-93 | X | X | X | X | X | X | X | X | | | | |
| | 93-94 | X | X | X | X | X | X | X | | | | | |
| | 94-95 | X | X | X | X | X | X | X | | | | | |
| | 95-96 | X | X | X | X | X | X | | | | | | |
| | 96-97 | X | X | X | X | X | | | | | | | |
| | 97-98 | X | X | X | X | | | | | | | | |

Any one of the compositions disclosed in Table 1A may include any amount of neosqualane. For example, in some variations, for any one of the compositions indicated in Table 1A, the content of neosqualane may be non-detectable, e.g., less than about 0.01%. In other variations, the composition may comprise about 0.1% to about 10% of the composition (by wt %, vol % or area %) neosqualane, e.g., any one of the compositions in Table 1A may independently comprise about 0.1, 0.2, 0.5, 1, 2, 3, 4, 5, 6, 7, 8, 9, or 10% neosqualane.

Table 2A provides additional non-limiting examples of compositions that are disclosed herein, e.g., compositions in which the quantity of isosqualane is comparable to or greater than the quantity of squalane in that composition. Each "X" specifically discloses a composition having the quantity isosqualane indicated in the column heading and the quantity squalane indicated in the row heading, where % means wt. %, vol %, or area % by chromatography (e.g., GC such as GC-MS or GC-FID), based on the total composition. Each of the ranges in Table 2A specifically discloses the numerical values provided as lower limits $R^L$ and upper limits $R^U$, and also specifically discloses values within the range limits, e.g., each of the following numbers within each range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, ..., 50 percent, 51 percent, 52 percent, ..., 95 percent, 96 percent, 97 percent, 98 percent, 99 percent, or 100 percent.

Any one of the compositions in Table 2A may comprise neosqualane. For example, any one of the compositions in Table 2A may independently comprise about 0.1, 0.2. 0.5, 1, 2, 3, 4, 5, 6, 7, 8, 9, or 10% neosqualane. Any one of the compositions in Table 2A may contain no detectable amount of neosqualane, e.g., less than about 0.01%.

TABLE 2A

Additional exemplary compositions comprising squalane and isosqualane.

| | | % Isosqualane (% measured as wt %, vol %, or area %) | | | | | | | | | | | | | |
|---|---|---|---|---|---|---|---|---|---|---|---|---|---|---|---|
| | | 30-35 | 35-40 | 40-45 | 45-50 | 50-55 | 55-60 | 60-65 | 65-70 | 70-75 | 75-80 | 80-85 | 85-90 | 90-95 | 95-100 |
| % Squalane | 0-1 | X | X | X | X | X | X | X | X | X | X | X | X | X | X |
| (% measured | 1-2 | X | X | X | X | X | X | X | X | X | X | X | X | X | X |
| as wt %, | 2-3 | X | X | X | X | X | X | X | X | X | X | X | X | X | X |
| vol %, or | 3-4 | X | X | X | X | X | X | X | X | X | X | X | X | X | X |
| area %) | 4-5 | X | X | X | X | X | X | X | X | X | X | X | X | X | X |
| | 5-6 | X | X | X | X | X | X | X | X | X | X | X | X | | |
| | 6-7 | X | X | X | X | X | X | X | X | X | X | X | X | | |
| | 7-8 | X | X | X | X | X | X | X | X | X | X | X | X | | |
| | 8-9 | X | X | X | X | X | X | X | X | X | X | X | X | | |
| | 9-10 | X | X | X | X | X | X | X | X | X | X | X | X | | |
| | 10-15 | X | X | X | X | X | X | X | X | X | X | X | X | | |
| | 15-20 | X | X | X | X | X | X | X | X | X | X | | | | |
| | 25-30 | X | X | X | X | X | X | X | X | X | X | | | | |
| | 30-35 | X | X | X | X | X | X | X | X | X | | | | | |
| | 35-40 | X | X | X | X | X | X | | | | | | | | |
| | 40-45 | X | X | X | X | X | X | | | | | | | | |
| | 45-50 | X | X | X | X | X | | | | | | | | | |
| | 50-55 | X | X | X | X | | | | | | | | | | |
| | 55-60 | X | X | X | | | | | | | | | | | |
| | 60-65 | X | X | | | | | | | | | | | | |
| | 65-70 | X | | | | | | | | | | | | | |

Also disclosed herein are compositions comprising isosqualene and at least about 0.1%, or at least about 1% of one or more structural isomers of isosqualene, e.g., one or more structural isomers of isosqualene selected from the group consisting of compound B1, compound D, and compound A2. For example, some compositions comprise isosqualene and compound B1, compound D, and compound A2. Some variations of the compositions comprise isosqualene and about 0.1-20% of one or more structural isomers of isosqualene, e.g., one or more structural isomers of isosqualene selected from the group consisting of compound B1, compound D, and compound A2. Some variations of the compositions comprise isosqualene and about 0.1-10% of one or more structural isomers of isosqualene. Some compositions comprise at least about 80%, 85%, or 90% isosqualene. Some compositions comprising at least about 80% isosqualene and 0.1-20% of the one or more structural isomers of isosqualene.

Some compositions comprise at least about 90% isosqualene and about 0.1-10% of the one or more structural isomers of isosqualene. Some variations of the compositions comprise at least about 10% of any one of or any combination of compound B1, compound D, and compound A2. Some variations of the compositions comprise about 50%, 55%, 60%, 65%, 70%, 75%, 80%, 85%, or 90% isosqualene and at least about 10% of any one of or any combination of compound B1, compound D, and compound A2.

Methods

In certain embodiments, methods provided herein comprise (a) catalytic dimerization of β-farnesene to obtain isosqualene, and (b) hydrogenation of isosqualene to obtain squalane. The catalytic dimerization and hydrogenation reactions can be schematically represented as follows:

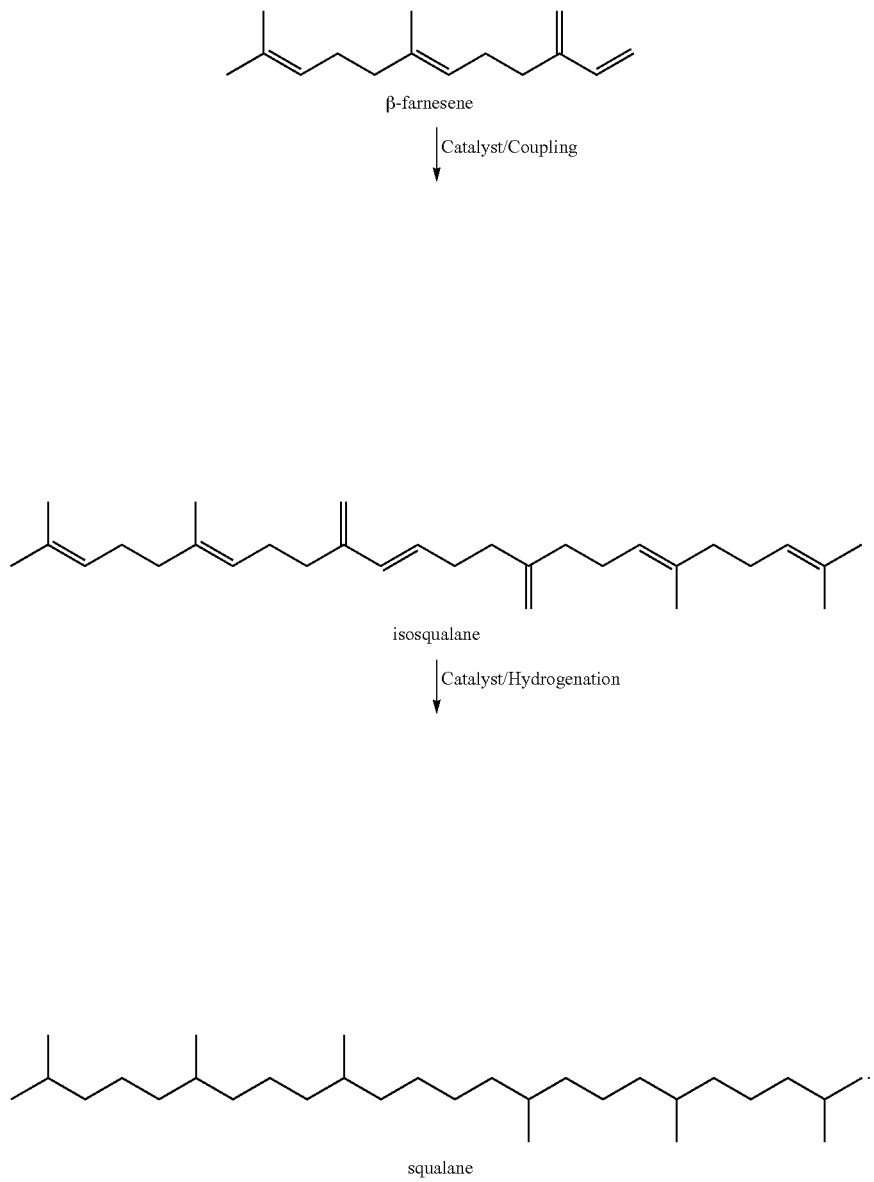

Although not shown in Scheme 1, the catalytic dimerization of β-farnesene may produce one or more structural isomers of isosqualene in addition to isosqualene, or instead of isosqualene. The particular structural isomers of isosqualene and the relative and absolute quantities of isosqualene and isosqualene structural isomers that are produced may depend on the type of catalyst used and on the catalysis conditions, such as catalyst precursor, catalyst loading and/or substrate to catalyst (S/C) ratio. Some dimerization catalysts (e.g., palladium) produce predominantly squalane following hydrogenation, as shown below. Some dimerization catalysts (e.g., some nickel catalysts and some early transition metal Ziegler-Natta catalysts) produce predominantly isosqualane following hydrogenation, as shown below.

In certain embodiments, the dimerization reaction is conducted in the presence a palladium catalyst, a nickel catalyst, or a early transition metal (e.g., Ziegler-Natta) catalyst. In certain embodiments, the dimerization reaction provided herein results in about 10%, 20%, 30%, 40%, 50%, 60%, 70%, 80%, 85%, 90%, 92%, 94%, 95%, 96%, 97%, 98%, 99% or greater conversion of β-farnesene.

Palladium Dimerization Catalysts

In certain embodiments, preformed or in situ-generated palladium catalysts can be used to catalyze the dimerization of β-farnesene to form a reaction product comprising isosqualene and structural isomers of isosqualene, and the reaction product can be hydrogenated to form a composition comprising squalane and isosqualane, and in some variations, also neosqualane.

In certain embodiments, palladium catalysts can be used to catalyze the dimerization of β-farnesene to produce a hydrogenated reaction product comprising squalane and isosqualane, and in some cases squalane is the predominant product. In certain variations of the hydrogenated reaction product produced using a palladium catalyst, the ratio (quantity squalane):(quantity isosqualane) is 2:1 or greater, e.g., 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1. In certain embodiments, palladium catalysts can be used to catalyze the dimerization of β-farnesene to produce a hydrogenated reaction product comprising at least about 90% squalane and 0.1-10% isosqualane, at least about 90% squalane and 0.1-8% isosqualane, at least about 90% squalane and 0.1-5% isosqualane, at least about 91% squalane and 0.1-9% isosqualane, at least about 91% squalane and 0.1-5% isosqualane, at least about 92% squalane and 0.1-8% isosqualane, or at least about 92% squalane and 0.1-5% isosqualane.

In certain embodiments, palladium(II) acetylacetonate in the presence of a protic solvent (e.g., 2-propanol, ethanol or methanol) and a triphenyl phosphine ligand can be used to dimerize β-farnesene. In some embodiments, the substrate to catalyst ratio is in a range from about 50/1 to 1000/1, e.g., 50/1, 75/1, 100/1, 125/1, 250/1, 400/1, 500/1, 750/1, or 1000/1. In some embodiments, the substrate to catalyst ratio is in a range from about 250/1 to about 5000/1, e.g., about 250/1, 400/1, 500/1, 700/1, 750/1, 800/1, 900/1, 1000/1, 1100/1, 1250/1, 1500/1, 1750/1, 2000/1, 2500/1, 3000/1, 3500/1, 4000/1, 4500/1, or 5000/1. In certain embodiments, a molar ratio of triphenylphosphine:Pd catalyst is about 1.5 to about 3, e.g., about 1.5, 2.0, 2.5, 2.8 or 3.0. The dimerization may be carried out at a temperature of about 20° C.-100° C., e.g., at a temperature in a range from about 75° C. to about 100° C. In some embodiments, the catalyst is initiated (e.g., at a temperature in a range from about 75° C. to about 100° C.), and the dimerization reaction is allowed to proceed at a lower temperature (e.g., at a temperature in a range from about 20° C. to about 70° C.). In one variation of this dimerization reaction, the reaction is carried out in 2-propanol at about 80° C.-85° C. and the substrate to catalyst ratio is about 400/1 or higher, e.g., about 400/1, 500/1, 600/1, 700/1, 800/1, 900/1, 1000/1, 1100/1, 1250/1, 1500/1, 1750/1, 2000/1, 2500/1, 3000/1, 3500/1, 4000/1, 4500/1, or 5000/1. In certain embodiments (e.g., when the substrate to catalyst ratio is about 500/1 or greater), exposure of the reaction to air is minimized, e.g., by sparging with nitrogen gas, or by conducting under an inert atmosphere (e.g., nitrogen blanket). In certain variations, starting materials, e.g., β-farnesene, catalyst/ligand and/or solvent (e.g., isopropanol), are degassed or sparged with nitrogen prior to use to reduce exposure of the reaction to air. In some variations, the dimerization reaction is carried out in 2-propanol and the molar concentration of β-farnesene in the 2-propanol is in a range from about 1.5 mol/liter (total solution) to about 3.0 mol/liter, e.g., about 1.6, 1.8, 2.0, 2.2, 2.5, 2.75 or 3 mol/liter. In some variations, the dimerization reaction is carried out with a concentration of β-farnesene in 2-propanol of about 2.0-3.0 mol/liter solution (e.g., about 2.0-2.5 mol/liter), a substrate to catalyst ratio of about 400/1 or higher (e.g., about 400/1, 500/1, 600/1, 700/1, 800/1, 900/1, 1000/1, 1100/1, 1250/1, 1500/1, 1750/1, 2000/1, 2500/1, 3000/1, 4000/1, 4500/1, or 5000/1), and a ligand to catalyst ratio of about 1.5 to about 3.0 (e.g., about 1.5, 1.8, 2.0, 2.5, 2.8, or 3.0). In some variations, the dimerization reaction results in about 80% or greater conversion of β-farnesene, e.g., about 80%, 85%, 90%, or 95% conversion. The dimerization reaction product may be hydrogenated to obtain a composition comprising squalane. The hydrogenation may be carried out using any suitable hydrogen catalyst as disclosed herein or otherwise known. For example a palladium catalyst (e.g., Pd/C) or a nickel catalyst can be used to hydrogenate the dimerization product. Palladium(II) acetylacetonate in the presence of protic solvent and triphenyl phosphine ligand may be used to prepare a squalane composition comprising squalane and isosqualane prepared by the methods described herein, e.g., wherein a ratio (quantity squalane):(quantity isosqualane) is at least about 14:1 (e.g., 14:1, 15:1, 16:1, 17:1, 18:1, 19:1, 20:1, 21:1, 22:1, 23:1, 24:1, 25:1, or 26:1). In some variations a squalane composition comprising squalane and isosqualane comprising at least about 80 area % squalane (e.g., at least about 80%, at least about 85%, or at least about 90%) is prepared. In some variations, a squalane composition comprising squalane and isosqualane comprising about 92-93 area % squalane and about 4-5 area % isosqualane is prepared. For example, a dimerization reaction of β-farnesene using Pd(acac)$_2$ with a triphenylphosphine ligand in 2-propanol (e.g., at a molar concentration of about 1.5 to 3.0 mol β-farnesene/total volume solution) at a substrate to catalyst ratio of about 400/1 or higher (e.g., about 400/1, 500/1, 600/1, 700/1, 800/1, 900/1, 1000/1, 1100/1, 1250/1, 1500/1, 1750/1, 2000/1, 2500/1, 3000/1, 3500/1, 4000/1, 4500/1 or 5000/1) and a ligand to catalyst ratio of about 1.5 to 3.0 (e.g., 1.5, 1.8, 2.0, 2.5, 2.8, or 3.0) may produce a squalane composition comprising squalane and isosqualane comprising 92-93 area % squalane and about 4-5 area % isosqualane.

In certain embodiments, the catalytic dimerization is conducted in the presence of a palladium catalyst. In certain embodiments, the catalyst used herein is formed from a palladium precursor selected from [Pd(allyl)Cl]$_2$, Pd(cod)Cl$_2$, [Pd(allyl)Cl]$_2$, Pd(cod)Cl$_2$, Pd$_2$(dba)$_3$, Pd(dba)$_2$, Pd(dba), Pd(acac)$_2$, or an equimolar mixture of Pd(dba)$_3$ and Pd$_2$(dba)$_3$. In certain embodiments, the resulting catalyst comprises a phosphine ligand. In certain embodiments, the phosphine ligand is selected from triphenyl phosphine, triethyl phosphine and tritolyl phosphine. Hydrogenated dimerization products resulting from these catalyst systems may be squalane compositions comprising squalane and isosqualane, wherein a ratio of (quantity squalane):(quantity isosqualane) is in a range from about 2:1 to about 26:1, e.g., 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1 or 26:1.

In certain embodiments, the catalytic dimerization is conducted in the presence of a palladium carbene. Various pre-catalyst systems known to one of skill in the art can be used to generate the active palladium carbene. In certain embodiments, the pre-catalyst system used to generate the active palladium carbene include 1,3-bis(2,6-diisopropylphenyl)-imidazol-2-ylidene-palladium(0)-$\eta^2,\eta^2$-1,1,3,3-tetramethyl-1,3-divinyl-disiloxane or Pd(0) (IPr) (dvds); 1,3-bis(2,6-diisopropylphenyl)-dihydroimidazol-2-ylidene-palladium(0)-$\eta^2,\eta^2$-1,1,3,3-tetramethyl-1,3-divinyl-disiloxane or Pd(0)(SIPr) (dvds); 1,3-dimesitylimidazol-2-ylidene-palladium(0)-$\eta^2,\eta^2$-1,1,3,3-tetramethyl-1,3-divinyl-disiloxane or Pd(0) (IMes) (dvds); 1,3-dimesityl-dihydroimidazol-2-ylidene-palladium(0)-$\eta2,\eta2$-1,1,3,3-tetramethyl-1,3-divinyl-disiloxane or Pd(0) (SIMes) (dvds); 1,3-bis(2,6-diisopropylphenyl)-4,5-dimethylimidazol-2-ylidene-palladium(0)-$\eta^2,\eta^2$-1,1,3,3-tetramethyl-1,3-divinyl-disiloxane or Pd(0) Me$_2$IPr (dvds); 1,3-bis(2,6-diisopropylphenyl)-4,5-dimethyl-dihydroimidazol-2-ylidene-palladium(0)-$\eta^2,\eta^2$-1,1,3,3-tetramethyl-1,3-divinyl-disiloxane or Pd(0) Me$_2$SIPr (dvds); 1,3-dimesityl-4,5-dimethylimidazol-2-ylidene-palladium(0)-$\eta^2,\eta^2$-1,1,3,3-tetramethyl-1,3-divinyl-disiloxane or Pd(0) Me$_2$IMes (dvds); 1,3-dimesityl-4,5-dimethyl-dihydroimidazol-2-ylidene-palladium(0)-$\eta^2,\eta^2$-1,1,3, 3-tetramethyl-1,3-divinyl-disiloxane or Pd(0) Me$_2$SIMes (dvds); 1,3-dimesityl-4,5-dichloroimidazol-2-ylidene-palladium(0)-$\eta^2\eta^2$-1,1,3,3-tetramethyl-1,3-divinyl-disiloxane or Pd(0) Cl$_{21}$Mes (dvds). In certain embodiments, the catalyst systems have one N-heterocyclic carbene (NHC) ligand and a weakly bound diene such as diallyl ether or hepta-1,6-diene). In certain embodiments, the catalyst system includes Pd(0)(NHC)$_2$ complexes. In certain embodiments, the catalyst system includes Pd(0) olefin complexes, where olefin is, for example, dimethyl fumarate, p-benzoquinone or naphthoquinone. In certain embodiments, the catalyst systems include 1,3-bis(2,6-diisopropylphenyl)imidazol-2-ylidene(1,4-naphthoquinone)palladium(0) dimer [(IPr)Pd(NQ)]2; or naphthoquinone-[1,3-bis(mesityl)imidazol-2-ylidene]palladium(0) dimer [(IMes)Pd(NQ)]$_2$. In certain embodiments, the catalyst systems include Pd (II) Cl, $\eta$-3-allyl (NHC) complexes. In certain embodiments, the catalyst systems include allylchloro-[1,3-bis-(2,6-diisopropylphenyl)-2-imidazolinidinylidene]palladium(II) [(SIPr)Pd(allyl)Cl]; allylchloro-[1,3-bis-(2,6-diisopropylphenyl)-imidazol-2-ylidene]palladium(II) [(IPr)Pd(allyl)Cl]; allylchloro-[1,3-bis-(mesityl)-imidazol-2-ylidene]palladium(II) [(IMes)Pd(allyl)Cl]; phenylallylchloro-[1,3-bis(2,6-diisopropylphenyl)imidazol-2-ylidene]palladium(II) [(IPr)Pd(cinnamyl)Cl]; or phenylallylchloro-[1,3-bis(2,6-diisopropylphenyl)-2-imidazolidinylidene]palladium(II) [(SIPr)Pd(cinnamyl)Cl].

In certain embodiments, a stable palladium carbene is formed by reacting a palladium precursor such as Pd(acac)$_2$ with an imidazolium salt, in some variations in the presence of a base (e.g., an alkoxide). In certain embodiments, the imidazolium salt is selected from salts described in U.S. Patent Publ. No. 2010/0160683, entitled "Process for Production of 2-(Substituted Phenyl)-3,3,3-Trifluoropropene Compound" and published Jun. 24, 2010, which is incorporated by reference herein in its entirety. In certain embodiments, a palladium carbene is formed by reacting a palladium precursor such as Pd(acac)$_2$ with a free carbene. In certain embodiments, a free carbene for use includes 1,3-bis-(2,6-diisopropylphenyl)-4,5-dihydroimidazol-2-ylidene (SIPr) or 1,3-bis-(mesityl)-4,5-dihydroimidazol-2-ylidene (SIMes). In certain embodiments, imidazolium salts or imidazolinium (i.e., dihydroimidazolium) salts for use herein include any imidazolium salt and dihydroimidazolium salt suitable for in situ generation of palladium carbenes. In certain embodiments, imidazolium or imidazolinium (i.e., dihydroimidazolium) salts are salts of 1,3-bis(mesityl)-4,5-dimethylimidazolium; 1,3-bis(mesityl)-4,5-dimethylimidazolinium; 1,3-bis(2,6-diisopropylphenyl)-4,5-dimethylimidazolinium; 1,3-bis(2,6-diisopropylphenyl)-4,5-dimethylimidazolinium; 1,3-bis(mesityl)-4,5-dichlorolimidazolium; 1,3-bis-(mesityl) imidazolium; 1,3-bis-(2,6-diisopropylphenyl)imidazolium; 1,3-bis-(adamantly)imidazolium; 1,3-bis-(cyclohexyl)imidazolium; 1,3-bis-(2,6-dimethylphenyl)imidazolium; 1,3-bis-(tolyl)imidazolium; dispiro(cyclohexane-1,3'(2'H)-imidazo(5,1-b:4,3-b')bisoxazol(4)ium-7'(8'H),1"-cyclohexane); 1,3-bis-(mesityl)-4,5-dihydroimidazolium; 1,3-bis-(2,6-diisopropylphenyl)-4,5-dihydroimidazolium; 1,3-bis-(adamantyl)-4,5-dihydroimidazolium; 1,3-bis-(cyclohexyl)-4,5-dihydroimidazolium; 1,3-bis-(2,6-dimethylphenyl)-4,5-dihydroimidazolium; or 1,3-bis-(tolyl)-4,5-dihydroimidazolium.

In certain embodiments, imidazolium salts or imidazolinium (i.e., dihydroimidazolium) salts for use herein include, but are not limited to 1,3-bis(mesityl)-4,5-dimethylimidazolium chloride; 1,3-bis(mesityl)-4,5-dimethylimidazolinium chloride; 1,3-bis(2,6-diisopropylphenyl)-4,5-dimethylimidazolium chloride; 1,3-bis(2,6-diisopropylphenyl)-4,5-dimethylimidazolinium chloride; 1,3-bis(mesityl)-4,5-dichlorolimidazolium chloride; 1,3-bis-(mesityl)imidazolium chloride (IMes.HCl); 1,3-bis-(2,6-diisopropylphenyl)imidazolium chloride (IPr.HCl); 1,3-bis-(adamantly)imidazolium chloride (IAd.HCl); 1,3-bis-(cyclohexyl)imidazolium chloride (ICy.HCl); 1,3-bis-(2,6-dimethylphenyl)imidazolium chloride (IXy.HCl); 1,3-bis-(tolyl)imidazolium chloride (ITol.HCl); dispiro(cyclohexane-1,3'(2'H)-imidazo(5,1-b:4,3-b')bisoxazol(4)ium-7'(8'H),1"-cyclohexane)trifluoromethanesulfonic acid salt (IBiox6.HOTf); 1,3-bis-(mesityl)-4,5-dihydroimidazolium chloride (SIMes.HCl); 1,3-bis-(2,6-diisopropylphenyl)-4,5-dihydroimidazolium chloride (SIPr.HCl); 1,3-bis-(adamantyl)-4,5-dihydroimidazolium chloride (SIAd.HCl); 1,3-bis-(cyclohexyl)-4,5-dihydroimidazolium chloride (SICy.HCl); 1,3-bis-(2,6-dimethylphenyl)-4,5-dihydroimidazolium chloride (SIXy.HCl); 1,3-bis-(tolyl)-4,5-dihydroimidazolium chloride (SITol.HCl); 1,3-bis-(mesityl)-4,5-dihydroimidazolium tetrafluoroborate (SIMes.HBF$_4$); 1,3-bis-(2,6-diisopropylphenyl)-4,5-dihydroimidazolium tetrafluoroborate (SIPr.HBF$_4$); 1,3-bis-(adamantyl)-4,5-dihydroimidazolium tetrafluoroborate (SIAd.HBF$_4$); 1-(2,6-Diisopropropylphenyl)-3-(2,4,6-trimethylphenyl)-imidazolinum chloride; 2-(2,6-Diisopropylphenyl)-5-methylimidazo[1,5-a]pyridinium hexafluorophosphate; 2-Mesityl-5-methylimidazo[1,5-a]pyridinium chloride; 1-(1-Adamantyl)-3-(2,4,6-trimethylphenyl)imidazolinium chloride; 1,3-Di-tert-butylimidazolinium tetrafluoroborate; 1,3-Di-tert-butylimidazolium tetrafluoroborate; or 4,5-dimethyl-1,3-bis-(2,6-diisopropylphenyl)imidazolium tetrafluoroborate. In certain embodiments, the imidazolium salt is 1,3-bis-(2,6-diisopropylphenyl)-4,5-dihydroimidazolium tetrafluoroborate. In certain embodiments, a mixture of a palladium precursor (e.g., Pd(acac)$_2$ or any other suitable palladium precursor) and an imidazolium salt (e.g., 1,3-bis-(2,6-diisopropylphenyl)-4,5-dihydroimidazolium tetrafluoroborate or any other suitable imidazolium salt) or an imidazolinium salt in the presence of a base (e.g., an alkoxide such as sodium isopropoxide) is used to catalyze dimerization of β-farnesene, e.g., to produce a composition that when hydrogenated comprises a composition having a squalane:isosqualane ratio of about 0.2:1, 0.4:1, 1:1, 5:1, 10:1 or 20:1. In certain embodiments, a mixture of a palladium precursor (e.g., Pd(acac)$_2$ or any other suitable palladium precursor) and a free carbene (e.g., SIPr or SIMes) is used to catalyze dimerization of β-farnesene, e.g., without a base such as an alkoxide. In certain dimerization reactions catalyzed by a palladium carbene (e.g., formed by a mixture of a palladium precursor such as Pd(acac)$_2$ and an imidazolium salt, in some variations in the presence of a base), a shorter reaction time (e.g., shorter than about 10-12 h) may favor production of isosqualane over squalane in the hydrogenated reaction product and may exhibit reduced tendency to form trimers and tetramers and/or overall increased dimer yield, e.g., as demonstrated by Examples 17a-17b herein.

In certain embodiments, the substrate to catalyst ratio (S/C) or catalyst loading with triphenyl phosphine ligand is 125/1, 250/1, 400/1, 500/1, 750/1, 1000/1, 1250/1, 1500/1, 1750/1, 2000/1, 2500/1, 3000/1, 3500/1, 4000/1, 4500/1, or 5000/1. In certain embodiments, the substrate to catalyst ratio (S/C) or catalyst loading with triphenyl phosphine ligand is 125/1, 250/1, 400/1, 500/1, 750/1, 800/1, 900/1, 1000/1, 1250/1, 1500/1, 1750/1 or 2000/1. In certain embodiments, the catalytic loading with triethyl phosphine ligand is 125/1, 250/1, 500/1, 750/1, 1000/1, 1250/1, 1500/1, 1750/1, 2000/1, 2500/1, 3000/1, 3500/1, 4000/1, 4500/1, or 5000/1. In certain embodiments, the catalytic loading with tritolyl phosphine ligand is S/C 125/1, 250/1, 500/1, 750/1, 1000/1, 1250/1, 1500/1, 1750/1, 2000/1, 2500/1, 3000/1, 3500/1, 4000/1, 4500/1, or 5000/1. In certain embodiments (e.g., when the substrate to catalyst ratio is about 500/1 or greater), exposure of the reaction to air is minimized, e.g., by sparging with nitrogen gas, or by conducting under an inert atmosphere (e.g., nitrogen blanket). In certain variations, starting materials, e.g., β-farnesene, catalyst/ligand and/or solvent (e.g., isopropanol), are degassed or sparged with nitrogen prior to use to reduce exposure of the reaction to air.

In certain embodiments, the substrate to catalyst ratio (S/C) or catalyst loading with carbene ligand is S/C 500/1; 1000/1; 2000/1; 3000/1; 4000/1; 5000/1; 7000/1; 10,000/1; 25,000/1; 50,000/1; 75,000/1; 100,000/1; 150,000/1 or 200,000/1.

In certain embodiments, the dimerization reaction is conducted in the presence of a protic solvent. In certain embodiments, the protic solvent comprises a primary or a secondary alcohol. In certain embodiments, the protic solvent is isopropyl alcohol. In certain embodiments, the protic solvent is n-propanol, n-butanol, 2-butanol, 3-methyl-2-butanol, or t-butanol.

In certain embodiments, one or more equivalents of the ligand for each mole of the catalyst precursor are used in the dimerization reaction. In certain embodiments, about one, two, three, four or five equivalents of the ligand for each mole of the catalyst precursor are used in the dimerization reaction. In certain embodiments, about two to four equivalents of the ligand for each mole of the catalyst precursor are used in the dimerization reaction. In certain embodiments, about one equivalent of the ligand for each mole of the catalyst precursor is used in the reactions herein. In certain embodiments, about two equivalents of the ligand for each mole of the catalyst precursor are used in the reactions herein.

In certain embodiments, a palladium catalyst comprises (i) a palladium complex selected from [Pd(allyl)Cl]$_2$, Pd(cod)Cl$_2$, Pd$_2$(dba)$_3$, Pd(dba)$_2$, Pd(dba), Pd(acac)$_2$, or an equimolar mixture of Pd(dba)$_3$ and Pd$_2$(dba)$_3$; and (ii) a triphenyl phosphine ligand, wherein the catalysis comprises one to four equivalents of the ligand for each mole of the palladium complex, or wherein the catalyst comprises one or two equivalents of the ligand for each mole of the palladium complex.

In certain embodiments, the dimerization is carried out in the presence of a base or a reducing agent in order to generate Pd(0) from the preformed palladium catalyst. In certain embodiments, the reducing agent or base is sodium formate. In certain embodiments, sodium formate is used in an amount from about 15 mol % to about 50 mol %. In certain embodiments, sodium formate is used in amount of about 15, 20, 25, 30, or 40 mol %. In certain embodiments, sodium formate is used in about 20 mol %. In certain embodiments, the base or reducing agent is sodium isopropoxide, sodium ethoxide, sodium borohydride, or hydrogen gas. In certain embodiments, the dimerization is carried out without any reducing agent or base other than a protic solvent. In certain variations, the dimerization is carried out in a protic solvent such as isopropanol, methanol, or ethanol, where the protic solvent may function as a reducing agent.

In certain embodiments, the catalyst used in the dimerization reaction is Pd(cod)Cl$_2$/2 PPh$_3$, or Pd(PPh$_3$)$_2$Cl$_2$. In certain embodiments, the catalytically active species can be generated in-situ by contacting Pd(cod)Cl$_2$ with a monodentate phosphine in the presence of about 20 mol % of NaHCO$_2$. In certain embodiments, Pd(PPh$_3$)$_2$Cl$_2$ can be used with about 20 mol % of HCO$_2$Na in the dimerization reaction.

In certain embodiments, the catalytic loading ratio with triethyl phosphine ligand is about 125/1, 250/1 or 500/1. In some embodiments, the substrate to catalyst ratio is in a range from about 250/1 to about 5000/1, e.g., 250/1, 400/1, 500/1, 750/1, 1000/1, 1250/1, 1500/1, 1750/1, 2000/1, 2500/1, 3000/1, 3500/1, 4000/1, 4500/1 or 5000/1. In certain embodiments, the dimerization reaction is conducted in the presence of isopropyl alcohol, ethanol, or methanol. In certain embodiments, the dimerization reaction is conducted in the presence of a base or reducing agent such as sodium formate, sodium isopropoxide, sodium ethoxide, sodium borohydride, or hydrogen gas. In certain embodiments, the reaction is conducted in the presence of about 20 mol % sodium formate.

In certain embodiments (e.g., when the substrate to catalyst ratio is about 500/1 or greater), exposure of the reaction to air is minimized, e.g., by sparging with nitrogen gas, or by conducting under an inert atmosphere (e.g., nitrogen blanket). In certain variations, starting materials, e.g., β-farnesene, catalyst/ligand and/or solvent (e.g., isopropanol), are degassed or sparged with nitrogen prior to use to reduce exposure of the reaction to air.

In certain embodiments, the dimerization reaction is conducted at a temperature of about 20° C. to 110° C. In certain embodiments, the dimerization reaction is conducted at a temperature of about 75° C. to 110° C. In some embodiments, the dimerization reaction is conducted at a temperature of about 75° C. to 100° C., or about 70° C. to 90° C. In certain embodiments, the temperature is about 75-95° C. In certain embodiments, the temperature is about 75-90° C. In certain embodiments, the temperature is about 80-95° C. In certain embodiments, the temperature during the reaction is about 80, 85, 90 or 95° C. In certain embodiments, the reaction is initiated at an initial higher temperature (e.g., to form the catalytic species) and the dimerization reaction may proceed at a lower reaction temperature. For example, the reaction may be initiated at a temperature in a range from about 70° C. to about 110° C. (e.g., at a temperature from about 75° C. to about 90° C.), and following initiation, the reaction may proceed at a temperature lower than 70° C., e.g., at about 20° C. to about 50° C., or at room temperature.

Nickel Dimerization Catalysts

In certain embodiments, preformed or in situ-generated nickel catalysts can be used to catalyze the dimerization of β-farnesene to form a reaction product comprising isosqualene and structural isomers of isosqualene, and the reaction product can be hydrogenated to form a composition comprising squalane and isosqualane, and in some variations, also neosqualane. In certain cases, a nickel catalyst can be used to produce a hydrogenated reaction product in which squalane is the predominant product. In other cases, a nickel catalyst produces a hydrogenated reaction product in which the amounts of squalane and isosqualane are similar. In some situations, a nickel catalyst produces a hydrogenated reaction product in which isosqualane is the predominant product. In some variations, a nickel catalyst can be used to produce a hydrogenated reaction product in which the ratio (quantity isosqualane):(quantity squalane) is greater than 1, e.g., about 4:1 or about 5:1.

Any suitable nickel catalyst can be used to catalyze the dimerization of β-farnesene. In certain embodiments, the nickel catalyst used herein is selected from $Ni(cod)_2$, $Ni(PPh_3)_4$, $Ni(PPh_3)_2Cl_2$ and $Ni(acac)_2$. Any suitable ligand can be used with the nickel catalyst, e.g., $Ni(cod)_2$ can be used with $PhPCy_2$ or of $PCy_3$. In certain embodiments, the nickel catalyzed dimerization reaction yields a mixture of squalane, isosqualane and neosqualane after hydrogenation. In certain embodiments when a nickel catalyst is used, exposure of the reaction to air is minimized, e.g., by sparging with nitrogen gas, or by conducting under an inert atmosphere (e.g., nitrogen blanket).

Early Transition Metal Catalysts

In some cases, zirconium, titanium or hafnium catalysts can be used to catalyze the dimerization of β-farnesene to produce a reaction product that when hydrogenated comprises isosqualane and squalane, and in some cases, neosqualane. In some variations, an early transition metal catalyst (which may be a Ziegler Natta catalyst) produces a product that, when hydrogenated, gives isosqualane as the predominant product. In some variations, an early transition metal (e.g., Ziegler-Natta) catalyst can be used to produce a reaction product that, when hydrogenated, gives a composition in which the ratio (quantity isosqualane):(quantity squalane) is greater than 1, e.g., about 60:1, 30:1, 20:1, 8:1, or 7:1. In some variations, an early transition metal (e.g., Ziegler-Natta) catalyst can be used to produce a reaction product that, when hydrogenated, comprises isosqualane and less than about 2% squalane. In some variations, such early transition metal (e.g., Ziegler-Natta) catalysts can be used to catalyze the dimerization of β-farnesene to produce a reaction product that when hydrogenated comprises isosqualane, but about 2% or less squalane (wt %, vol %, or area %, e.g., as measured by GC-MS or GC-FID). In some variations, such early transition metal (e.g., Ziegler-Natta) catalysts can be used to catalyze the dimerization of β-farnesene to produce a reaction product that when hydrogenated comprises isosqualane and neosqualane, but about 2% or less squalane (wt %, vol %, or area %, e.g., as measured by GC-MS or GC-FID). In some variations, early transition metal (e.g., Ziegler-Natta) catalysts are used to catalyze the dimerization of β-farnesene in inert atmosphere (e.g., in a glove box).

For example, a homogeneous two component catalyst that comprises as a first component a zirconium, titanium or hafnium halide (e.g., $ZrCl_4$, $ZrBr_4$, $ZrCl_aBr_b$, $ZrI_4$, $TiCl_4$, or $HfCl_4$, where a+b=4 and a=1,2, or 3 and b=1, 2 or 3) or a zirconium alkoxide (e.g., $Zr(O-tBu)_4$ or $Zr(O-Et)_4$), and as a second component (co-catalyst) an alkyl metal catalyst, e.g., an alkyl aluminum catalyst selected from the group consisting of compounds $R_2AlX$, $RAlX_2$, $R_3Al_2X_3$ and $R_3Al$, where R is a C1-C20 alkyl group and X is Cl or Br, or a metal alkoxide catalyst such as an aluminum alkoxide (e.g., a methylaluminoxane, or having the formula $[AlOCH_3]_n$, where n=1-40, or having the formula $R^1{}_aAl(OR^2)_b(OR^3)_c$, where $R^1$, $R^2$, and $R^3$ are each individually C1-C20 alkyl groups, and a, b and c are each individually 0, 1, 2, or 3, and a+b+c=3). In some variations, the alkyl metal catalyst is triethyl aluminum, diethyl aluminum chloride, tri-n-octyl aluminum, or diethyl aluminum ethoxide. It should be noted that methylaluminoxanes may include small amounts of C2-C10 alkyl groups and such materials are included within the term "methylaluminoxane" or "methylaluminoxanes" as used herein.

Optionally, a ligand may be used with the first catalyst component. For example, a ligand such as $P(o-OMePh)_3$, $Ph_2PtBu$, $P(m-OMePh)_3$, Bipy, DPPE, $PCy_3$, or $PPh_3$ can be used.

Non-limiting examples of early transition metal (e.g., Ziegler-Natta) catalyst systems that can be used to dimerize β-farnesene are provided in Table 3A.

TABLE 3A

Non-limiting Examples of Early Transition Metal
(e.g., Ziegler-Natta) Catalyst Systems

| Catalyst | Ligand | Co-catalyst |
|---|---|---|
| $Zr(OtBu)_4$ | $PPh_3$ | $Et_2AlCl$ |
| $Zr(OtBu)_4$ | $P(o-OMePh)_3$ | $Et_2AlCl$ |
| $Zr(OtBu)_4$ | $P(m-OMePh)_3$ | $Et_2AlCl$ |
| $Zr(OtBu)_4$ | Bipy | $Et_2AlCl$ |
| $Zr(OtBu)_4$ | DPPE | $Et_2AlCl$ |
| $Zr(OtBu)_4$ | $PCy_3$ | $Et_2AlCl$ |
| $Zr(OtBu)_4$ | $PPh_3$ | $Et_2AlCl$ |
| $Zr(OtBu)_4$ | none | $Et_2AlCl$ |
| $Zr(OEt)_4$ | $PPh_3$ | $Et_3Al$ |
| $Zr(OEt)4$ | $PPh_3$ | $Et_2AlCl$ |
| $ZrCl_4$ | None | MAO |
| $ZrCl_4$ | None | $Oct_3Al$ |
| $ZrCl_4$ | None | $Et_2Al(O-Et)$ |
| $ZrCl_4$ | None | none |
| $ZrCl_4$ | None | $Et_2AlCl$ |
| $ZrCl_4$ | None | $Et_3$ |
| $TiCl_4$ | None | $Oct_3Al$ |

In certain variations, early transition metal (e.g., Ziegler-Natta) catalysts described herein produce trimers of β-farnesene. In certain variations, early transition metal (e.g., Ziegler-Natta) catalysts described herein produce tetramers of β-farnesene. In certain variations, early transition metal (e.g., Ziegler-Natta) catalysts described herein produce dimers and trimers of β-farnesene, or dimers, trimers and tetramers of β-farnesene. In certain circumstances, early transition metal (e.g., Ziegler-Natta) catalysts described herein produce higher order oligomers of β-farnesene, e.g., pentamers, hexamers, heptamers, etc.

In certain embodiments, the conversion rate and selectivity of the dimerization reaction herein depends on the catalyst used, including for example, the catalyst precursor, the ligand, the substrate to catalyst ratio (S/C), and/or the catalyst loading.

In certain embodiments, the dimerization reaction conducted in the presence of a palladium catalyst, a nickel catalyst, or an early transition metal (e.g., Ziegler-Natta) catalyst provided herein results in about 10%, 20%, 30%, 40%, 50%, 60%, 70%, 80%, 85%, 86%, 87%, 88%, 89%, 90%, 91%, 92%, 93%, 94%, 95%, 96%, 97%, 98%, 99% or greater conversion of β-farnesene.

In some embodiments of the methods provided herein, the reaction conditions and the catalyst for the dimerization reaction are selected such that the reaction proceeds to yield isosqualene as a major reaction product. In certain embodiments, the dimerization reaction provided herein proceeds with about 80%, 85%, 90%, 92%, 94%, 95%, 96%, 97%, or 98% or greater selectivity for isosqualene over the other products formed in the reaction.

In certain embodiments, the dimerization reaction provided herein results in about 80%, 81%, 82%, 83%, 84%, 85%, 86%, 87%, 88%, 89%, 90%, 91%, 92%, 93%, 94%, 95%, 96%, 97%, 98%, 99% or greater conversion of β-farnesene with about 80%, 81%, 82%, 83%, 84%, 85%, 86%, 87%, 88%, 89%, 90%, 91%, 92%, 93%, 94%, 95%, 96%, 97%, 98%, 99% or greater selectivity for isosqualene over the other products formed in the reaction. In certain embodiments, the dimerization reaction provided herein results in about 90% or greater conversion of β-farnesene with about 90% or greater selectivity for isosqualene over the other products formed in the reaction. In certain embodiments, the dimerization reaction provided herein results in about 95% or greater conversion of β-farnesene with about 95% or greater selectivity for isosqualene over the other products formed in the reaction. In certain embodiments, the dimerization reaction provided herein results in about 95% or greater conversion of β-farnesene with about 95-98% selectivity for isosqualene over the other products formed in the reaction.

In some embodiments of the methods provided herein, the reaction conditions and the catalyst for the dimerization reaction are selected such that the reaction proceeds to yield isosqualane as a major reaction product following hydrogenation. In certain embodiments, the dimerization reaction provided herein results in about 10%, 20%, 30%, 40%, 50%, 60%, 70%, 80%, 90% or greater conversion of β-farnesene with about 80%, 81%, 82%, 83%, 84%, 85%, 86%, 87%, 88%, 89%, 90%, 91%, 92%, 93%, 94%, 95%, 96%, 97%, 98%, 99% or greater selectivity for isosqualane over the other products formed in the hydrogenated reaction products.

In certain embodiments, the dimerization reaction product can contain one or more of compound A2, compound B1, compound DA1, compound DA2 or compound D as represented below:

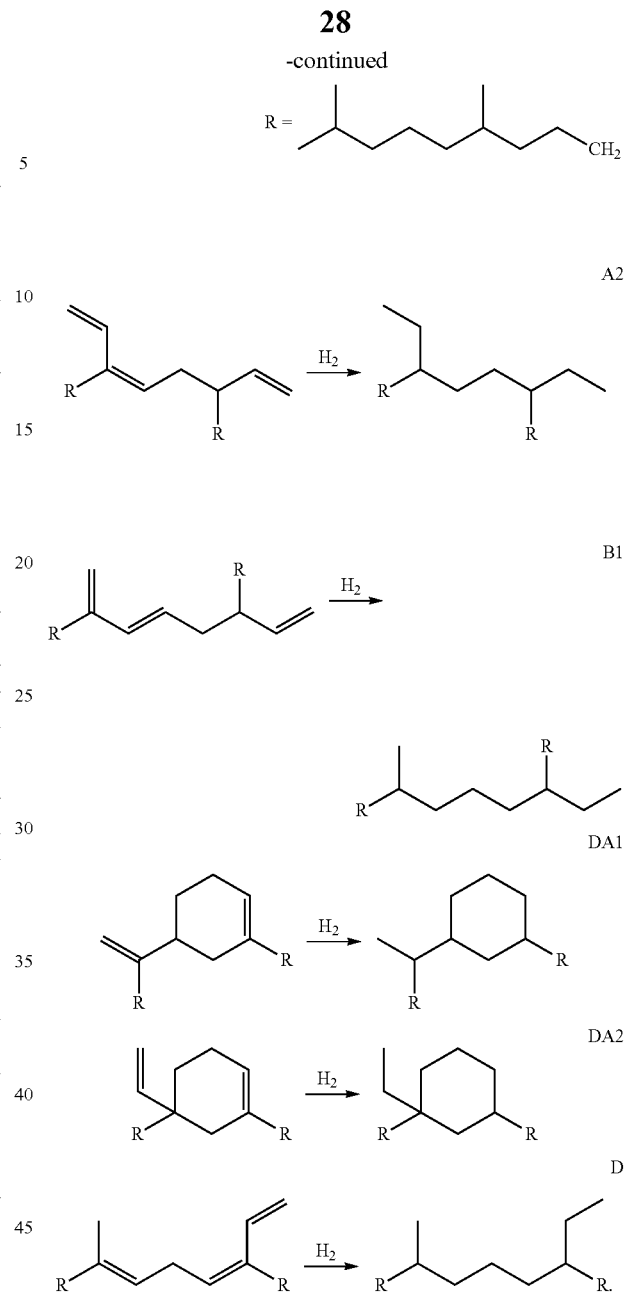

In certain embodiments, the dimerization reaction product can contain one or more double bond isomers of compound A2, compound B2, compound DA1, compound DA2, or compound D.

In certain embodiments, the products in the dimerization reaction can be formed by a coupling mechanism represented in Scheme 2.

Scheme 2:

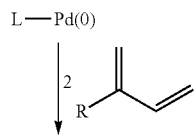

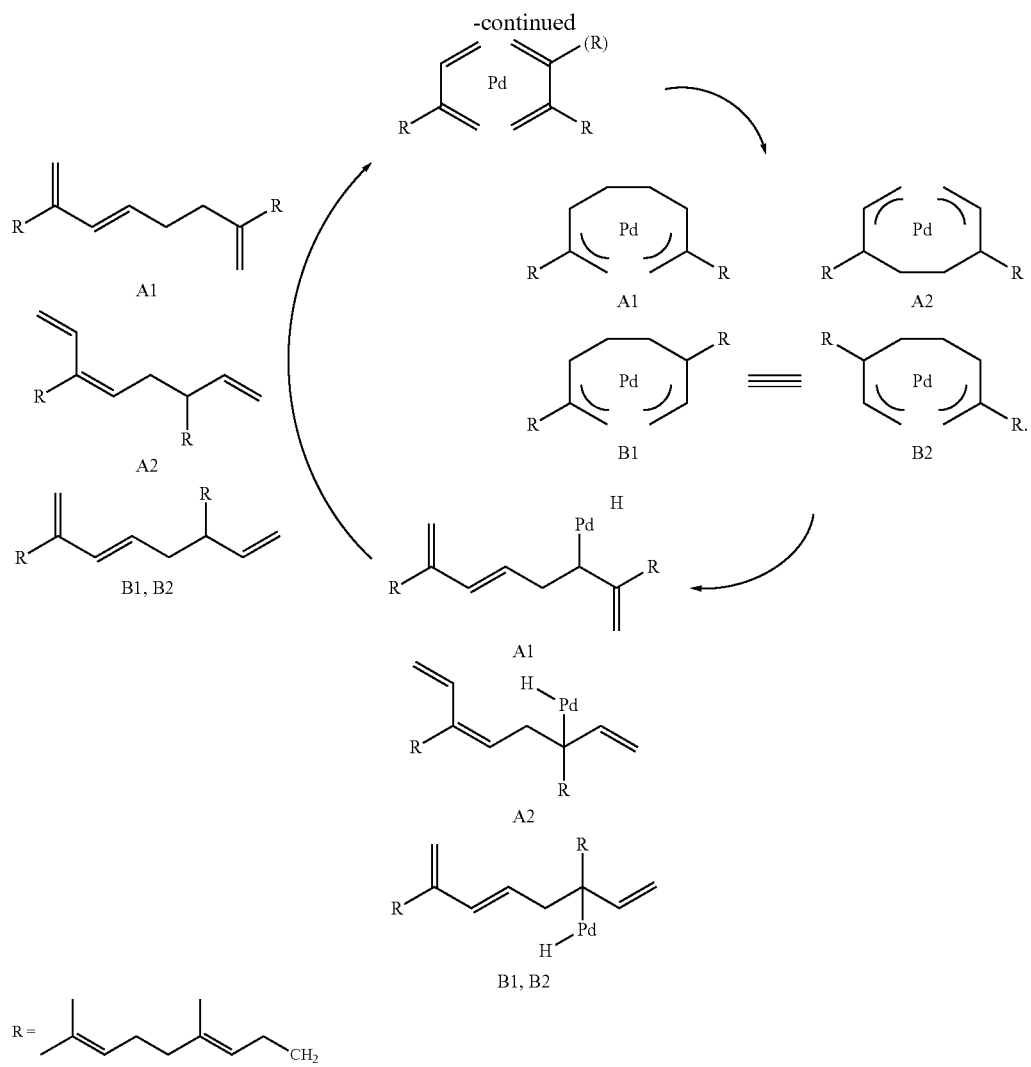

In certain embodiments of the methods provided herein, isosqualene prepared by the dimerization reaction is hydrogenated to obtain squalane. In certain embodiments, isosqualene can be hydrogenated by any technique apparent to one of skill in the art. In certain embodiments, the hydrogenation reaction can be carried out in the presence of hydrogen with a catalyst such as Pd, Pd/C, Pt, $PtO_2$, $Ru(PPh_3)_3Cl_2$, $Rh(PPh_3)_3$, Ru/C, Raney nickel, nickel, or combinations thereof. The hydrogenation reaction can be carried out as known to one of skill in the art, for example, as reported in International Patent Publication No. WO 2010/042208, which is incorporated herein by reference herein in its entirety. In certain embodiments, the hydrogenation catalyst is a Pd catalyst. In another embodiment, the hydrogenation catalyst is 5 wt % Pd/C or 10 wt % Pd/C. In certain embodiments, the hydrogenation catalyst is a nickel catalyst, such as 21% $Ni/Al_2O_3$, or a nickel powder catalyst, such as a powder catalyst comprising about 60 wt % nickel (e.g., PRICAT Ni 62/15 P catalyst, available from Johnson Matthey). In some cases, a hydrogenation catalyst is used in a fixed bed reactor, e.g., with a 21% $Ni/Al_2O_3$ catalyst. In some cases, a hydrogenation catalyst is used in a batch slurry mode. Alternatively, any reducing agent that can reduce a C=C bond to a C—C bond can also be used.

In certain embodiments, the hydrogenation reaction is carried out in the presence of 5 wt % Pd/C, e.g., with a loading of about 0.1 mol % to about 0.25 mol %. In certain embodiments, the hydrogenation reaction is carried out at about 35-75° C. In certain embodiments, the hydrogenation reaction is carried out at about 120° C.-160° C. under about 50 psig to 1000 psig (or about 3 bar to 70 bar) hydrogen. In certain variations, the reaction temperature is controlled by cooling to maintain the temperature between about 150° C.-160° C. The completeness of the hydrogenation can be determined using iodine value or bromine index. In some variations, a bromine index of 200 mg per 100 g sample or less indicates complete hydrogenation.

In certain embodiments, the hydrogenated reaction product may be filtered to remove and recover the hydrogenation catalyst. For example, the hydrogenated reaction product may be filtered through a silica or alumina plug. In some cases, the hydrogenated reaction product may be filtered more than once (e.g., twice) to remove observable particulates. In some cases in which the dimerization reaction yields byproducts that are oxygenated or polar, the hydrogenated reaction product may be filtered through a filter capable of removing relatively polar compounds or oxygenated compounds, e.g., a silica filter. For example, if a phosphine ligand is used in the dimerization reaction, a silica filter may be used to remove oxygenated by products of the phosphine ligand.

In certain embodiments, the hydrogenated reaction product is distilled to remove lower molecular weight components (e.g., farnesane, farnesol, or other hydrocarbons having 15 carbons or less), and to remove higher molecular weight species (e.g., components having molecular weight corresponding to hydrocarbons having 45 carbons and above). For example, distillation can be conducted in wiped-film distillation apparatus. In some variations, a two pass distillation procedure can be performed, with a first pass to remove lower molecular weight components (e.g., farnesane and other hydrocarbons having 15 carbons or less) and a higher temperature, stronger vacuum second pass to separate the reaction product from the heavier molecular weight components (e.g., hydrocarbons having 45 carbons or more). For example, a first distillation pass can be conducted at 173° C. under 25 Torr vacuum with a rate of 20-25 g/min and a second distillation pass may be conducted at 265° C. under 1 Torr vacuum with a rate of 20-25 g/min. In some variations, a first distillation pass may be conducted at 165° C. under 1 torr vacuum and a second distillation pass may be conducted at 265° C. under 1 torr vacuum. In some variations, the hydrogenated reaction product can be further filtered using any suitable filtration technique and filtration medium, e.g., using an alumina filter, or a silica filter. In some variations, the hydrogenated reaction product is further filtered to remove oxygenates.

In certain embodiments, the methods provided herein yield squalane as a major product and isosqualane as a minor product after hydrogenation. In certain embodiments, the methods provided herein yield squalane as the major product and isosqualane and neosqualane as minor products. In certain embodiments, the methods provided herein yield isosqualane as a major product. In certain embodiments, the methods provided herein yield isosqualane as a major product and squalane and/or neosqualane as minor products.

Disclosed herein are methods for making a composition comprising squalane and isosqualane, wherein the relative quantities of squalane and isosqualane in the composition can be selected by appropriate selection of the dimerization catalyst. In some embodiments, the methods comprise catalytically dimerizing β-farnesene to produce a composition comprising squalane and isosqualane, wherein the catalyst has been selected to produce a desired ratio (quantity squalane):(quantity isosqualane), e.g., selecting a catalyst to produce a (squalane):(isosqualane) ratio of about 0.01:1, 0.1:1, 0.5:1, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 26:1. In some variations, the methods comprise selecting the catalyst to produce predominantly squalane, and in certain variations, squalane having a purity of about 80% or greater (e.g., 80%, 85%, 88%, 90%, 92%, or 93%) can be achieved. In some variations, the catalyst can be selected to produce predominantly isosqualane, and in certain variations, isosqualane having a purity of greater than about 80% (e.g., 80%, 85%, 88%, 90%, 92%, or 95%) can be achieved.

In certain embodiments, the methods for making a composition comprising squalane and isosqualane (e.g., using a palladium, palladium carbene, nickel or zirconium catalyst) produce a composition having a (quantity squalane):(quantity isosqualane) ratio between about 1:60 and about 14:1 or between about 1:60 and 10:1. In some embodiments, the (quantity squalane):(quantity isosqualane) ratio is between about 1:60 and 1:4. In some embodiments, the (quantity squalane):(quantity isosqualane) ratio is between about 1:60 and 1:7. In some embodiments, the (quantity squalane): (quantity isosqualane) ratio is between about 1:1 and 14:1. In some embodiments, the (quantity squalane):(quantity isosqualane) ratio is between about 1:1 and 10:1 or between about 2:1 and 10:1.

Disclosed herein are methods for making a composition comprising squalane and isosqualane comprising blending a first composition comprising squalane with a second composition comprising isosqualane to produce a product comprising squalane and isosqualane in a desired ratio (quantity isosqualane):(quantity squalane).

In certain embodiments, β-farnesene used in the methods is derived from an isoprenoid starting material. In certain embodiments, the isoprenoid starting material is made by host cells by converting a carbon source into the isoprenoid starting material. Exemplary methods for making β-farnesene are described in U.S. Pat. No. 7,399,323 B1, entitled "Fuel compositions comprising farnesane and farnesane derivatives and method of making and using same," issued Jul. 15, 2008, which is incorporated by reference herein in its entirety.

Applications

Any one of the compositions disclosed herein may be useful in applications known to utilize squalane (e.g., synthetic squalane, or squalane derived from fish or vegetable sources.)

Personal Care Products

In certain embodiments, compositions described herein can be useful in preparation of personal care products, e.g., emollients or cosmetics such as several kinds of creams, especially nutrient creams and medicated creams, milky lotion, toilet lotion, lipstick, foundation, and face powder; as a fatting agent for high quality soap; for producing medical and pharmaceutical preparations such as ointments, suppositories and medical lubricating agent. For example, any composition disclosed herein comprising about 85%, 86%, 87%, 88%, 89%, 90%, 91%, 92%, 93%, 94%, 95%, 96%. 97%, or 98% (wt %, vol % or area %, e.g., by GC-MS or GC-FID) or greater squalane may be useful as emollients or cosmetics, or as components of emollient formulations or cosmetic formulations. In some variations, any composition disclosed herein comprising about 10% or more isosqualane (e.g., about 10%, 15%, 20%, 25%, 30%, 35%, 40%, 45%, 50%, 55%, 60%, 65%, 70%, 75%, 80%, 85%, 90%, 95% or 98% isosqualane, where % is measured as wt %, vol % or area %) may be useful as emollients or cosmetics or as components of emollient formulations or cosmetic formulations. Any of the compositions comprising squalane and/or isosqualane disclosed herein (e.g., any of the compositions disclosed in Tables 1A and 2A) may be useful as emollients or cosmetics, or as components of emollient formulations or cosmetic formulations. In certain variations, compositions useful in cosmetics or emollients may comprise neosqualane.

In certain embodiments, a composition comprising primarily squalane, primarily isosqualane, or a mixture of squalane and isosqualane prepared by the methods disclosed herein is used to replace squalane derived from other sources, e.g., from sharks or from olive oil, in a cosmetic or emollient. In certain embodiments, the total amount of squalane, isosqualane and neosqualane in an emollient or cosmetic composition is from about 1 wt % to about 95 wt % or greater, or from about 5 wt % to about 90 wt % or greater, based on the total weight of the composition. In certain embodiments, the total amount of squalane, isosqualane and neosqualane in emollient or cosmetic compositions provided herein is about 1, 3, 5, 7, 10, 12, 15, 17, 20, 23, 25, 27, 30, 33, 35, 37, 40, 43, 45, 47, 50, 60, 70, 80, 90, or 95 wt % or greater, based on the total weight of the composition.

In certain embodiments, a cosmetic or emollient, or a component in a cosmetic or emollient formulation, consists essentially of a product of any method for preparing squalane and/or isosqualane as provided herein.

Lubricant Compositions

In certain embodiments, any of the compositions disclosed herein comprising squalane and/or isosqualane, or any of the compositions disclosed herein comprising squalane, isosqualane and/or neosqualane may have applications as a lubricant composition or as a component in a lubricant composition. Lubricant compositions encompass lubricant base stocks, lubricant base oils, lubricant additives, lubricants, and lubricant formulations. Any of the compositions comprising squalane and/or isosqualane disclosed herein (e.g., any of the compositions disclosed in Tables 1A and 2A) may be used as a lubricant base stock, a lubricant base oil, a lubricant additive, a lubricant, or as a component in a finished lubricant formulation.

In certain variations, compositions comprising squalane and isosqualane wherein isosqualane is present in at least about 10% are useful in lubricant applications, e.g., any of the compositions disclosed in Tables 1A and 2A wherein isosqualane is present at about 10%, 15%, 20%, 25%, 30%, 35%, 40%, 45%, 50%, 55%, 60%, 65%, 70%, 75%, 80%, 85%, 90%, 95% or 98%.

In some variations, compositions comprising trimers or tetramers of β-farnesene are useful as lubricants. Isosqualane as made by the methods described herein (and comprising about 1% trimer) has a viscosity index of about 102-115 and a composition comprising 92% squalane and 4-5% isosqualane made by the methods described herein has a viscosity index of about 116-125, e.g., about 122. In certain variations, e.g., where higher viscosities are desired, it may be desirable to utilize trimers and/or tetramers of β-farnesene, e.g., as can be made using certain early transition metal (e.g., Ziegler-Natta) catalysts described herein as a base oil, as a component in a base oil, or as a component in a lubricant formulation.

In certain embodiments, the total amount of squalane, isosqualane and neosqualane in lubricant compositions provided herein is about 1 wt % or greater based on the total weight of the lubricant composition. In certain embodiments, the total amount of squalane, isosqualane and neosqualane in lubricant compositions provided herein is from about 1 wt % to about 95 wt % or greater, or from about 5 wt % to about 90 wt % or greater, based on the total weight of the composition. In certain embodiments, the total amount of squalane, isosqualane and neosqualane in compositions provided herein is about 1, 3, 5, 7, 10, 12, 15, 17, 20, 23, 25, 27, 30, 33, 35, 37, 40, 43, 45, 47, 50, 60, 70, 80, 90, or 95 wt % or greater, based on the total weight of the lubricant composition.

In certain embodiments, the combined amount of squalane and isosqualane in lubricant compositions provided herein is about 1 wt % or greater based on the total weight of the lubricant composition. In certain embodiments, the total amount of squalane and isosqualane in compositions provided herein is from about 1 wt % to about 95 wt % or greater, or from about 5 wt % to about 90 wt % or greater, based on the total weight of the composition. In certain embodiments, the total amount of squalane and isosqualane in compositions provided herein is about 1, 3, 5, 7, 10, 12, 15, 17, 20, 23, 25, 27, 30, 33, 35, 37, 40, 43, 45, 47, 50, 60, 70, 80, 90, or 95 wt % or greater, based on the total weight of the composition.

In certain embodiments, the compositions comprising squalane and/or isosqualane provided herein can be used as base stocks or base oils, e.g., a base stock or base oil having a kinetic viscosity of about 4-5 cSt at 100° C. For example, any composition disclosed in Table 1A or in Table 2A can be used as a base stock or base oil. Base stock and base oil compositions include but are not limited to: a composition comprising at least about 88% squalane, and about 0.1-12% isosqualane; a composition comprising at least about 88% squalane, and about 0.1-5% isosqualane; a composition comprising at least about 90% squalane, and about 0.1-10% isosqualane; a composition comprising at least about 90% squalane and about 0.1-5% isosqualane; a composition comprising at least about 92% squalane and about 0.1-8% isosqualane; and a composition comprising at least about 92% squalane and about 0.1-5% isosqualane (% measured as wt %, vol % or area % of the total base oil composition). In some variations, a base stock or base oil comprises isosqualane and squalane, and the quantity of isosqualane is comparable to or greater than the quantity of squalane. Non-limiting examples of such base stock or base oil compositions are provided in Table 2A. For example, in some cases, the quantity of isosqualane in a base stock or base oil is about 90% or greater, e.g., at least about 90%, at least about 92%, at least about 94%, or at least about 96% (% measured as wt %, vol %, or area %).

In a certain embodiment, the lubricant base oil provided herein consists essentially of a product of any method for preparing squalane and/or isosqualane as provided herein.

In certain embodiments, the lubricant compositions (e.g., base oils or base stocks) provided herein have kinetic viscosity of about 3 centistokes (cSt) or greater at 100° C. In certain embodiments, the lubricant compositions (e.g. base oils or base stocks) provided herein have kinetic viscosity of about 4 centistokes (cSt) or greater at 100° C. In certain embodiments, the lubricant compositions provided herein have kinetic viscosity from about 3 cSt to about 10 cSt, from about 4 cSt to about 8 cSt, or from about 4 cSt to about 6 cSt at 100° C. In certain embodiments, the lubricant compositions provided herein have kinetic viscosity from about 3 centistokes (cSt) to about 10 cSt, from about 4 cSt to about 8 cSt, or from about 4 cSt to about 6 cSt at 100° C. In certain embodiments, the lubricant compositions (e.g., base oils or base stocks) provided herein have kinetic of about 4, 5, or 6 cSt at 100° C.

In certain embodiments, the lubricant compositions (e.g., base oils or base stocks) provided herein have kinetic viscosity of about 15 cSt or greater at 40° C. In certain embodiments, the lubricant compositions provided herein have kinetic viscosity of about 20 cSt or greater at 40° C. In certain embodiments, the lubricant compositions provided herein have kinetic viscosity from about 15 cSt to about 40 cSt, from about 20 cSt to about 40 cSt, or from about 20 cSt to about 30 cSt at 40° C. In certain embodiments, the lubricant compositions have kinetic viscosity of about 20, 25, 30 or 35 cSt at 40° C. The kinetic viscosity of the lubricant compositions disclosed herein can be measured according to ASTM D 445.

In certain embodiments, the lubricant compositions (e.g., base oils or base stocks) provided herein have dynamic viscosity of about 10 cP or greater at 40° C. In certain embodiments, the lubricant compositions provided herein have dynamic viscosity of about 15 cP or greater at 40° C. In certain embodiments, the lubricant compositions provided herein have dynamic viscosity from about 10 cP to about 40 cP, from about 15 cP to about 30 cP, or from about 15 cP to about 25 cP at 40° C. In certain embodiments, the lubricant compositions provided herein have dynamic viscosity of about 15, 17, 20, 22, or cP at 40° C.

In certain embodiments, the lubricant compositions (e.g., base oils or base stocks) provided herein have dynamic viscosity of about 2 cP or greater at 100° C. In certain embodiments, the lubricant compositions provided herein have dynamic viscosity of about 3 cP or greater at 100° C. In certain embodiments, the lubricant compositions provided herein have dynamic viscosity from about 1 cP to about 10 cP, from about 1 cP to about 7 cP, or from about 2 cP to about 5 cP at 100° C. In certain embodiments, the lubricant compositions have dynamic viscosity of about 2, 3, 4 or 5 cP at 100° C. The dynamic viscosity of the lubricant compositions disclosed herein can be measured according to ASTM D 445.

In certain embodiments, lubricant compositions (e.g., base oils or base stocks) provided herein have a viscosity index of about 90 or greater according to ASTM D 2270. In certain embodiments, lubricant compositions provided herein have a viscosity index about 100 or greater according to ASTM D 2270. In certain embodiments, the viscosity index is from about 90 to about 150 or about 100 to about 140 according to ASTM D 2270. In certain embodiments, the viscosity index is from about 110 to about 130 according to ASTM D 2270. In certain embodiments, the viscosity index is about 100, 110, 120, 125, 130, 135, 140, 145, or 150, or even higher according to ASTM D 2270.

In certain embodiments, the lubricant compositions (e.g., base oils or base stocks) provided herein have density of about 0.700 to about 0.900 at 40° C. In certain embodiments, the lubricant compositions provided herein have density of about 0.700 to about 0.850 at 40° C. In certain embodiments, the lubricant compositions provided herein have density of about 0.700. 0.750, 0.800, 0.850 or 0.900 at 40° C. In certain embodiments, the lubricant compositions provided herein have density of about 0.700 to about 0.800 at 100° C. In certain embodiments, the lubricant compositions provided herein have density of about 0.700. 0.750, or 0.800 at 100° C.

In certain embodiments, provided herein are lubricant base stocks, lubricant base oils, lubricant additives, or finished lubricant compositions. In certain embodiments, the compositions provided herein have use as lubricity enhancers.

Certain of the lubricant compositions disclosed herein entail blending, mixing or solubizing of multiple base stocks or base oils, or blending, mixing or solubizing one or more base stocks or base oils with one or more additives. Any mixing, blending or dispersing equipment known in the art can be used for blending, mixing or solubilizing the components of the lubricant compositions.

Any lubricating oil additive known to a person of ordinary skill in the art may be used in the lubricant compositions disclosed herein. In some embodiments, the lubricating oil additive can be selected from the group consisting of antioxidants, antiwear agents, detergents, rust inhibitors, demulsifiers, friction modifiers, multi-functional additives, pour point depressants, foam inhibitors, metal deactivators, dispersants, corrosion inhibitors, thermal stability improvers, viscosity modifiers, dyes, markers, and any combination of two or more of the above-listed additives.

As described above, in certain embodiments, a base oil or base stock used in the lubricant compositions is a composition comprising squalane and/or isosqualane. In another embodiment, the lubricant compositions provided herein comprise a base oil (or base stock) of lubricating viscosity that does not comprise squalane or isosqualane. In some variations, the base oil that does not comprise squalane or isosqualane is used in addition to a base oil or base stock comprising squalane and/or isosqualane. Any base oil (or base stock) known to a skilled artisan can be used as the oil of lubricating viscosity disclosed herein. Some base oils suitable for preparing the lubricant compositions have been described in Mortier et al., "*Chemistry and Technology of Lubricants,*" 2nd Edition, London, Springer, Chapters 1 and 2 (1996); and A. Sequeria, Jr., "*Lubricant Base Oil and Wax Processing,*" New York, Marcel Decker, Chapter 6, (1994); and D. V. Brock, *Lubrication Engineering*, Vol. 43, pages 184-5, (1987), each of which is incorporated herein by reference. In certain embodiments, the amount of the base oil in the composition is greater than about 1 wt % based on the total weight of the composition. In certain embodiments, the amount of the base oil in the composition is greater that about 2, 5, 15 or 20 wt % based on the total weight of the composition. In some embodiments, the amount of the base oil in the composition is from about 1-20 wt % based on the total weight of the composition. In certain embodiments, the amount of base oil in compositions provided herein is about 1 wt %, 5 wt %, 7 wt %, 10 wt %, 13 wt %, 15 wt %, or 20 wt % based on total weight of the composition.

In certain embodiments, a base oil used in the lubricant compositions described herein is or comprises any natural or synthetic lubricating base oil fraction. Some non-limiting examples of synthetic oils include oils, such as polyalphaolefins or PAOs, prepared from the polymerization of at least one alpha-olefin, such as ethylene, or from hydrocarbon synthesis procedures using carbon monoxide and hydrogen gases, such as the Fisher-Tropsch process.

In other embodiments, a base oil used in the lubricant compositions described herein is or comprises a base stock or blend of base stocks. In further embodiments, the base stocks are manufactured using a variety of different processes including, but not limited to, distillation, solvent refining, hydrogen processing, oligomerization, esterification, and rerefining. In some embodiments, the base stocks comprise a rerefined stock. In further embodiments, the rerefined stock is substantially free from materials introduced through manufacturing, contamination, or previous use.

In some embodiments, a base oil used in the lubricant compositions comprises one or more of the base stocks in one or more of Groups I-V as specified in the American Petroleum Institute (API) Publication 1509, Fourteen Edition, December 1996 (i.e., API Base Oil Interchangeability Guidelines for Passenger Car Motor Oils and Diesel Engine Oils), which is incorporated herein by reference. The API guideline defines a base stock as a lubricant component that may be manufactured using a variety of different processes. Groups I, II and III base stocks include mineral oils and paraffinic stocks, each with specific ranges of the amount of saturates, sulfur content and viscosity index. Group IV base stocks are polyalphaolefins (PAO). Group V base stocks include all other base stocks not included in Group I, II, III, or IV.

The saturates levels, sulfur levels and viscosity indices for Group I, II, III, IV and V base stocks are listed in Table 4A below.

TABLE 4A

| Group | Saturates (As determined by ASTM D 2007) | Sulfur (As determined by ASTM D 2270) | Viscosity Index (As determined by ASTM D 4294, ASTM D 4297 or ASTM D 3120) |
|---|---|---|---|
| I | Less than 90% saturates. | Greater than or equal to 0.03% sulfur. | Greater than or equal to 80 and less than 120. |
| II | Greater than or equal to 90% saturates. | Less than or equal to 0.03% sulfur. | Greater than or equal to 80 and less than 120. |
| III | Greater than or equal to 90% saturates. | Less than or equal to 0.03% sulfur. | Greater than or equal to 120. |
| IV | Defined as polyalphaolefins (PAO) | | |

TABLE 4A-continued

| Group | Saturates (As determined by ASTM D 2007) | Sulfur (As determined by ASTM D 2270) | Viscosity Index (As determined by ASTM D 4294, ASTM D 4297 or ASTM D 3120) |
|---|---|---|---|
| V | All other base stocks not included in Groups I, II, III or IV | | |

In certain embodiments, a base oil used in the lubricant compositions disclosed herein is selected from the group consisting of natural oils of lubricating viscosity, synthetic oils of lubricating viscosity and mixtures thereof. In some embodiments, the base oil includes base stocks obtained by isomerization of synthetic wax and slack wax, as well as hydrocrackate base stocks produced by hydrocracking (rather than solvent extracting) the aromatic and polar components of the crude. In other embodiments, the base oil of lubricating viscosity includes natural oils, such as animal oils, vegetable oils, mineral oils (e.g., liquid petroleum oils and solvent treated or acid-treated mineral oils of the paraffinic, naphthenic or mixed paraffinic-naphthenic types), oils derived from coal or shale, and combinations thereof. Some non-limiting examples of animal oils include bone oil, lanolin, fish oil, lard oil, dolphin oil, seal oil, shark oil, tallow oil, and whale oil. Some non-limiting examples of vegetable oils include castor oil, olive oil, peanut oil, rapeseed oil, corn oil, sesame oil, cottonseed oil, soybean oil, sunflower oil, safflower oil, hemp oil, linseed oil, tung oil, oiticica oil, jojoba oil, and meadow foam oil. Such oils may be partially or fully hydrogenated.

In some embodiments, the synthetic oils of lubricating viscosity used in the lubricant compositions described herein include hydrocarbon oils and halo-substituted hydrocarbon oils such as polymerized and inter-polymerized olefins, alkylbenzenes, polyphenyls, alkylated diphenyl ethers, alkylated diphenyl sulfides, as well as their derivatives, analogues and homologues thereof, and the like. In other embodiments, the synthetic oils include alkylene oxide polymers, interpolymers, copolymers and derivatives thereof wherein the terminal hydroxyl groups can be modified by esterification, etherification, and the like. In further embodiments, the synthetic oils include the esters of dicarboxylic acids with a variety of alcohols. In certain embodiments, the synthetic oils include esters made from $C_5$ to $C_{12}$ monocarboxylic acids and polyols and polyol ethers. In further embodiments, the synthetic oils include tri-alkyl phosphate ester oils, such as tri-n-butyl phosphate and tri-iso-butyl phosphate.

In some embodiments, the synthetic oils of lubricating viscosity used in the lubricant compositions described herein include silicon-based oils (such as the polyalkyl-, polyaryl-, polyalkoxy-, polyaryloxy-siloxane oils and silicate oils). In other embodiments, the synthetic oils include liquid esters of phosphorus-containing acids, polymeric tetrahydrofurans, polyalphaolefins, and the like.

Base oil derived from the hydroisomerization of wax may be used in the lubricant compositions described herein, either alone or in combination with the aforesaid natural and/or synthetic base oil. Such wax isomerate oil is produced by the hydroisomerization of natural or synthetic waxes or mixtures thereof over a hydroisomerization catalyst.

In further embodiments, the base oil used in the lubricant compositions described herein comprises a poly-alpha-olefin (PAO). In general, the poly-alpha-olefins may be derived from an alpha-olefin having from about 2 to about 30, from about 4 to about 20, or from about 6 to about 16 carbon atoms. Non-limiting examples of suitable poly-alpha-olefins include those derived from octene, decene, mixtures thereof, and the like. These poly-alpha-olefins may have a viscosity from about 2 to about 15, from about 3 to about 12, or from about 4 to about 8 centistokes at 100° C. In some instances, the poly-alpha-olefins may be used together with other base oils such as mineral oils.

In further embodiments, a base oil used in the lubricant compositions described herein comprises a polyalkylene glycol or a polyalkylene glycol derivative, where the terminal hydroxyl groups of the polyalkylene glycol may be modified by esterification, etherification, acetylation and the like. Non-limiting examples of suitable polyalkylene glycols include polyethylene glycol, polypropylene glycol, polyisopropylene glycol, and combinations thereof. Non-limiting examples of suitable polyalkylene glycol derivatives include ethers of polyalkylene glycols (e.g., methyl ether of polyisopropylene glycol, diphenyl ether of polyethylene glycol, diethyl ether of polypropylene glycol, etc.), mono- and polycarboxylic esters of polyalkylene glycols, and combinations thereof. In some instances, the polyalkylene glycol or polyalkylene glycol derivative may be used together with other base oils such as poly-alpha-olefins and mineral oils.

In further embodiments, a base oil used in the lubricant compositions described herein comprises any of the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, and the like) with a variety of alcohols (e.g., butyl alcohol, hexyl alcohol, dodecyl alcohol, 2-ethylhexyl alcohol, ethylene glycol, diethylene glycol monoether, propylene glycol, and the like). Non-limiting examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the like.

In further embodiments, a base oil used in the lubricant compositions described herein comprises a hydrocarbon prepared by the Fischer-Tropsch process. The Fischer-Tropsch process prepares hydrocarbons from gases containing hydrogen and carbon monoxide using a Fischer-Tropsch catalyst. These hydrocarbons may require further processing in order to be useful as base oils. For example, the hydrocarbons may be dewaxed, hydroisomerized, and/or hydrocracked using processes known to a person of ordinary skill in the art.

In further embodiments, the base oil used in the lubricant compositions described herein comprises an unrefined oil, a refined oil, a rerefined oil, or a mixture thereof. Unrefined oils are those obtained directly from a natural or synthetic source without further purification treatment. Non-limiting examples of unrefined oils include shale oils obtained directly from retorting operations, petroleum oils obtained directly from primary distillation, and ester oils obtained directly from an esterification process and used without further treatment. Refined oils are similar to the unrefined oils except the former have been further treated by one or more purification processes to improve one or more properties. Many such purification processes are known to those skilled in the art such as solvent extraction, secondary distillation, acid or base extraction, filtration, percolation, and the like. Rerefined oils are obtained by applying to refined oils processes similar to those used to obtain refined oils. Such rerefined oils are also known as reclaimed or reprocessed oils and often are additionally treated by processes directed to removal of spent additives and oil breakdown products.

In certain embodiments, the lubricant compositions comprising squalane and/or isosqualane provided herein have use as pour point depressant additives.

In certain embodiments, a lubricant composition may comprise a base oil comprising squalane and/or isosqualane as provided herein, and farnesane as an additive. For example, some variations of lubricant compositions (e.g., in a two cycle engine oil formulation) may comprise about 25-75 wt % isosqualane and/or squalane (e.g., about 25, 30, 35, 40, 45, 50, 55, 60, 65, 70 or 75 wt % isosqualane and/or squalane) as a base oil and about 1-30 wt % farnesane (e.g., about 1 wt %, 5 wt %, 10 wt %, 15 wt %, 20 wt %, 25 wt %, or wt %) as an additive. For example, one variation of a lubricant composition comprises about 30-60 wt % squalane and/or isosqualane, 5-15 wt % farnesane, and about 40-60 wt % additives which have been selected so that the lubricant composition meets specifications for a particular application.

In certain embodiments, the pour point depressant additive composition provided herein further comprises an oil or a solvent miscible with oil. Examples of solvents are organic solvents including hydrocarbon solvents, for example petroleum fractions such as naphtha, kerosene, diesel and heater oil; aromatic hydrocarbons; alcohols and/or esters; and paraffinic hydrocarbons such as hexane and pentane and isoparaffins. The solvent is selected based on its compatibility with the additive and with the oil. Examples of oils for use herein include crude oil or fuel oil. In certain embodiments, the oil is a lubricating oil, which may be an animal, vegetable or mineral oil, such as petroleum oil fractions ranging from naphthas or spindle oil to SAE 30, 40 or 50 lubricating oil grades, castor oil, fish oils, oxidized mineral oil, or biodiesels. The pour point depressant compositions provided herein are useful in lubricating oils as flow improvers, pour point depressants or dewaxing aids.

In certain embodiments, the lubricant compositions provided herein are used in combination with one or more other additives known in the art, for example the following: antioxidants, antiwear agents, extreme pressure agents, detergents, rust inhibitors, corrosion inhibitors, demulsifiers, friction modifiers, pour point depressants, seal swell agents, foam inhibitors, metal deactivators, dispersants, thermal stability improvers, dyes, markers, particulate emission reducers, storage stabilizers, corrosion inhibitors, cetane improvers, cosolvents, viscosity modifiers, package compatibilizers, multi-functional additives, conductivity enhancers, load-bearing additives, and lubricity enhancers. As used herein, "multi-functional additives" means an additive that provides a multiple effects to the lubricant composition to which it is added, e.g., a multi-functional additive that is known to function as a dispersant and as an oxidation inhibitor. Examples of multi-functional additives are known in the art.

The lubricant compositions described herein can used in a variety of applications, e.g., as lubricants for automotive, tractor, airline, railroad, metal working, and industrial manufacturing sectors. For example, the lubricant compositions can be used in engines, turbines, pumps, compressors, gears, gear boxes, axels, transmissions, crankcases, and factory equipment. The base oil and additives can be selected, and their relative amounts determined, to create a finished lubricant formulation that meets certain industry standards for use in specified applications in that industry. For example, finished lubricant formulations can be developed for use as automatic transmission fluid (ATF), transmission oil, axel lubricating oil, crankcase oil, hydraulic fluid, compressor fluid, two-cycle oil, and the like.

In certain embodiments, the compositions provided herein have use as fuel additives in fuels used to, for example, power internal combustion engines such as reciprocating engines (e.g., gasoline engines and diesel engines), Wankel engines, jet engines, some rocket engines, missile engines, and gas turbine engines. The compositions provided herein can be used in combination with other fuel additives known in the art. Types of fuel additives include, but are not limited to, antioxidants, thermal stability improvers, cetane improvers, stabilizers, cold flow improvers, combustion improvers, antifoams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides, and combinations thereof.

Disclosed herein are methods of lubricating a machine or a component of a machine (e.g., an engine, transmission, gear, axel, turbine, pump, crankcase, gear box, compressor, and the like) using the lubricant compositions described herein. The lubricant compositions described herein can be placed in physical contact with a component of the machine while the machine (or at least that component of the machine) is operated. In some variations, the lubricant compositions function to reduce friction between two or more surfaces of the lubricated machine component. In some applications, at least a portion of the lubricant composition is consumed during use (e.g., combusted), while in other applications, the lubricant composition is not substantially consumed during use.

Disclosed herein are machines comprising the lubricants described herein, e.g., any machine comprising engines, transmissions, gears, axels, turbines, pumps, crankcases, gear boxes, and/or compressors containing one or more the lubricant compositions described herein. Non-limiting examples of such machines include automobiles, tractors, trucks, conveyors, trains, wind turbines, gas turbines, pumping apparatus, airplanes, drilling apparatus, and factory equipment.

Vaccine Adjuvants

In some variations, the compositions described herein may be useful as vaccine adjuvants. For example, those compositions having high purity with respect to squalane may be used as vaccine adjuvants, e.g., compositions comprising at least about 90%, 91%, 92%, 93%, 94%, 95%, 96%, 97%, or 98% squalane and about 0.1% to about 10% isosqualane may be used, where % refers to wt %, vol %, or area % of the total composition. In some embodiments, compositions comprising at least about 90% squalane and about 0.1% to about 5% isosqualane may be used as vaccine adjuvants. In some embodiments, compositions comprising at least about 92% squalane and about 0.1% to about 5% isosqualane may be used as vaccine adjuvants.

While the compounds, compositions and methods have been described with respect to a limited number of embodiments, the specific features of certain embodiments should not be attributed to other embodiments described herein. No single embodiment is representative of all aspects of the compositions or methods. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist.

EXAMPLES

The practice of the present subject matter can employ, unless otherwise indicated, conventional techniques in the industry and the like, which are within the skill of the art. To the extent such techniques are not described fully herein, one can find ample reference to them in the scientific literature.

In the following examples, efforts have been made to ensure accuracy with respect to numbers used (for example, amounts, temperature, and so on), but variation and deviation can be accommodated, and in the event a clerical error in the numbers reported herein exists, one of ordinary skill in the art can deduce the correct amount in view of the remaining disclosure herein. Unless indicated otherwise, temperature is reported in degrees Celsius. All reagents, unless otherwise indicated, were obtained commercially. β-farnesene used herein is prepared as described in U.S. Pat. No. 7,399,323 B1 which is incorporated by reference in its entirety. Unless indicated otherwise, β-farnesene was filtered through alumina, and 4-tert-butylcatechol was added at 100 ppm. The following examples are intended for illustrative purposes only and do not limit in any way the scope of the present invention.

In the examples below, conversion % refers to conversion of β-farnesene to a reaction product in the dimerization reaction based on the amount of β-farnesene in the reactant. Isosqualene % refers to the amount of isosqualene in the reaction product based on the total amount of the reaction product obtained in the dimerization reaction. Squalane % refers to the amount of squalane in the reaction product obtained after the dimerization and hydrogenation reactions based on the total amount of the reaction product of the hydrogenation reaction, as measured as an area % by GC-MS or GC-FID. Others % refers to the amount of products other than isosqualene based on the total amount of the reaction product obtained in the dimerization reaction. In is noted that in certain circumstances, others % convert to squalane after hydrogenation. In some cases, one or more species corresponding to isosqualene molecular weight +2 are observed by GC-MS. Squalane ratio refers to the ratio of quantity squalane to quantity isosqualene obtained after the hydrogenation of the product obtained in dimerization of β-farnesene. Unless indicated otherwise, the squalane ratio was determined by GC.

Standard abbreviations and acronyms are used herein. Certain abbreviations and acronyms used herein are as follows
IPA=Isopropyl alcohol
$Pd(acac)_2$=Palladium (II) acetyl acetonate
$PPh_3$=Triphenyl phosphine
$PTol_3$=Tritolyl phosphine
$PBu_3$=Tributyl phosphine
$PEt_3$=Triethyl phosphine
$iPr_3P$=Triisopropyl phosphine
tBuONa or NaO-tBu=Sodium tert-butoxide
dcpb=2-(Dicyclohexylphosphino)biphenyl
Xantphos=4,5-Bis(diphenylphosphino)-9,9-dimethylxanthene
tris-(3-MeO-Ph)$_3$P-Tris(2-methoxyphenyl)phosphine
dppp=1,3-bis(diphenylphosphino)propane
dPEPhos=Bis(2-diphenylphosphinophenyl)ether
$Cy_2PPh$=Dicyclohexyl(phenyl)phosphine
Dppb=1,4-Bis(diphenylphosphino)butane
BINAP=2,2'-bis(diphenylphosphino)-1,1'-binaphthyl
$Pd(cod)Cl_2$=Palladium (1,5-cyclooctadiene) dichloride
$Pd(dba)_2$=Bis(dibenzylideneacetone)palladium
$[Pd(allyl)Cl]_2$=Allylpalladium chloride dimer
dcpp=bis dicyclohexyphosphinobutane
$Et_2AlCl$=diethyl aluminum chloride
$Oct_3Al$=tri-n-octyl aluminum
$PhCy_3$=tricyclohexylphosphine
$Zr(OtBu)_4$=zirconium tetrakis(tert-butoxide)
$iBu_3Al$=tri(iso-butyl) aluminum
$Et_3Al$=triethyl aluminum
$P(o-OMePh)_3$=tris(ortho-methoxyphenyl)phosphine
$P(m-OMePh)_3$=tris(meta-methoxyphenyl)phosphine
$Ph_2PtBu$=diphenyl tert-butyl phosphine
Bipy=2,2'-bipyridine
DPPE=1,2-Bis(diphenylphosphino)ethane
MAO=methylaluminoxane or methylaluminoxanes
$ZrCl_4$=zirconium tetrachloride
$TiCl_4$=titanium tetrachloride
$Et_2Al(OEt)$=diethyl aluminum ethoxide Example 1

Ligands Screening

In this example, β-farnesene was converted to isosqualene using $Pd(acac)_2$ as precursor and the ligands described in Table 1. The catalyst precursor and ligand were weighed in a glass liner (S/C 125/1) under inert atmosphere, then isopropyl alcohol (IPA) (2 mL) was added followed by β-farnesene (510 µL, 2.5 mmol, [c]=1M), the reaction was heated for 7 h at 85° C. The hydrogenation of the crude reaction product from dimerization reaction was carried out using Pd/C at 30 bar $H_2$ and 50° C. for 16 h.

The reactions were analyzed by gas chromatography. The following peaks were observed: β-farnesene at 4.1 min, and isosqualene at 20.1 min. Data provided in Table 1 includes the % conversion of β-farnesene and ratios of squalane to impurities for the ligands tested.

TABLE 1

Ligands screening using $Pd(acac)_2$/2.8 L

| Entry | Catalyst | Conv (%) | Iso-squalene (%) | Others (%) | Squalane Ratio |
|---|---|---|---|---|---|
| 1 | $Pd(acac)_2$ + 2.8 eq $PPh_3$ | 87 | 78 | 5 | 22/1 |
| 2 | $Pd(acac)_2$ + 2.8 eq $PBu_3$, $HBF_4$ + 6eq tBuONa | 93 | 70 | 23 | 19/1 |
| 3 | $Pd(acac)_2$ + 1.5 eq dcpb | 75 | 60 | 15 | 16/1 |
| 4 | $Pd(acac)_2$ + 2.8 eq $P(OPh)_3$ | 82 | 50 | 32 | 8/1 |
| 5 | $Pd(acac)_2$ + 1.5 eq Xantphos | 37 | 20 | 17 | 12/1 |
| 6 | $Pd(acac)_2$ + 2.8 eq tris-(3-MeO—Ph)$_3$P | 39 | 19 | 20 | 13/1 |
| 7 | $Pd(acac)_2$ + 2.8 eq $PEt_3$ | 30 | 15 | 15 | 22/1 |
| 8 | $Pd(acac)_2$ + 2.8 eq $Ph_2PO$—$(CH_2)_2$—$NMe_2$ | 25 | 11 | 14 | 4.5/1 |
| 9 | $Pd(acac)_2$ + 2.8 eq P(O-2-6,tBu—Ph)$_3$ | 14 | 9 | 5 | |
| 10 | $Pd(acac)_2$ + 1.5 eq dppp | 15 | 8 | 7 | |
| 11 | $Pd(acac)_2$ + 1.5 eq DPEPhos | 20 | 7 | 13 | |
| 12 | $Pd(acac)_2$ + 2.8 eq Me(tBu)$_2$P, $HBF_4$ + 4 eq tBuONa | 8 | 4 | 4 | |
| 13 | $Pd(acac)_2$ + 2.8 eq $Cy_2PPh$ | 8 | 4 | 4 | |
| 14 | $Pd(acac)_2$ + 2.8 eq tris-2-furfuryl phosphine | 17 | 3 | 14 | |
| 15 | $Pd(acac)_2$ + 2.8 eq (N-2-dipyridyl)-diphenylphosphine (sold as CataCxium ® KPh) | 8 | 2 | 8 | |
| 16 | $Pd(acac)_2$ + 1.5 eq dppb | 4 | 2 | 2 | |
| 17 | $Pd(acac)_2$ + 2.8 eq $iPr_3P$ | 2 | 1 | 1 | |
| 18 | $Pd(acac)_2$ + 2.8 eq $PhP(CH_2$—$CH_2CN)_2$ | 2 | 1 | 1 | |
| 19 | $Pd(acac)_2$ + 1.4 eq BINAP | 2 | — | 2 | |

TABLE 1-continued

Ligands screening using Pd(acac)$_2$/2.8 L

| Entry | Catalyst | Conv (%) | Iso-squalene (%) | Others (%) | Squalane Ratio |
|---|---|---|---|---|---|
| 20 | Pd(acac)$_2$ + 2.8 eq tris-2-thienyl phosphine | 3 | — | 3 | |
| 24 | Pd(acac)$_2$ + 2.8 eq tris-pentaflurophenyl phosphine | 4 | — | 4 | |
| 25 | Pd(acac)$_2$ + 2 eq Im Me, Et PF6 + 4 eq NaO—tBu | 2 | — | 2 | |
| 26 | Pd(acac)$_2$ + 2.8 eq di-Cy-(2'-Me-biphenyl) | 6 | — | 6 | |
| 27 | Pd(acac)$_2$ + 2.8 eq di-Cy-(biphenyl) | 8 | — | 8 | |
| 28 | Pd(acac)$_2$ + 2.8 eq di-t-Bu-(biphenyl) | 5 | — | 5 | |
| 29 | Pd(acac)$_2$ + 2.8 eq di-Cy-(2-pyrrol-phenyl) - (sold as CataCxium ® PCy) | 6 | — | 6 | |
| 30 | Pd(acac)$_2$ + 2.8 (benzyl) adamantyl phosphine (sold as CataCxium ® ABn) | 2 | — | 2 | |

The squalane ratio was measured for those reactions where conversions was above 10%, i.e., Entries 1-8. With 2.8 eq. of PPh$_3$ as ligand, 78% iso-squalene was observed in the product. Squalane ratio after hydrogenation reaction was 22/1 (Entry 1). Alkyl phosphine ligands, Bu$_3$P and dcpp (bis dicyclohexyphosphinobutane) provided 70% and 60% isosqualene after dimerization, respectively (Entries 2 and 3). In both cases, the squalane ratio after hydrogenation was above 16 to 1.

Using P(OPh)$_3$ as ligand, 50% isosqualene was obtained after dimerization with a lower squalane purity of 8 to 1 (Entry 4) in the hydrogenation reaction. With bidentate Xantphos and tri aryl phosphine, tris-(3-MeO-Ph)$_3$P ligands, isosqualene % was between 10% and 50%, respectively. The hydrogenation of the products gave squalane ratio above 10 to 1 (Entries 5-6). The basic aliphatic phosphine ligand PEt$_3$ gave only 15% selectivity for isosqualene with a squalane ratio similar to the one obtained with PPh$_3$ (Entry 7), i.e., squalane ratio of 22/1. A bidentate amino-phosphinate ligand, . i.e., Ph$_2$PO—(CH$_2$)$_2$—NMe$_2$, gave 11% selectivity for isosqualene with a low squalane ratio of 4.5 to 1 (Entry 8).

All the other ligands used gave selectivity below 10% and no hydrogenation of the crude reaction was performed to evaluate the ratio of squalane (Entries 9-30).

Based on the results, PPh$_3$ ligand was selected for additional studies.

Example 2

Use of Additives to Generate Pd(0)

Several additives such inorganic bases or reducing agents were tested in order to generate a Pd(0) from a preformed Pd(PPh$_3$)$_2$Cl$_2$ catalyst.

Experimental procedure: the catalyst was weighed in a glass liner (S/C 125/1) under inert atmosphere, then IPA (2 mL) was added followed by β-farnesene (510 μL, 2.5 mmol, [c]=1M). The dimerization and hydrogenation reaction was carried out as described in Example 1.

The reactions were analyzed by gas chromatography. The following peaks were observed: β-farnesene at 4.1 min, iso-squalene at 20.1 min, impurities=13.45 min. The impurity comprised partially reduced isosqualene. The additives tested and results are summarized in Table 2. Data provided in Table 2 includes the % conversion of β-farnesene and ratios of squalane to impurities for the additives tested.

TABLE 2

Use of additives with Pd(PPh$_3$)$_2$Cl$_2$

| Entry # | Cat. | Solvent | Conv (%) | Iso-squalene (%)$^a$ | Others (%) | Squalane Ratio |
|---|---|---|---|---|---|---|
| 1 | Pd(PPh$_3$)$_2$Cl$_2$ + 20% NEt$_3$ | IPA | 3 | 1 | 2 | |
| 2 | Pd(PPh$_3$)$_2$Cl$_2$ + 20% (25 eq) NaO—tBu | IPA | 45 | 33 | 12 | 25/1 |
| 3 | Pd(PPh$_3$)$_2$Cl$_2$ + 20% HCO$_2$H 1/NEt$_3$ 1 | IPA | 45 | 1 | 45 (31*) | 2/1 |
| 4 | Pd(PPh$_3$)$_2$Cl$_2$ + 20% HCO$_2$Na | IPA | 75 | 36 | 39 (35*) | 26/1 |
| 5 | Pd(PPh$_3$)$_2$Cl$_2$ + 50% w/w Zn | IPA | 7 | — | 7 | |
| 6 | Pd(PPh$_3$)$_2$Cl$_2$ + 50% NaBH$_4$ | IPA | 23 | 2 | 21 | |

*amount of impurity between 16 min and 20 min (the impurity is mostly neosqualane and some partially reduced isosqualene)

Among the bases tested in this reaction, NEt$_3$ gave no conversion (Entry 1) while t-BuONa gave 33% conversion to the product with a squalane ratio of 25/1 (Entry 2). Other reducing agents were tested such as HCO$_2$H 1/NEt$_3$ 1 and HCO$_2$Na and gave low selectivity to the product due to significant amounts of partially reduced iso-squalene (Entries 3-4). Two crude reactions were hydrogenated and squalane ratios of 2/1 and 26/1 were obtained for HCO$_2$H 1/NEt$_3$ 1 and HCO$_2$Na, respectively. Other additives such a NaBH$_4$, Zn dust did not give any conversion (Entries 5-6). Based on the results, further tests were conducted with 20 mol % of HCO$_2$Na.

Example 3

Use of 20 Mol % of HCO$_2$Na with Preformed Catalyst L$_2$PdCl$_2$

According to Example 2 (Table 2), sodium formate generated a Pd(0) from a preformed Pd(II) complex. Ligands were tested as L$_2$PdCl$_2$ with 20 mol % of HCO$_2$Na.

Experimental procedure: the catalyst was weighed in a glass liner under inert atmosphere (S/c 125/1), 2 mL IPA was added, followed by β-farnesene (510 μL mL, 2.5 mmol, [c]=1M). The reaction was heated at 85° C. for 7 hours. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 3 are presented after the steps: (1) the coupling to obtain isosqualene, followed by (2) hydrogenation to obtain squalane. Data provided in Table 3 includes the % conversion of β-farnesene and ratios of squalane to impurities.

TABLE 3

Use of 20 mol % of $HCO_2Na$ with preformed catalyst $L_2PdCl_2$

| Entry | Cat. | Conv (%)[a] | Squalane (%) | Others (%)[a] | Squalane Ratio |
|---|---|---|---|---|---|
| 1 | $Pd(PEt_3)_2Cl_2$ IPA, 20 mol % $HCO_2Na$ | 90 | 78 | 12 | 16/1 |
| 2 | $Pd(PPh_3)_2Cl_2$ IPA, 20 mol % $HCO_2Na$ | 88 | 83 | 5 | 26/1 |
| 3 | Im-Mes Pd Cl (allyl) IPA, 20 mol % $HCO_2Na$ | 77 | 29 | 48 | 3/1 |
| 4 | $Pd(PCy_3)_2Cl_2$ IPA, 20 mol % $HCO_2Na$ | 63 | 54 | 9 | 11/1 |
| 5 | $Pd(PhPt—Bu_2)_2Cl_2$ IPA, 20 mol % $HCO_2Na$ | 43 | 32 | 11 | 5/1 |

β-farnesene conversions of 90 and 88% were obtained for $(PEt_3)_2PdCl_2$ and $(PPh_3)_2PdCl_2$ (Entries 1-2), respectively. FIG. 1 provides an GC spectrum for the reaction described in Table 3, entry 2. Squalane ratio of 26/1 was observed for $(PPh_3)_2PdCl_2$ catalyst. The other catalyst tested gave lower conversion and squalane ratios (Entries 3-5).

Example 4

Use of 20 Mol % of $HCO_2Na$ with In Situ Formed Catalyst $Pd(cod)Cl_2$/2 L

In this example, $Pd(cod)Cl_2$ was premixed with the monodentate phosphine in the presence of 20 mol % of $NaHCO_2$ (Table 4).

Experimental procedure: the catalyst was weighed in a glass liner under inert atmosphere (S/c 125/1), 2 mL IPA was added, followed by β-farnesene (510 μL mL, 2.5 mmol, [c]=1M). The reaction was heated to 85° C. for 7 hours. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 4 are presented after the steps: (1) the coupling to obtain isosqualene, followed by (2) hydrogenation to obtain squalane. Data provided in Table 4 includes the % conversion of β-farnesene and ratios of squalane to impurities.

TABLE 4

Use of 20% $HCO_2Na$ with catalyst formed in situ with $Pd(cod)Cl_2$

| Entry | Cat. | Conv (%) | Squalane (%) | Others (%) | Squalane Ratio |
|---|---|---|---|---|---|
| 1 | $Pd(cod)Cl_2$ + 2 (o-MeOPh)$PPh_2$ IPA, 20 mol % $HCO_2Na$ | 99 | 93 | 6 | 19/1 |
| 2 | $Pd(cod)Cl_2$ + 2 $PEt_3$ IPA, 20 mol % $HCO_2Na$ | 99 | 93 | 6 | 15/1 |
| 3 | $Pd(cod)Cl_2$ + 2 (p-MeO-Xyl)$_3$P IPA, 20 mol % $HCO_2Na$ | 99 | 94 | 5 | 19/1 |
| 4 | $Pd(cod)Cl_2$ + 2 (Xyl)$_3$P IPA, 20 mol % $HCO_2Na$ | 99 | 94 | 5 | 22/1 |
| 5 | $Pd(cod)Cl_2$ + 2 (p-Tol)$_3$P IPA, 20 mol % $HCO_2Na$ | 99 | 88 | 11 | 17/1 |
| 6 | $Pd(cod)Cl_2$ + 2 (p-NMe$_2$—Ph)$PPh_2$ IPA, 20 mol % $HCO_2Na$ | 98 | 93 | 5 | 22/1 |
| 7 | $Pd(cod)Cl_2$ + 2 $BnPPh_2$ IPA, 20 mol % $HCO_2Na$ | 98 | 92 | 6 | 17/1 |
| 8 | $Pd(cod)Cl_2$ + 2 (m-Tol)$_3$P IPA, 20 mol % $HCO_2Na$ | 98 | 92 | 6 | 21/1 |
| 9 | $Pd(cod)Cl_2$ + 2 (Cy)$_2$PPh IPA, 20 mol % $HCO_2Na$ | 98 | 86 | 12 | 12/1 |
| 10 | $Pd(cod)Cl_2$ + 2 $Ph_2PMe$ IPA, 20 mol % $HCO_2Na$ | 96 | 91 | 5 | 19/1 |
| 11 | $Pd(cod)Cl_2$ + 2 (o-Tol)$PPh_2$ IPA, 20 mol % $HCO_2Na$ | 96 | 89 | 7 | 20/1 |
| 12 | $Pd(cod)Cl_2$ + 2 $Ph_3P$ IPA, 20 mol % $HCO_2Na$ | 96 | 89 | 7 | 23/1 |
| 13 | $Pd(cod)Cl_2$ + 2 ($^n$Bu)$_3$P, $HBF_4$ IPA, 20 mol % $HCO_2Na$ | 89 | 71 | 18 | 9/1 |
| 14 | $Pd(cod)Cl_2$ + 2 (m-MeO—Ph)$_3$P IPA, 20 mol % $HCO_2Na$ | 83 | 74 | 9 | 19/1 |
| 15 | $Pd(cod)Cl_2$ + 2 t-$Bu_2PPh$, $HBF_4$ IPA, 20 mol % $HCO_2Na$ | 82 | 64 | 18 | 5/1 |
| 16 | $Pd(cod)Cl_2$ + 2 (NC-$CH_2$—$CH_2$)$_2$PPh IPA, 20 mol % $HCO_2Na$ | 70 | 65 | 5 | 15/1 |
| 17 | $Pd(cod)Cl_2$ + (o-Tol)$_3$P IPA, 20 mol % $HCO_2Na$ | 70 | 63 | 7 | 10/1 |
| 18 | $Pd(cod)Cl_2$ + 2 $Me_3P$ IPA, 20 mol % $HCO_2Na$ | 70 | 63 | 7 | 11/1 |
| 19 | $Pd(cod)Cl_2$ + 2 (p-Cl—Ph)$_3$P IPA, 20 mol % $HCO_2Na$ | 28 | 19 | 9 | 9/1 |
| 20 | $Pd(cod)Cl_2$ + 2 (p-$CF_3$—Ph)$_3$P IPA, 20 mol % $HCO_2Na$ | 23 | 15 | 8 | 4.5/1 |
| 21 | $Pd(cod)Cl_2$ + 2 $Cy_3P$, $HBF_4$ IPA, 20 mol % $HCO_2Na$ | 14 | 7 | 7 | 2/1 |

TABLE 4-continued

Use of 20% HCO₂Na with catalyst formed in situ with Pd(cod)Cl₂

| Entry | Cat. | Conv (%) | Squalane (%) | Others (%) | Squalane Ratio |
|---|---|---|---|---|---|
| 22 | Pd(cod)Cl₂ + 2 (2-furfuryl)₃P IPA, 20 mol % HCO₂Na | 9 | 6 | 3 | 3/1 |
| 23 | Pd(cod)Cl₂ + 2 (2-thienyl)₃P IPA, 20 mol % HCO₂Na | 2 | 1 | 1 | — |

A variety of phosphines were tested with the Pd(cod)Cl₂ precursor. In most cases, greater than 80% conversion of β-farnesene was observed (Entries 1-15). Electron rich (methyl substituted or NMe₂) and non-bulky triaryl phosphine ligands gave squalane ratios above 20 to 1 (Entries 4, 6, 8, 11, 12).

Example 5

Ligand Stoichiometry and Palladium Precursors

In this example, the ligand stoichiometry and the nature of the palladium precursors were tested. Several reactions were performed using various amount of PPh₃ with Pd(cod)Cl₂ and palladium precursors with 2 equivalents of PPh₃.

Experimental procedure: the catalyst was weighed in a glass liner under inert atmosphere (S/c 125/1), 2 mL IPA was added followed by β-farnesene (510 μL mL, 2.5 mmol, [c]=1M). The reaction was heated at 85° C. for 7 hours. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 5 are presented after the steps: (1) the coupling to obtain isosqualene, followed by (2) hydrogenation to obtain squalane. Data provided in Table 5 includes the % conversion of β-farnesene and ratios of squalane to impurities for the ligand stoichiometries tested.

TABLE 5

Ligand Stoichiometry and Palladium precursors

| Entry # | Cat. | Conv (%) | Squalane (%) | Others (%) | Squalane Ratio |
|---|---|---|---|---|---|
| Ligand stoichiometry | | | | | |
| 1 | Pd(cod)Cl₂ + 1 Ph₃P IPA, 20 mol % HCO₂Na | 65 | 53 | 12 | 21/1 |
| 2 | Pd(cod)Cl₂ + 2 Ph₃P IPA, 20 mol % HCO₂Na | 96 | 89 | 7 | 23/1 |
| 3 | Pd(cod)Cl₂ + 3 Ph₃P IPA, 20 mol % HCO₂Na | 96 | 87 | 9 | 22/1 |
| Palladium precursors | | | | | |
| 1 | Pd(PhCN)Cl₂ + 2 Ph₃P IPA, 20 mol % HCO₂Na | 98 | 89 | 9 | 17/1 |
| 2 | [Pd(allyl)Cl]₂ + 2 Ph₃ IPA, 20 mol % HCO₂Na | 97 | 89 | 8 | 23/1 |
| 3 | Pd(cod)Cl₂ + 2 Ph₃P IPA, 20 mol % HCO₂Na | 96 | 89 | 7 | 23/1 |
| 4 | PdCl₂ + 2 Ph₃P IPA, 20 mol % HCO₂Na | 96 | 83 | 13 | 10/1 |
| 5 | Pd(dba) + 2 Ph₃P IPA, 20 mol % HCO₂Na | 95 | 88 | 7 | 23/1 |
| 6 | Pd(acac)₂ + 2 Ph₃P IPA, 20 mol % HCO₂Na | 92 | 86 | 6 | 23/1 |

TABLE 5-continued

Ligand Stoichiometry and Palladium precursors

| Entry # | Cat. | Conv (%) | Squalane (%) | Others (%) | Squalane Ratio |
|---|---|---|---|---|---|
| 7 | Pd(OAc)₂ + 2 Ph₃P IPA, 20 mol % HCO₂Na | 78 | 69 | 9 | 13/1 |

Using at least one equivalent of PPh₃, high conversion and a similar squalane ratios were obtained (Entries 2-3).

Of the palladium precursors tested in this reaction, the useful results in terms of conversion/selectivity and squalane ratio (23/1) were obtained with: [Pd(allyl)Cl]₂, Pd(cod)Cl₂, Pd(dba) and Pd(acac)₂. For the other palladium precursors, with the exception of Pd(OAc)₂, conversions were 92-98% but the squalane ratios were lower.

Example 6

Catalyst Loadings

The catalytic systems, based on Pd precursors/2 eq PPh₃/20 mol % NaHCO₂, were tested at catalytic loadings, from S/C 125/1 to 1000/1.

Experimental procedure: the catalyst was weighed in a glass liner under inert atmosphere, 4 mL IPA was added followed by β-farnesene (510 μL mL, 2.5 mmol, [c]=1 M). The reaction was heated at 85° C. for 7 hours. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 6 are presented after the steps: (1) the coupling to obtain isosqualene, followed by (2) hydrogenation to obtain squalane. Data provided in Table 16 includes the % conversion of β-farnesene and ratios of squalane to impurities for the catalytic loadings tested.

TABLE 6

Catalyst loadings using PPh₃ as ligand

| Entry # | Cat. | Conv (%) | Squ- alane (%) | Others (%) | Squ- alane Ratio |
|---|---|---|---|---|---|
| S/C 125/1 | | | | | |
| 1 | Pd(acac)₂ + 2.8 Ph₃P, IPA | 93 | 87 | 6 | 23/1 |
| 2 | Pd(Ph₃P)₂Cl₂, IPA, 20 mol % HCO₂Na | 97 | 91 | 6 | 25/1 |
| 3 | Pd(cod)Cl₂ + 2 Ph₃P, IPA, 20 mol % HCO₂Na | 95 | 89 | 6 | 24/1 |

TABLE 6-continued

Catalyst loadings using PPh3 as ligand

| Entry # | Cat. | Conv (%) | Squalane (%) | Others (%) | Squalane Ratio |
|---|---|---|---|---|---|
| 4 | (Ph3P)Pd(allyl)Cl, IPA 20 mol % HCO2Na | 94 | 86 | 8 | 22/1 |
| | S/C 250/1 | | | | |
| 5 | Pd(acac)2 + 2.8 Ph3P, IPA | 82 | 75 | 7 | 18/1 |
| 6 | Pd(Ph3P)2Cl2, IPA, 20 mol % HCO2Na | 96 | 89 | 7 | 26/1 |
| 7 | Pd(cod)Cl2 + 2 Ph3P, IPA, 20 mol % HCO2Na | 96 | 90 | 6 | 24/1 |
| 8 | (Ph3P)Pd(allyl)Cl, IPA, 20 mol % HCO2Na | 94 | 87 | 7 | 23/1 |
| | S/C 500/1 | | | | |
| 9 | Pd(cod)Cl2 + 2 Ph3P, IPA, 20 mol % HCO2Na | 92 | 87 | 5 | 22/1 |
| 10 | Pd(cod)Cl2 + 2 Ph3P, IPA, 20 mol % HCO2Na | 91 | 85 | 6 | 21/1 |
| 11 | Pd(Ph3P)2Cl2, IPA, 20 mol % HCO2Na | 87 | 82 | 5 | 22/1 |
| 12 | (Ph3P)Pd(allyl)Cl, IPA, 20 mol % HCO2Na | 60 | 54 | 6 | 19/1 |
| 13 | (Ph3P)Pd(PhCH2NMe2)Cl, IPA, 20 mol % HCO2Na | 68 | 63 | 5 | 16/1 |
| | S/C 1000/1 | | | | |
| 14 | Pd(Ph3P)2Cl2, IPA, 20 mol % HCO2Na | 49 | 41 | 8 | 14/1 |
| 15 | (Ph3P)Pd(allyl)Cl, IPA, 20 mol % HCO2Na | 54 | 44 | 10 | 14/1 |

At S/C 125/1, the tested catalytic systems gave good results (Entries 1-4). However, at S/C 250/1, the system without the use of NaHCO2 was less effective (Entry 5), while other catalytic systems (Entries 6-8) gave good conversion with a stable squalane ratios above 20/1. At S/C 500/1 two catalytic systems, Pd(Ph3P)2Cl2 and in situ Pd(cod)Cl2+2 Ph3P, gave high conversion, although lower squalane ratios were observed. Finally, at S/C 1000/1, only about 50% conversion of β-farnesene as observed with a 14/1 squalane ratio.

Catalyst loading was tested using another ligand m-Tol3P. The reaction conditions described above for PPh3 ligand were used. The results are presented in Table 7.

TABLE 7

Catalyst loadings using m-Tol3P as ligand

| Entry # | Cat. | Conv (%) | Squalane (%) | Others (%) | Squalane Ratio |
|---|---|---|---|---|---|
| | S/C 125/1 | | | | |
| 1 | Pd(acac)2 + 2.8 mTol3P IPA | 91 | 86 | 5 | 21/1 |
| 2 | (mTol3P)Pd(allyl)Cl IPA, 20 mol % HCO2Na | 99 | 94 | 5 | 23/1 |
| | S/C 250/1 | | | | |
| 1 | Pd(acac)2 + 2.8 mTol3P IPA | 79 | 67 | 12 | 9/1 |
| 2 | (mTol3P)Pd(allyl)Cl IPA, 20 mol % HCO2Na | 98 | 93 | 5 | 22/1 |
| | S/C 500/1 | | | | |
| 1 | (mTol3P)Pd(allyl)Cl IPA, 20 mol % HCO2Na | 55 | 43 | 12 | 9/1 |
| 2 | Pd(m-Tol3P)2Cl2 IPA, 20 mol % HCO2Na | 93 | 88 | 5 | 22/1 |

Similar results were obtained with m-Tol3P. Greater than 90% conversion of β-farnesene was obtained with squalane ratio greater than 20/1 at S/C of 500/1.

The catalyst loading was further reduced to S/C of 500/1 in the presence of formate. As good results in terms of selectivity for isosqualene were obtained using a preformed catalyst Pd(PPh3)2Cl2, this catalyst was chosen for the following study of reactions parameters.

Example 7

Nature of the Solvent

In this example, several solvents were tested for their effect on coversion of β-farnesene. A phase transfer catalyst (Bu4N, Cl) was used in order to favour the solubility of sodium formate.

Experimental procedure: the catalyst was weighed in a glass liner under inert atmosphere (S/C 125/1), 2 mL solvent was added followed by β-farnesene (5104 mL, 2.5 mmol, [c]=1M). The reaction was heated at 85° C. for 7 hours. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 8 are presented after the steps: (1) the coupling to obtain isosqualene, followed by (2) hydrogenation to obtain squalane. Data provided in Table 8 includes the % conversion of β-farnesene and ratios of squalane to impurities for the solvent tested.

TABLE 8

Pd(PPh$_3$)$_2$Cl$_2$ at S/C 125/1 - Solvent at 85° C.

| Entry # | Conditions | Solvent | Conv (%) | Squalane (%) | Others (%) | Squalane Ratio |
|---|---|---|---|---|---|---|
| 1 | Pd(PPh$_3$)$_2$Cl$_2$ IPA, 20 mol % HCO$_2$Na, "Bu$_4$NCl 10 mol % [c] = 1M, 85° C. | n-PrOH | 99 | 88 | 11 | 9/1 |
| 2 | Pd(PPh$_3$)$_2$Cl$_2$ IPA, 20 mol % HCO$_2$Na, "Bu$_4$NCl 10 mol % [c] = 1M, 85° C. | H$_2$O 1/ IPA 1 | 98 | 91 | 7 | 16/1 |
| 3 | Pd(PPh$_3$)$_2$Cl$_2$ IPA, 20 mol % HCO$_2$Na, "Bu$_4$NCl 10 mol % [c] = 1M, 85° C. | IPA | 87 | 83 | 4 | 21/1 |
| 4 | Pd(PPh$_3$)$_2$Cl$_2$ IPA, 20 mol % HCO$_2$Na, "Bu$_4$NCl 10 mol % [c] = 1M, 85° C. | DMF | 63 | 57 | 6 | 11/1 |
| 5 | Pd(PPh$_3$)$_2$Cl$_2$ IPA, 20 mol % HCO$_2$Na, "Bu$_4$NCl 10 mol % [c] = 1M, 85° C. | Butanone | 13 | 7 | 6 | 3/1 |
| 6 | Pd(PPh$_3$)$_2$Cl$_2$ IPA, 20 mol % HCO$_2$Na, "Bu$_4$NCl 10 mol % [c] = 1M, 85° C. | Toluene | 8 | 2 | 6 | — |
| 7 | Pd(PPh$_3$)$_2$Cl$_2$ IPA, 20 mol % HCO$_2$Na, "Bu$_4$NCl 10 mol % [c] = 1M, 85° C. | AcOiPr | 8 | — | 8 | — |
| 8 | Pd(PPh$_3$)$_2$Cl$_2$ IPA, 20 mol % HCO$_2$Na, "Bu$_4$NCl 10 mol % [c] = 1M, 85° C. | dioxane | 6 | 3 | 3 | — |
| 9 | Pd(PPh$_3$)$_2$Cl$_2$ IPA, 20 mol % HCO$_2$Na, "Bu$_4$NCl 10 mol % [c] = 1M, 85° C. | DCE | 6 | 3 | 3 | — |
| 10 | Pd(PPh$_3$)$_2$Cl$_2$ IPA, 20 mol % HCO$_2$Na, "Bu$_4$NCl 10 mol % [c] = 1M, 85° C. | AcN | 5 | 2 | 3 | — |

As demonstrated by the data, the protic solvents gave β-farnesene conversion above 85% (Entries 1-3). Furthermore, DMF and butanone gave β-farnesene conversions of 63% and 13%, respectively (Entries 4-5). For the other solvents tested, lower β-farnesene conversions (Entries 6-10) was observed. In terms of squalane ratios, primary alcohols and IPA/H$_2$O mixture gave ratios of 9/1 and 16/1, respectively.

Alcoholic solvents described in Table 9 were also tested for this reaction.

Experimental procedure: the catalyst was weighed in a glass liner under inert atmosphere (S/C 125/1), 2 mL solvent was added followed by β-farnesene (510 μL mL, 2.5 mmol, [c]=1M). The reaction was heated at 85° C. for 7 hours. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 9 are presented after the steps: (1) the coupling to obtain isosqualene, followed by (2) hydrogenation to obtain squalane.

TABLE 9

Pd(PPh$_3$)$_2$Cl$_2$ at S/C 125/1 - Solvent at 85° C. without TBAC ("Bu$_4$NCl)

| Entry # | Conditions | Solvent | Conv (%) | Squalane (%) | Others (%) | Squalane Ratio |
|---|---|---|---|---|---|---|
| 1 | Pd(PPh$_3$)$_2$Cl$_2$ IPA, 20 mol % HCO$_2$Na, [c] = 1M, 85° C. | n-PrOH | 84 | 70 | 14 | 5/1 |
| 2 | Pd(PPh$_3$)$_2$Cl$_2$ IPA, 20 mol % HCO$_2$Na, [c] = 1M, 85° C. | n-BuOH | 98 | 90 | 8 | 12/1 |
| 3 | Pd(Ph$_3$P)$_2$Cl$_2$ IPA, 20 mol % HCO$_2$Na, [c] = 1M, 85° C. | IPA | 94 | 89 | 5 | 22/1 |

TABLE 9-continued

Pd(PPh$_3$)$_2$Cl$_2$ at S/C 125/1 - Solvent at 85° C. without TBAC ("Bu$_4$NCl)

| Entry # | Conditions | Solvent | Conv (%) | Squalane (%) | Others (%) | Squalane Ratio |
|---|---|---|---|---|---|---|
| 4 | Pd(PPh$_3$)$_2$Cl$_2$ IPA, 20 mol % HCO$_2$Na, [c] = 1M, 85° C. | 2-BuOH | 58 | 51 | 7 | 19/1 |
| 5 | Pd(PPh$_3$)$_2$Cl$_2$ IPA, 20 mol % HCO$_2$Na, [c] = 1M, 85° C. | 3-Me-2-BuOH | 16 | 13 | 3 | 25/1 |
| 6 | Pd(PPh$_3$)$_2$Cl$_2$ IPA, 20 mol % HCO$_2$Na, [c] = 1M, 85° C. | t-BuOH | 10 | 6 | 4 | 25/1 |

Among the solvents tested, primary alcohols such as n-PrOH and n-BuOH gave β-farnesene conversions of 84 and 98%, respectively (Entries 1-2), with the squalane ratios of 5/1 and 12/1, respectively. Secondary alcohol, isopropyl alcohol, gave β-farnesene conversion of 94% with squalane ratio of 22/1 (Entry 3). However, with more hindered secondary alcohols, 2-butanol and 3-methyl-2-butanol, (entries 4-5), β-farnesene conversions of 58% and 16%, respectively, were observed. The squalane ratios were 19/1 and 25/1, respectively. Tert-BuOH gave β-farnesene conversion of 10% with a 25/1 squalane ratio (Entry 5).

Example 8

Temperature

The effect of temperature was tested using a Biotage Endeavor that allows the reactions to be performed at higher temperature in a sealed environment. Results are presented in Table 10.

Experimental procedure: the catalyst was weighed in a glass liner under inert atmosphere (S/C 125/1), 2 mL IPA was added followed by β-farnesene (5104 mL, 2.5 mmol, [c]=1M). The reaction was heated as indicated in Table 10. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 10 are presented after the steps: (1) the coupling to obtain isosqualene, followed by (2) hydrogenation to obtain squalane. Data provided in Table 9 includes the % conversion of β-farnesene and ratios of squalane to impurities for the temperatures tested.

TABLE 10

Pd(PPh$_3$)$_2$Cl$_2$ at S/C 125/1 - Temperature

| Entry # | Cat. | Conv (%) | Squalane (%) | Others (%) | Squalane Ratio |
|---|---|---|---|---|---|
| 1 | Pd(Ph$_3$P)$_2$Cl$_2$ IPA, 20 mol % HCO$_2$Na, [c] = 1M, 60° C. | 65 | 58 | 7 | 11/1 |
| 2 | Pd(Ph$_3$P)$_2$Cl$_2$ IPA, 20 mol % HCO$_2$Na, [c] = 1M, 75° C. | 95 | 88 | 7 | 14/1 |
| 3 | Pd(Ph$_3$P)$_2$Cl$_2$ IPA, 20 mol % HCO$_2$Na, [c] = 1M, 85° C. | 98 | 93 | 5 | 19/1 |
| 4 | Pd(Ph$_3$P)$_2$Cl$_2$ IPA, 20 mol % HCO$_2$Na, [c] = 1M, 95° C. | 88 | 83 | 5 | 18/1 |

TABLE 10-continued

Pd(PPh$_3$)$_2$Cl$_2$ at S/C 125/1 - Temperature

| Entry # | Cat. | Conv (%) | Squalane (%) | Others (%) | Squalane Ratio |
|---|---|---|---|---|---|
| 5 | Pd(Ph$_3$P)$_2$Cl$_2$ IPA, 20 mol % HCO$_2$Na, [c] = 1M, 110° C. | 89 | 85 | 5 | 21/1 |

Temperatures ranging form 60° C. to 110° C. were tested in a Biotage Endeavor. At lower temperature (60° C.), β-farnesene conversion of 65% with squalane ratio of 11/1 was observed (Entry 1). From 75° C. to 95° C., β-farnesene conversions of 95%, 98%, and 88% were obtained (Entries 2-5). By increasing the temperature to 110° C., the squalane ratio increased from 14/1 at 75° C. to 21/1 at 110° C. (at the exception of the run at 95° C. that gave 18/1 ratio).

Example 9

Amount of Formate and Substrate Concentration

The effect of formate concentration and the substrate concentration were also tested.

Experimental procedure: the catalyst was weighed in a glass liner under inert atmosphere (S/c 125/1), 2 mL IPA was added followed by β-farnesene (510 µL mL, 2.5 mmol, [c]=1M). The reaction was heated at 85° C. for 7 hours. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 11 are presented after the steps: (1) the coupling to obtain isosqualene, followed by (2) hydrogenation to obtain squalane. Data provided in Table 11 includes the % conversion of β-farnesene and ratios of squalane to impurities for the reaction parameters tested.

TABLE 11

Pd(PPh₃)₂Cl₂ at S/C 125/1 - reaction parameters

| Entry # | Cat. | Conv (%)[a] | Squalane (%) | Others (%)[a] | Squalane Ratio |
|---|---|---|---|---|---|
| 1 | Pd(Ph₃P)₂Cl₂ IPA, 20 mol % HCO₂Na, [c] = 0.75M | 87 | 82 | 5 | 20/1 |
| 2 | Pd(Ph₃P)₂Cl₂ IPA, 20 mol % HCO₂Na, [c] = 1M | 94 | 89 | 5 | 22/1 |
| 3 | Pd(Ph₃P)₂Cl₂ IPA, 20 mol % HCO₂Na, [c] = 1.25M | 94 | 87 | 7 | 22/1 |
| 4 | Pd(Ph₃P)₂Cl₂ IPA, 5 mol % HCO₂Na, [c] = 1M | 88 | 83 | 5 | 20/1 |
| 5 | Pd(Ph₃P)₂Cl₂ IPA, 50 mol % HCO₂Na, [c] = 1M | 93 | 89 | 4 | 22/1 |

At 0.75M substrate concentration, 87% β-farnesene conversion and 20/1 squalane ratio were obtained (Entry 1). By increasing the substrate concentrations to 1M and 1.25, β-farnesene conversion of 94% and squalane ratio of 22/1 were obtained (Entries 2-3).

The amount of NaHCO₂ was tested using 5-mol %, 20-mol % (benchmark) and 50-mol % (Entries 4, 2, 5). Using 5 mol %, β-farnesene conversion of 88% and squalane ratio of 20/1 were obtained (Entry 4). By increasing the amount of NaHCO₂ to 20 mol % and 50 mol %, β-farnesene conversion of 94% and squalane ratio of 22/1, respectively, were obtained (Entry 2-5).

Example 10

Catalyst Loading

In this example, the influence of the catalyst loading on the squalane ratio was tested.

Experimental procedure: the catalyst was weighed in a glass liner under inert atmosphere, 2 mL solvent was added followed by β-farnesene (510 μL mL, 2.5 mmol, [c]=1 M). The reaction was heated at 85° C. for 7 hours. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 3 are presented after the steps: (1) the coupling to obtain isosqualene, followed by (2) hydrogenation to obtain squalane. Data provided in Table 12 includes the % conversion of β-farnesene and ratios of squalane to impurities for the catalyst loadings tested.

TABLE 12

Pd(PPh₃)₂Cl₂ at various catalyst loading

| Entry # | Conditions | S/C | Conv (%) | Squalane (%) | Others (%) | Squalane Ratio |
|---|---|---|---|---|---|---|
| 1 | Pd(PPh₃)₂Cl₂ IPA, 20 mol % HCO₂Na, [c] = 1M, 85° C. | 125/1 | 94 | 89 | 6 | 21/1 |
| 2 | Pd(PPh₃)₂Cl₂ IPA, 20 mol % HCO₂Na, [c] = 1M, 85° C. | 100/1 | 94 | 90 | 4 | 22/1 |
| 3 | Pd(PPh₃)₂Cl₂ IPA, 20 mol % HCO₂Na, [c] = 1M, 85° C. | 75/1 | 95 | 90 | 5 | 23/1 |
| 4 | Pd(PPh₃)₂Cl₂ IPA, 20 mol % HCO₂Na, [c] = 1M, 85° C. | 50/1 | 90 | 83 | 7 | 20/1 |

In all cases, β-farnesene conversion was above 90%. The conversion decreased to 90% at higher catalyst loading (S/C 50/1) (Entry 5). A squalane ratio of 23/1 was reached at a S/C of 75/1 and then decreased to 20/1 at a S/C of 50/1.

A catalyst loading of S/C 75/1 at higher temperature was tested. Results are presented in Table 13.

Experimental procedure: the catalyst was weighed in a glass liner under inert atmosphere, 2 mL solvent was added followed by β-farnesene (510 μL mL, 2.5 mmol, [c]=1M). The reaction was heated at 100° C. and 120° C. for 7 hours. The hydrogenation reaction was carried out as described in Example 1.

TABLE 13

Pd(PPh₃)₂Cl₂ at S/C 75/1 and higher temperature

| Entry # | Conditions | Solvent | Conv (%)$^a$ | Squalane (%)$^a$ | Others (%)$^a$ | Squalane Ratio$^{b)}$ |
|---|---|---|---|---|---|---|
| 1 | Pd(PPh₃)₂Cl₂ IPA, 20 mol % HCO₂Na, [c] = 1M, 100° C. | IPA | 68 | 51 | 17 | 11/1 |
| 2 | Pd(PPh₃)₂Cl₂ IPA, 20 mol % HCO₂Na, [c] = 1M, 120° C. | IPA | 65 | 35 | 30 | 7/1 |

Two reactions showed β-farnesene conversion of 68% and 65%, and 17% and 30% by-products formation, respectively. The squalane ratio was 11/1 and 7/1, respectively.

Example 11

Other Parameters

Further reaction parameters were tested such as addition of extra ligand and use of different formate sources.

Experimental procedure: the catalyst was weighed in a glass liner under inert atmosphere, 2 mL IPA was added followed by β-farnesene (510 μL mL, 2.5 mmol, [c]=1 M). The reaction was heated at 85° C. for 7 hours. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 14 are presented after the steps: (1) the coupling to obtain isosqualene, followed by (2) hydrogenation to obtain squalane.

TABLE 14

Pd(PPh₃)₂Cl₂ at S/C 125/1 - reaction parameters

| Entry # | Cat. | Conv (%) | Squalane (%) | Others (%) | Squalane Ratio |
|---|---|---|---|---|---|
| 1 | Pd(Ph₃P)₂Cl₂ IPA, 20 mol % HCO₂Na, [c] = 1M | 94 | 89 | 5 | 22/1 |
| 2 | Pd(Ph₃P)₂Cl₂ + 2PPh₃ IPA, 20 mol % HCO₂Na [c] = 1M | 16 | 11 | 5 | 18/1 |
| 3 | Pd(Ph₃P)₂Cl₂ IPA, 20 mol % HCO₂K [c] = 1M | 91 | 86 | 5 | 20/1 |
| 4 | Pd(Ph₃P)₂Cl₂ IPA, 20 mol % HCO₂Na, 10 mol % Bu₄NCl, [c] = 1M | 93 | 88 | 5 | 19/1 |
| 5 | Pd(Ph₃P)₂Cl₂ IPA, 20 mol % HCO₂Na, 20 mol % PEG, [c] = 1M | 94 | 88 | 6 | 20/1 |
| 6 | Pd(Ph₃P)₂Cl₂ IPA, 20 mol % HCO₂, NH₄ [c] = 1M | 40 | 14 | 26 | 1/1 |
| 7 | Pd(Ph₃P)₂Cl₂ IPA, 20 mol % HCO₂H/NEt₃, [c] = 1M | 13 | 5 | 8 | 1/1 |
| 8 | Pd(Ph₃P)₂Cl₂ IPA, 20 mol % HCO₂H, [c] = 1M | — | — | — | — |

Figure 2:
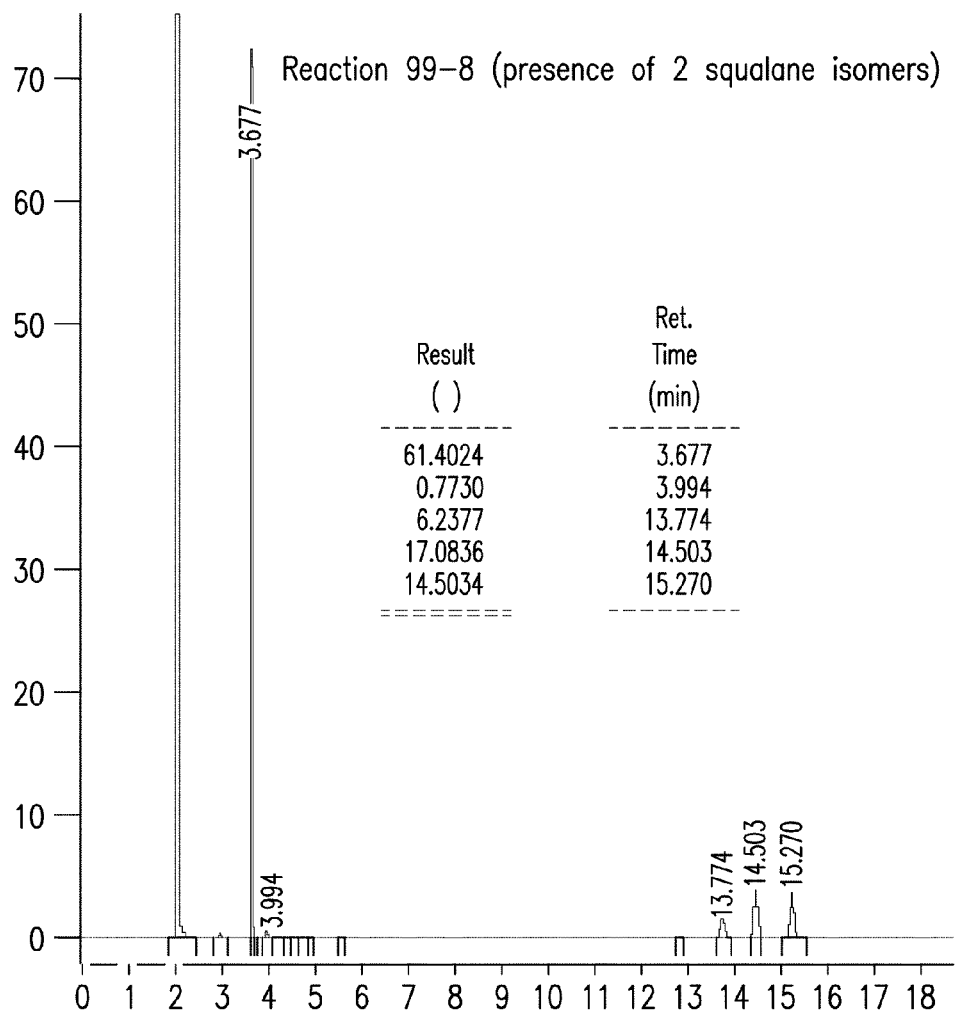
FIG. 2 provides a GC spectrum for a reaction described in Table 14, entry 6.

By adding 2 eq. of PPh₃, 16% β-farnesene conversion was observed (Entry 2). The squalane ratio was 18/1. Potassium formate as the formate source showed 91% β-farnesene conversion and the squalane ratio of 20/1 (Entries 3). The use of additives such as Bu₄NCl or PEG did not increase the conversion and the squalane ratio (Entries 4-5). A formic acid/amine system gave 13% β-farnesene conversion and squalane ratio of 1/1 (Entries 6). FIG. 2 provides a GC spectrum for the reaction described in Table 14, entry 6. NH₄HCO₂ gave 13% conversion and squalane ratio of 1/1 (Entry 7). Finally, no conversion of β-farnesene was observed with formic acid (Entry 8).

Example 12

Background Reaction

The nature of catalytic species was tested by using a blank reaction without the use of phosphine ligand (Table 15).

Experimental procedure: the catalyst was weighed in a glass liner under inert atmosphere, 2 mL IPA was added followed by β-farnesene (510 μL mL, 2.5 mmol, [c]=1 M). The reaction was heated at 85 and 120° C. for 7 hours as indicated in Table 15. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 15 are presented after the steps: (1) the coupling to obtain isosqualene, followed by (2) hydrogenation to obtain squalane.

TABLE 15

Test no ligand with 20% HCO₂Na/Pd(cod)Cl₂

| Entry # | Cat. | Conv (%) | Squalane (%) | Others (%) | Squalane Ratio |
|---|---|---|---|---|---|
| 1 | Pd(cod)Cl₂ + 2 Ph₃P IPA, 20 mol % HCO₂Na [c] = 1M, 85° C. | 96 | 89 | 7 | 23/1 |
| 2 | Pd(cod)Cl₂ IPA, 20 mol % HCO₂Na [c] = 1M, 85° C. | 25 | 20 | 5 | 4/1 |
| 3 | Pd(cod)Cl₂ IPA, 20 mol % HCO₂Na, [c] = 1M, 120° C. | 50 | 20 | 30 | 0.8/1 |

According to the results presented in Table 15, a background reaction was clearly present. This reaction involved a Pd(0) without any ligand, as the reaction performed in Entry 2, show 25% β-farnesene conversion and squalane ratio of 4 to 1 (Entry 2). At 120° C., the conversion is 50%, the squalane ratio is 0.8 to 1 with the main impurity becoming the major squalane derivative (Entry 3).

Example 13

Reaction Time and Delayed Addition

The effect of the reaction time and the order of addition on the squalane ratio was tested (Table 16).

Experimental procedure: the catalyst was weighed in a glass liner under inert atmosphere, 2 mL solvent was added followed by β-farnesene (510 μL mL, 2.5 mmol, [c]=1 M). The reaction was heated at 85° C. for the time indicated in Table 16. The hydrogenation reaction was carried out as described in Example 1.

The reactions were analyzed by gas chromatography. The following peaks were observed: farnesane at 3.9 min, squalane at 15.2 min, and isosqualane 14.6 min.

The results in Table 16 are presented after the steps: (1) the coupling to obtain isosqualene, followed by (2) hydrogenation to obtain squalane.

TABLE 16

| | $Pd(PPh_3)_2Cl_2$ at S/C 125/1 | | | | | |
|---|---|---|---|---|---|---|
| Entry # | Conditions | Solvent | Conv (%) | Squalane (%) | Others (%) | Squalane Ratio |
| 1 | $Pd(PPh_3)_2Cl_2$ IPA, 20 mol % $HCO_2Na$, [c] = 1M, 85° C. | IPA/1 h | 40 | 32 | 8 | 17/1 |
| 2 | $Pd(PPh_3)_2Cl_2$ IPA, 20 mol % $HCO_2Na$, [c] = 1M, 85° C. | IPA/3 h | 50 | 44 | 6 | 18/1 |
| 3 | $Pd(PPh_3)_2Cl_2$ IPA, 20 mol % $HCO_2Na$, [c] = 1M, 85° C. | IPA/7 h | 80 | 74 | 6 | 19/1 |
| 4 | $Pd(PPh_3)_2Cl_2$ IPA, 20 mol % $HCO_2Na$, [c] = 1M, 85° C. | IPA/7 h Farnesene after 15' | 70 | 63 | 7 | 18/1 |
| 5 | $Pd(PPh_3)_2Cl_2$ IPA, 20 mol % $HCO_2Na$, [c] = 1M, 85° C. | IPA/7 h $NaHCO_2$ after 15' | 69 | 62 | 7 | 21/1 |

The β-farnesene conversion was 40% and the squalane ratio was 17/1 for the reaction time of 1 hour (Entry 1). The β-farnesene conversion was 50% and the squalane ratio was 18/1 when the reaction time of 3 hour (Entry 2). The β-farnesene conversion was 80% and the squalane ratio was 19/1 when the reaction time of 7 hour (Entry 3). The addition of the farnesene after 15 min at 85° C. reduced the conversion to 70% and the squalane ratio to 18/1 (Entry 4). Finally, the late addition of $NaHCO_2$ gave conversion of 69%, and the squalane ratio of 21/1 (Entry 5).

Example 14

Nickel Catalysts

In this example, preformed or in situ generated nickel catalysts were tested (Table 17).

Experimental procedure: the catalyst was weighed in a glass liner under inert atmosphere (S/C 125/1), 2 mL solvent was added followed by β-farnesene (510 μL mL, 2.5 mmol, [c]=1M). The hydrogenation reaction was carried out as described in Example 1.

The reactions were analyzed by gas chromatography. The following peaks were observed: farnesene at 4.1 min, isosqualene at 20.1 min, and partially reduced isosqualene impurity between 16 min and 20 min.

TABLE 17

| | nickel catalysts | | | | | |
|---|---|---|---|---|---|---|
| Entry # | Cat. | Solvent | Conv (%) | Iso-squalene (%) | Others (%) | Squalane Ratio |
| 1 | $Ni(PPh_3)_4$ | IPA | 1 | — | 1 | |
| 2 | $Ni(PPh_3)_4$ | Tol | 2 | — | 2 | |
| 3 | $Ni(PPh_3)_4$ | THF | 2 | — | 2 | |

TABLE 17-continued nickel catalysts

| Entry # | Cat. | Solvent | Conv (%) | Iso-squalene (%) | Others (%) | Squalane Ratio |
|---|---|---|---|---|---|---|
| 4 | Ni(PPh$_3$)$_2$Cl$_2$ + 5 Eq tBuONa | IPA | 2 | — | 2 | |
| 5 | Ni(PPh$_3$)$_2$Cl$_2$ + 30 Eq Zn THF(0.5 mL) + farnesene 15 min | IPA | 2 | 0 | 2 | |
| 6 | Ni(PPh$_3$)$_2$Cl$_2$ + 2.5 eq BuLi THF(1 mL) 15 min | IPA | 1 | — | 1 | |
| 7 | Ni(PPh$_3$)$_2$Cl$_2$ + 2.5 eq BuLi THF(0.5 mL) + farnesene 15 min | IPA | 3 | 0 | 3 | |
| 8 | Ni(PPh$_3$)$_2$Cl$_2$ + 2.5 eq iPrMgXi THF(1 mL) 15 min | IPA | 1 | — | 1 | |
| 9 | Ni(PPh$_3$)$_2$Cl$_2$ + 2.5 eq iPrMgXi THF(0.5 mL) + farnesene 15 min | IPA | 2 | 0 | 2 | |
| 10 | Ni(PPh$_3$)$_2$Cl$_2$ + 2.5 eq Me$_2$Zn THF(1 mL) 15 min | IPA | 1 | — | 1 | |
| 11 | Ni(PPh$_3$)$_2$Cl$_2$ + 2.5 eq Me$_2$Zn THF(0.5 mL) + farnesene 15 min | IPA | 2 | 0 | 2 | |
| 12 | Ni(acac)$_2$ 2.5 eq BuLi in THF(1 mL) 15 min. Then 2 PPh$_3$ | IPA | 16 | — | 16 | |
| 13 | Ni(COD)$_2$ + 1 eq PPh$_3$ | IPA | 3 | 1 | 2 | |
| 14 | Ni(COD)$_2$ + 1 eq PPh$_3$ | THF | 3 | — | 3 | |
| 15 | Ni(COD)$_2$ + 1 eq PPh$_3$ (scale X 3) | neat | 3 | — | 3 | |
| 16 | Ni(COD)$_2$ + 1 eq PEt$_3$ | IPA | 12 | 6 | 6 | |
| 17 | Ni(COD)$_2$ + 1 eq Ph$_2$PO—(CH$_2$)$_2$—NMe$_2$ | IPA | 2 | — | 2 | |
| 18 | Ni(COD)$_2$ + 1 eq PhPCy$_2$ | IPA | 50 | 7 | 43 (25*) | |
| | After hydrogenation with Pd/C | | 70 | 12 | 60 | 0.25/1 |
| 19 | Ni(COD)$_2$ + 1 eq PCy$_3$ | IPA | 37 | 4 | 33 (20*) | |
| | After hydrogenation with Pd/C | | 50 | 7 | 43 | 0.2/1 |
| 20 | Ni(COD)$_2$ + 1.3 eq. PhPCy$_2$ | IPA | 70 | | | 0.29/1 |

(*)Amount of impurity between 16 min and 20 min (the impurity is mostly neosqualane and some partially reduced isosqualene).

Figure 3:
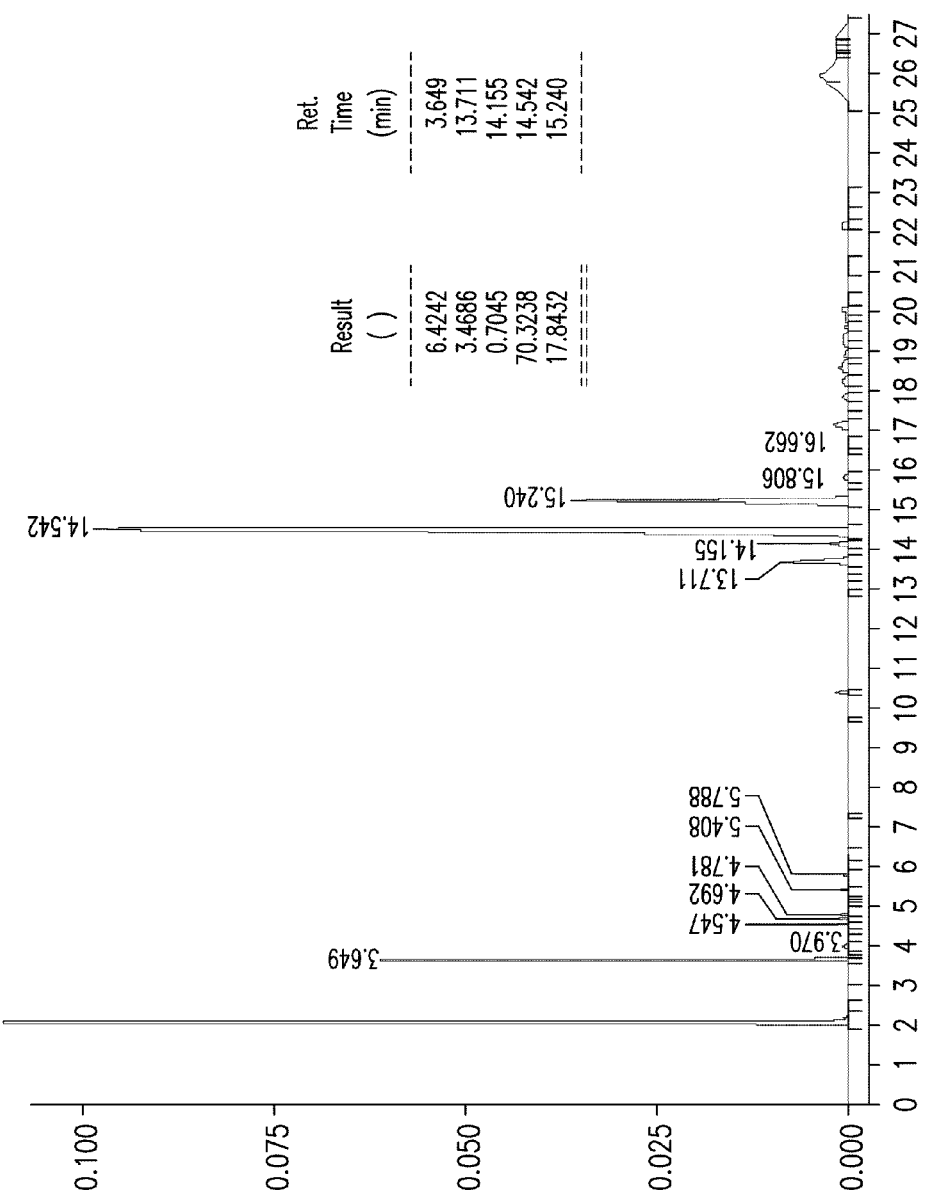
FIG. 3 provides a GC spectrum for a reaction described in Table 17, entry 19.
Figure 4:
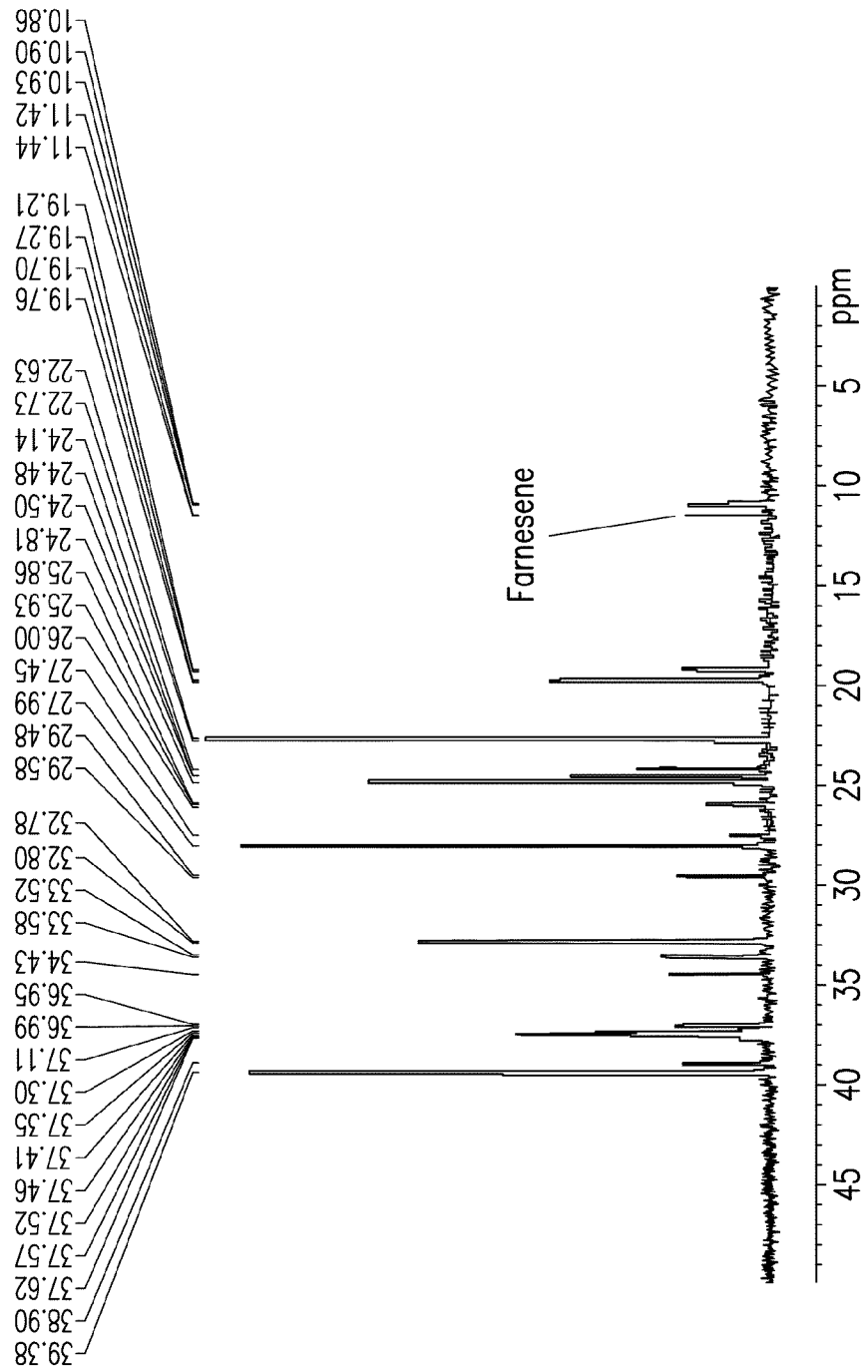
FIG. 4 provides a $^{13}$C NMR spectrum for a reaction described in Table 17, entry 19.
Figure 5:
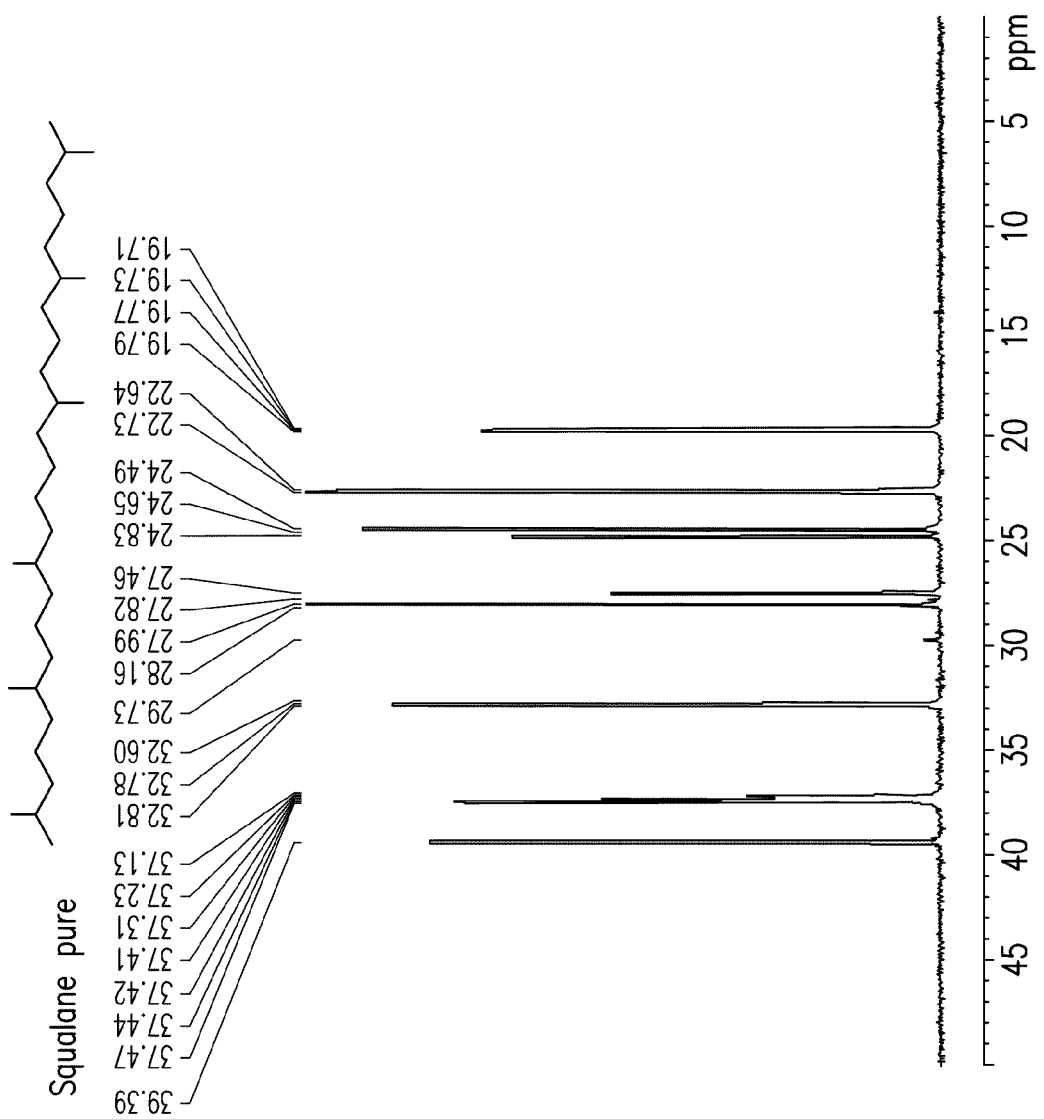
FIG. 5 provides a $^{13}$C NMR spectrum for squalane.

Using a Ni(PPh$_3$)$_4$, 1-2% conversion was obtained in three different solvents (Entries 1-3). Starting from a Ni(PPh$_3$)$_2$Cl$_2$ with a reducing agent in the presence of farnesene that would have stabilized the Ni(0), 1-3% conversion was observed (Entries 4-11). The reduction in situ of Ni(acac)$_2$ with BuLi in THF and then addition of the phosphine gave 16% conversion with no squalane (Entry 12). Using Ni(cod)$_2$ and PPh$_3$, 3% conversion was observed (Entries 13-15). Using Ni(cod)$_2$ and PEt$_3$, 12% conversion was observed (Entries 16). Using Ni(cod)$_2$ and PhPCy$_2$, 2% conversion was observed (Entries 17). Using Ni(cod)$_2$ and PCy$_3$, 50% conversion was observed (Entries 18). A number of signals were obtained in the isosqualene region and after hydrogenation the opposite selectivity was observed (Entry 18). FIG. 3 provides a GC spectrum for the reaction described Entry 19. These crude reactions were analyzed by NMR in order to identify the squalane impurity. The $^{13}$C NMR provided in FIG. 4 clearly indicates the presence of a CH$_3$—CH$_2$— motif in this impurity.

Entry 20 was prepared according to the following procedure. To a 1000 mL round bottom flask equipped with a magnetic stir bar was added β-farnesene (92.30 g, 451.7 mmol) and 400 mL of isopropyl alcohol. The mixture was placed under vacuum (100 torr) at room temperature for 40 minutes. Bis(1,5-cyclooctadiene)nickel(0) (0.8289 g, 3.0135 mmol) and dicyclohexylphenylphosphine (1.0818 g, 3.9426 mmol) were quickly weighed and added to the farnesene-IPA mixture. The reaction mixture was placed under vacuum and N$_2$ was added. The reaction mixture was heated at 94° C. overnight. GCMS showed about 70% (area percent) conversion to linear dimers. After the flask cooled to ambient temperature the mixture was concentrated under vacuum; the resulting concentrate was filtered through a short silica column and the column rinsed with hexanes. The filtrate was concentrated in vacuo resulting a clear, light yellow oil (87.2 g). Linear farnesene dimers (37.42 g, 91.22 mmol) were hydrogenated over 5% Pd/C (1.1234 g, 3.002 w/w %) at 1000 psi H$_2$ and 85° C. The reaction mixture was diluted in hexanes and filtered through a short silica column; the filtrate was concentrated under vacuum resulting a clear colorless oil (35.9477 g). The reduced linear dimers were purified on a Kugelrohr apparatus in two steps. To remove the C15s from the dimers/heavies mixture, the sample was distilled at 0.35 mm Hg and 165° C. To remove the linear dimers from the bottoms the sample was distilled at 0.05 mm Hg and 235° C. Mass balance: 54.9% linear dimers, 38.6% C15 compounds, 2.8% heavies. GCMS analysis of the isolated linear dimers shows no C15 compounds and two major compounds: isosqualane (66.5%) and squalane (19.6%).

Example 15

Comparative Example 1

Komatsu et al. in U.S. Pat. No. 3,794,692 and U.S. Pat. No. 3,859,374 reported preparation of squalane from β-farnesene in two steps. In the first step, β-farnesene is purportedly dimerized to provide a linear dimer, which is hydrogenated in the second step purportedly to yield squalane. However, the inventors of the '692 and '374 patents did not provide sufficient information to confirm the structure of their reaction products, or to verify the presence of squalane.

The '692 patent reports in its Example 3a dimerization reaction of farnesene (source, purity, and isomer of farnesene not specified) with bis(cyclooctadiene)nickel, tri-n-butylphosphine and isopropyl alcohol to produce a reaction product fraction with boiling point 210° C./0.3 mm Hg. The '692 patent asserts that the structure of the reaction product was confirmed to be

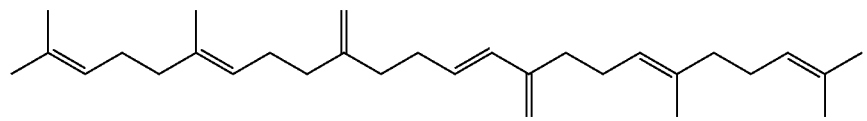 [SMILES: C=C(/C=C/CCC(=C)CC/C=C(\C)CCC=C(C)C)CC/C=C(\C)CCC=C(C)C]

by IR and NMR data, but provides no such data to confirm this structural assignment. Similarly, no data is provided to confirm their saturated hydrocarbon is squalane.

The '374 patent reports in its Example 5a dimerization reaction of farnesene (source, purity and isomer of farnesene not specified) with palladium nitrate, triphenylphosphine, sodium phenolate, isopropyl alcohol and isopropyl ether to form a linear dimer, which is asserted to be identical in structure to that as was reportedly formed in Example 3 of the '692 patent. No data confirming the structural assignment is provided in the '374 patent. The reported boiling point for the linear dimer in Example 5 of the '374 patent is 175-180° C./0.2 mm Hg, which appears to be about 30° C. lower than the boiling point (210° C./0.3 mm Hg) for the reportedly identical linear dimer in the '692 patent.

Akutagawa et al., *Bulletin of the Chemical Society of Japan*, v.51(4), p. 1158-62 (1978), is an extension of the work described in the '692 and '374 patents. Akutagawa et al. reports dimerization of linear trimers of isoprene and hydrogenation of the dimer to form squalane. They state that the linear trimers contain a mixture of β-farnesene and other products produced by catalytic oligomerization of isoprene. However, as described below in this Comparative Example 1, NMR data reported by Akutagawa et al. is not consistent with that of β-farnesene.

Akutagawa et al. dimerized the linear trimers with palladium nitrate, triphenylphosphine, and sodium o-methoxyphenolate in 2-propanol, to reportedly form farnesene dimer 19, which was subsequently hydrogenated to reportedly produce squalane. Farnesene dimer 19 has a structure identical to that reported as the linear dimer in Examples 3 and 5 of the '692 and '374 patents, respectively, and to isosqualene as described herein. Akutagawa et al. reports NMR data for farnesene dimer 19. However, as described in this Comparative Example 1, spectroscopic data for the dimerization reaction product obtained by Akutagawa et al. are not consistent with the presence of a compound having the structure of farnesene dimer 19 (isosqualene) in the product. Akutagawa et al. provides no spectroscopic data for the hydrogenated product to verify its structure as squalane.

Akutagawa et al. and the inventors of the '374 and '692 patents did not sufficiently characterize their reaction product to unambiguously assign structures to those reaction products, and they failed to demonstrate conclusively they had in hand the linear dimer isosqualene or squalane. In fact, Akutagawa et al.'s NMR data demonstrate otherwise—β-farnesene as a starting material was not produced as claimed and isosqualene as a dimerization product was not produced as claimed.

In this Comparative Example 1, the NMR data provided by Akutagawa et al. for linear trimer 1 was compared with β-farnesene having a purity of >97%, prepared by the method described in U.S. Pat. No. 7,399,323 B1.

Figure 6A:
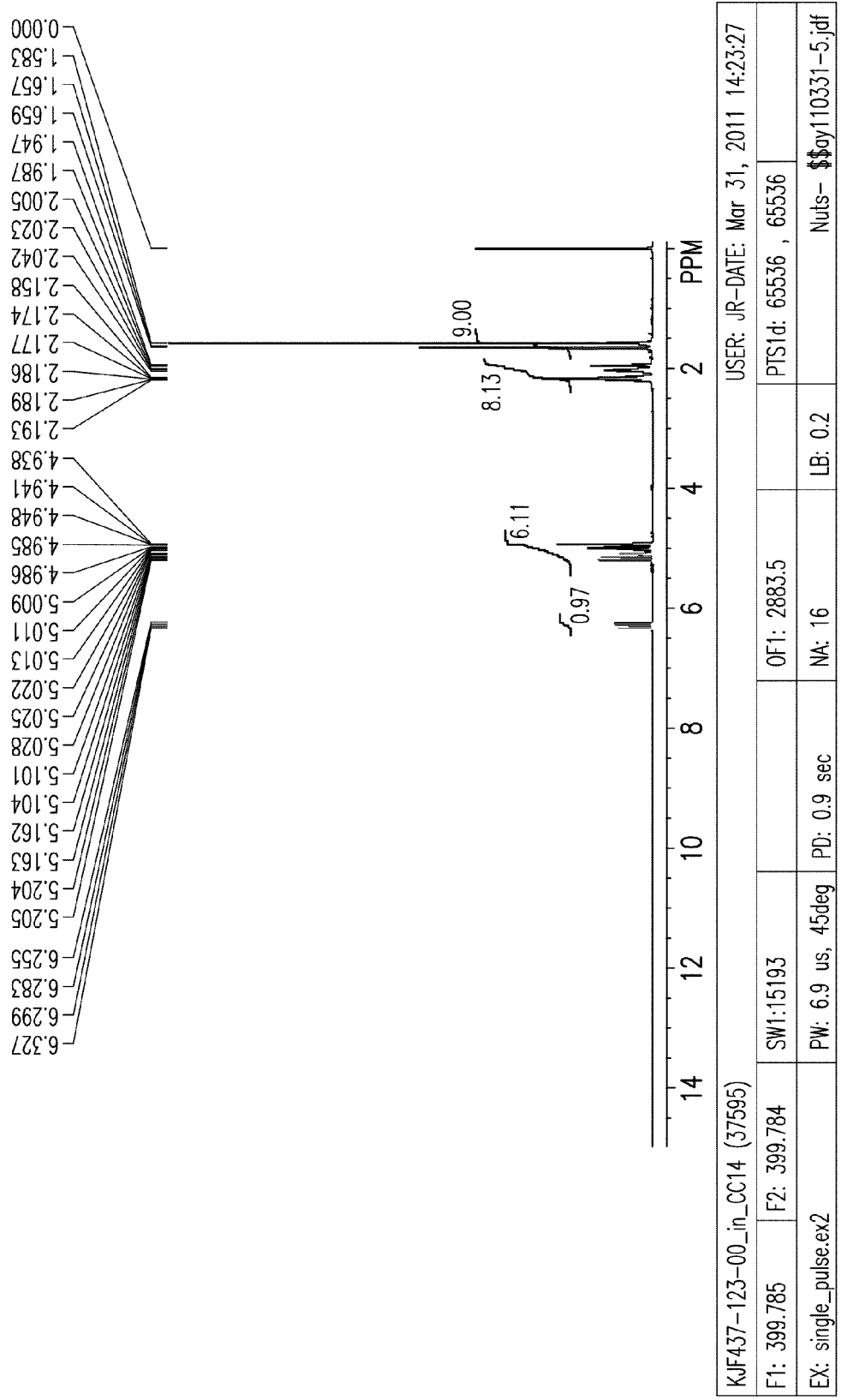
FIG. 6A provides a proton NMR spectrum of β-farnesene in carbon tetrachloride.

FIG. 6A provides an NMR spectrum for β-farnesene in carbon tetrachloride. A tabulation of the NMR spectral data is provided below in Table 18A:

TABLE 18A

| β-farnesene prepared by a method described in U.S. Pat. No. 7,399,323 Signal | Linear trimer 1 reported by Akutagawa et al. Signal |
|---|---|
| 6.291 ppm, doublet of doublets, 1H | 6.27, triplet, 1H |
| 5.183 ppm, doublet of doublets, 1H | 5.10, multiplet, 4H |
| 5.102, triplet, 1H | No peak reported |
| 5.00-5.03, multiplet, 2H | No peak reported |
| 4.944, doublet, 2H | 4.6, singlet, 2H* |
| 2.12-2.23, multiplet, 4H | 1.90-2.18, multiplet, 8H |
| 1.93-2.07, multiplet, 4H | No peak reported |
| 1.657, 1.659, singlet, 3H | 1.62-1.79, singlet, 6H* |
| 1.583, singlet, 6H | 1.59, singlet, 3H* |

Akutagawa et al.'s spectrum for their linear trimer 1 (to which they assign the structure for β-farnesene) does not match that of β-farnesene known to be 97% pure even though both spectra were recorded in carbon tetrachloride. Of particular note is the discrepancy between the two spectra are the three sets of resonances marked with an asterisk*. Based on this analysis, it does not appear that Akutagawa was working with β-farnesene.

In this Comparative Example 1, the NMR data provided for a dimerization reaction product by Akutagawa et al. in *Bulletin of the Chemical Society of Japan*, v.51(4), p. 1158-62 (1978) was compared with isosqualene prepared by a method provided herein.

To aid the comparison, the chemical structure of isosqualene with numbered hydrogen atoms is provided below:

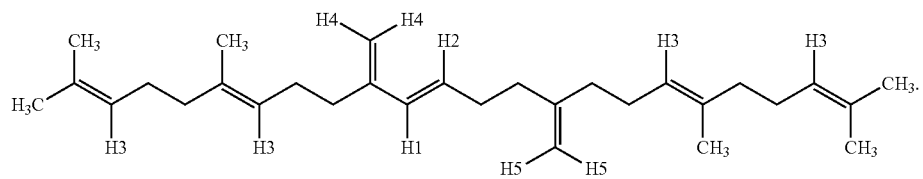

Figure 6B:
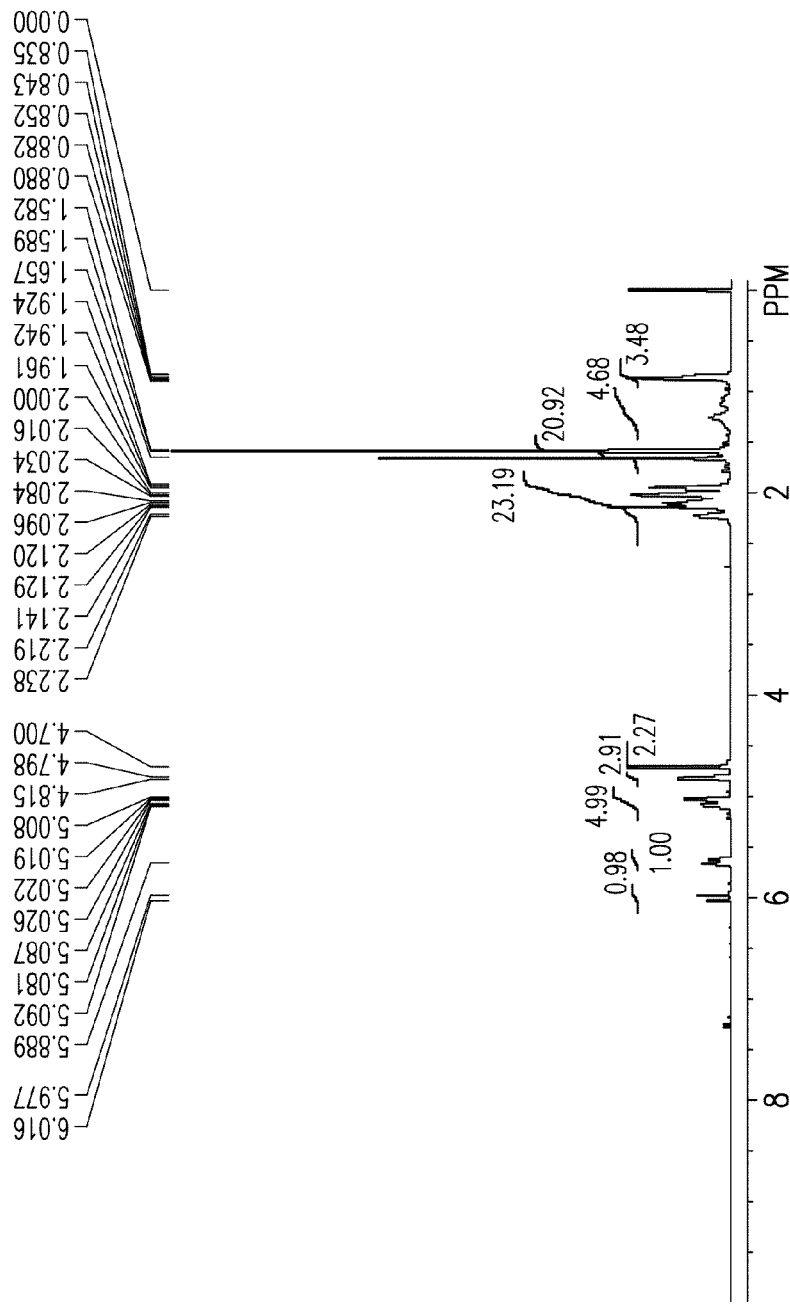
FIG. 6B provides a proton NMR spectrum of crude linear dimer (isosqualene and isomers) in carbon tetrachloride.

FIG. 6B provides an NMR spectrum for crude isosqualene in carbon tetrachloride. A tabulation of the NMR spectral data is provided below in Table 18B:

TABLE 18B

| Isosqualene prepared by a method herein | | Dimer reported by Akutagawa et al. | |
|---|---|---|---|
| Signal | Assignment | Signal | Assignment |
| 6.00 ppm, doublet, J = 15.8 Hz, 1H | H1 | No peak reported | — |
| 5.64 ppm, doublet of triplets, J = 15.8 Hz, 6.7 Hz, 1H | H2 | 5.52 ppm, multiplet | H2 |
| 5.03 ppm, multiplet, 4H | H3 | 5.15 ppm, triplet | H3 |
| 4.81 ppm, doublet, J = 6.5 Hz, 2H | H4 or H5 | No peak reported | H4 or H5 |
| 1.8-2.3 ppm, multiplets, 20H | 10 allylic CH2 groups | 2.18 ppm, multiplet | 10 allylic $CH_2$ groups |
| 1.66 ppm, broad singlet, 6H | 2 of the CH3 groups | No peak reported | — |
| 1.58 ppm, broad singlet, 6H | 4 of the CH3 groups | No peak reported | — |
| No signal | — | 1.50 ppm, multiplet | $CH_2$ |
| No signal | — | 1.18 ppm, singlet 6 CH3 groups | $CH_3$—C= |

As seen from the comparison in Table 18A, the signals at 6.00 ppm and 4.81 ppm for H1 and H4/H5, respectively, are missing in the spectral data provided by Akutagawa et al. Additionally, Akutagawa et al. report methyl singlets only at 1.18 ppm which is not consistent with the structure of isosqualene. The NMR spectral data presented in Akutagawa et al. is not consistent with isosqualene described herein.

Example 16

Large Scale Conversion of Farnesene to Squalane

Figure 7:
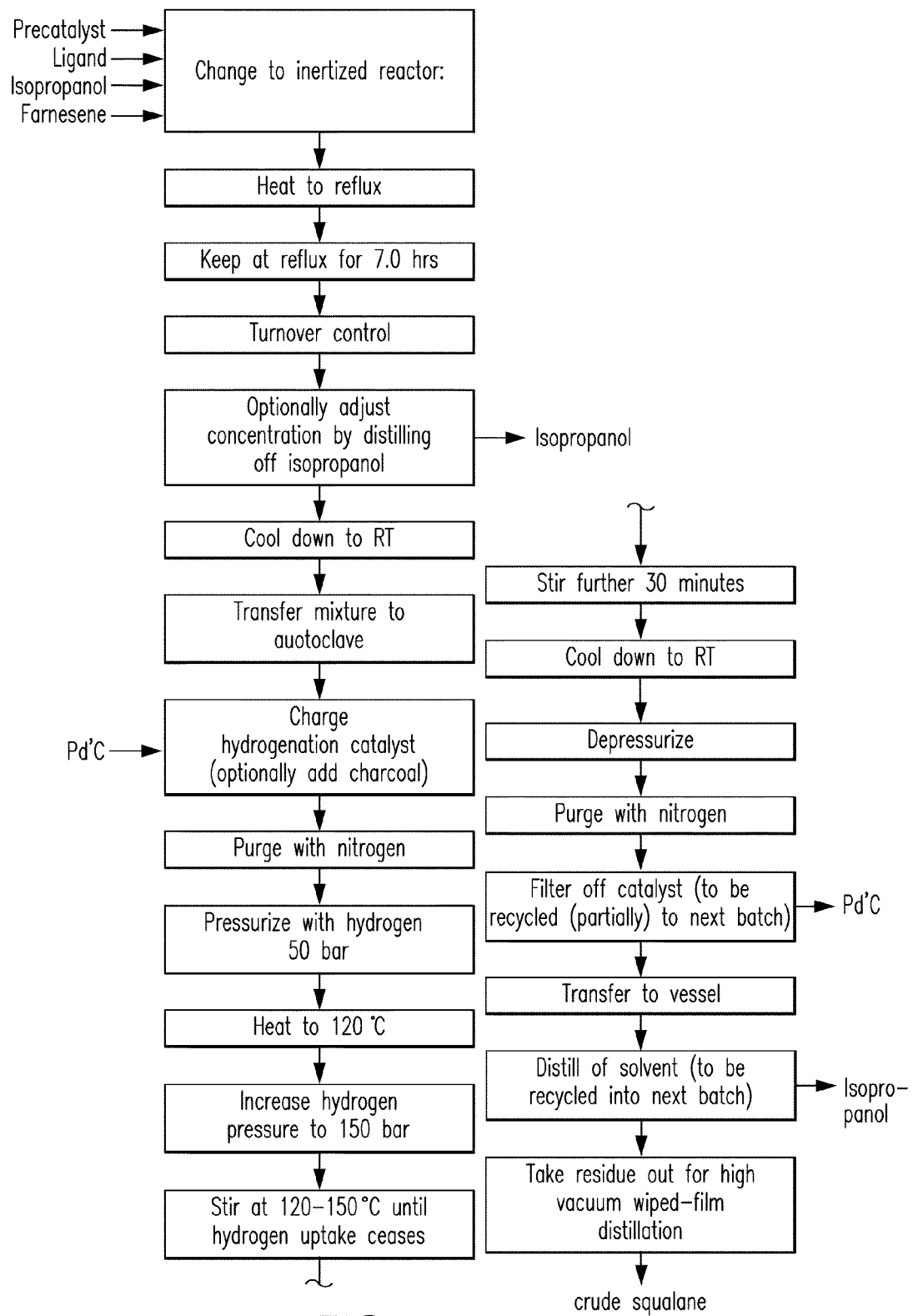
FIG. 7 provides a process flow diagram for a kilo lab sample preparation of squalane from farnesene.
Figure 8:
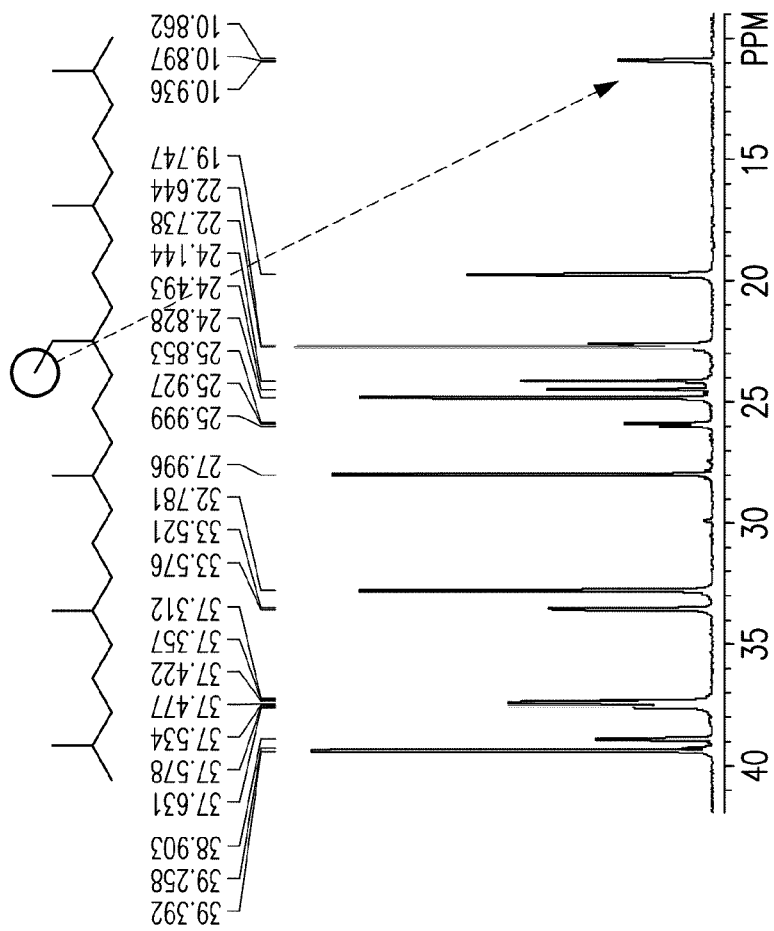
FIG. 8 provides a $^{13}$C NMR spectrum for Example 22.
Figure 9A:
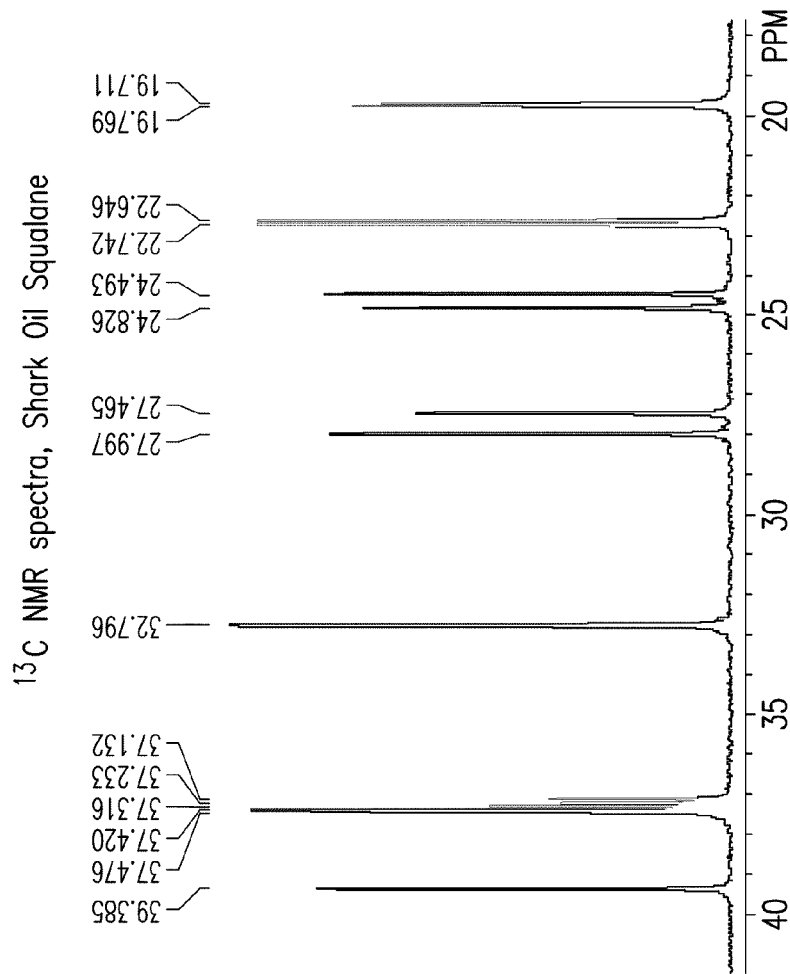
FIG. 9A provides a $^{13}$C NMR spectrum for Comparative Example 2, shark oil squalane.
Figure 9B:
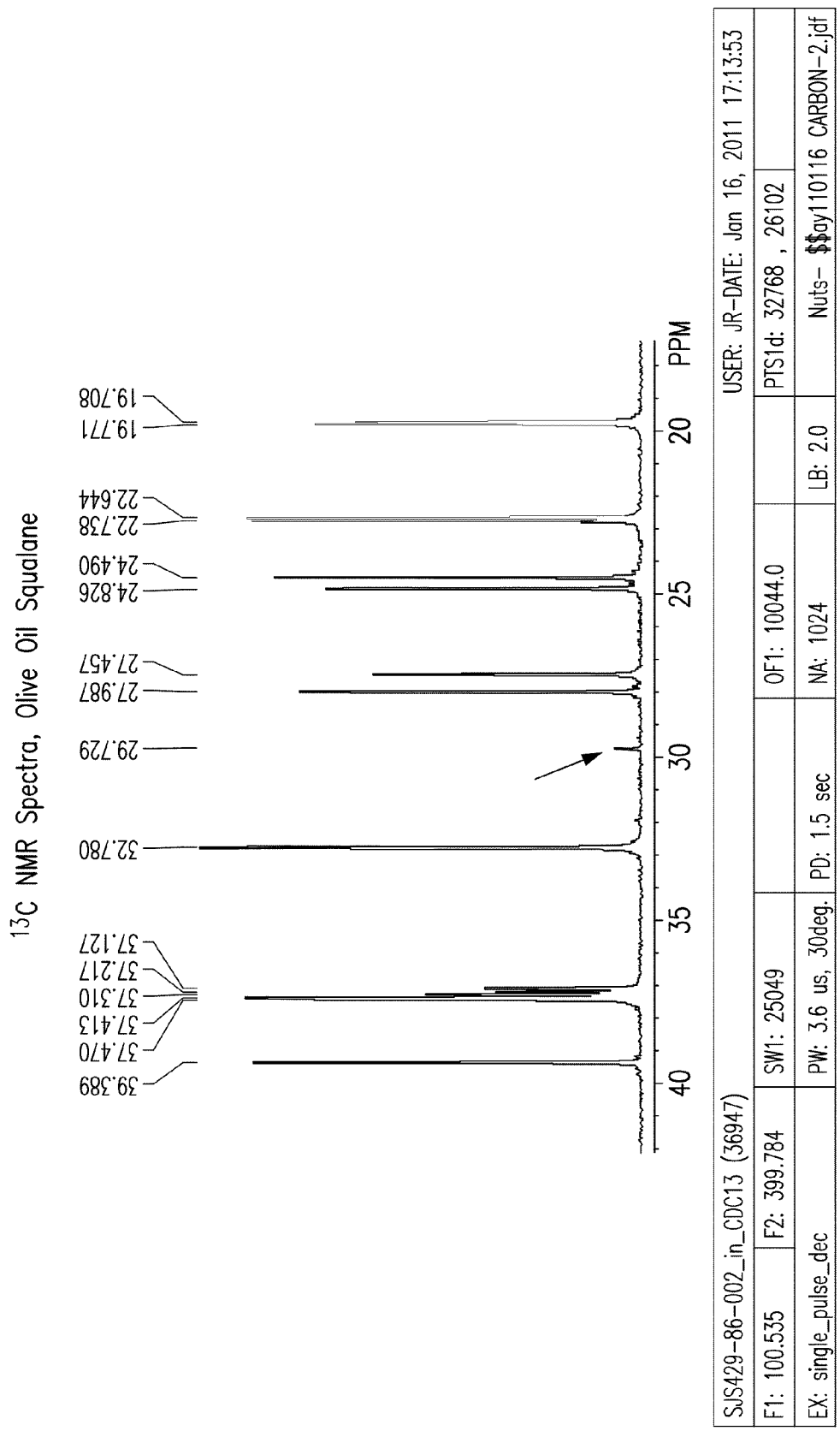
FIG. 9B provides a $^{13}$C NMR spectrum for Comparative Example 3, olive oil squalane.

A kilo lab sample was prepared using a 30 L glass reactor for dimerization and a 3 L autoclave for hydrogenation. Dimerization was done in three batches using 5 kg of farnesene each. FIG. 7 provides a process flow diagram for a kilo lab sample preparation of crude squalane from farnesene.

a) Dimerization

A dry 30 L glass reactor equipped with stirrer, nitrogen inlet, reflux condenser and distillation head was thoroughly inerted with nitrogen and charged with 5000 g of farnesene (98% purity, 5804 ml, 23.968 mol) and 14351 g of 2-propanol (18280 ml) (in some variations, a dosage-controlled reaction is desired, and the farnesene is not added before heating to reflux but gradually added to the boiling catalyst solution over 5 hours instead). 44.38 g of triphenylphosphine (169.2 mmol, 0.706 mol %) and 18.25 g of palladium(II) acetylacetonate (59.9 mmol, 0.250 mol %) were added sequentially to the stirred solution. The mixture is heated to mild reflux (85.8° C.) and kept at reflux for 7 hours. In some circumstances, a Pd mirror forms gradually on the reactor walls while the reaction mixture turns dark. After 7 hours, a sample analyzed by GC showed 85.4% isosqualene and 8% of unreacted farnesene. The yield determined by GC a/a was 87-89% based on farnesene, with 5-10% unreacted farnesene left. The reaction mixture was passed to the hydrogenation step without work-up.

b) Hydrogenation

To 400 g of the dimerization reaction mixture was added 2.662 g of hydrogenation catalyst (5% Pd on charcoal, dry powder, 0.1 mol % loading). This mixture was fed into a steel autoclave (0.7 L, 1.4571/316Ti), purged with nitrogen, pressurized with 50 bar hydrogen and heated up to 120° C. The hydrogen pressure was increased to 150 bar while the temperature rises to 160° C. (maximum). When hydrogen uptake has ceased, the reactor was cooled down, depressurized and purged with nitrogen. The catalyst was filtered off and the solvent removed in vacuum. Crude hydrogenation yield was almost quantitative.

The crude product was purified by wiped-film distillation (two stages) as described below.

c) Distillation

The distillation was done in a short-path distillation apparatus consisting of two evaporators and condensers in two passes. At first the low-boiling components were removed at a pressure of 1 mbar and a condenser temperature of 110° C. (only the first evaporator/condenser was used, the condenser was cooled with tap water, the vapor temperature was 43° C., residue was kept at 100° C., throughput was 1149 g/h). In the second pass the residue of the first pass was taken overhead at a pressure of 0.042 mbar in the first stage and 0.005 mbar in the second stage. The evaporator temperature was kept at 150° C. (both evaporators, vapor temperature was 73° C., residue was kept at 140° C., throughput was 428 g/h). The distillate had a purity of about 92-93% a/a squalane and did not contain detectable amounts of impurities derived from triphenylphosphine.

d) Reactor Cleaning Procedure

Removal of the palladium mirror in the dimerization reactor was done either by treatment with dilute hydrogen peroxide in hydrochloric acid as described earlier or by treatment with dilute nitric acid. First the reactor was decocted with water containing 1.8% commercial surfactant cleaner, then with 2.5% nitric acid and then with 1.75% caustic soda solution. Finally the reactor was rinsed with deionized water and then acetone to facilitate drying.

e) Palladium Recovery

Since palladium is the major cost driver in the total production costs of squalane, various recovery techniques were tried. The following organic adsorbents were screened for their efficacy to adsorb the residual dissolved Pd (the extent of Pd adsorption was determined by ICP (Inductively Coupled Plasma Spectrometry) analysis of the liquid phase before and after treatment):

Silica gel (large pore, 58 micron, 5% loading) lead to medium to long filtration times and removed about 83% of the residual dissolved Pd.

Cellulose (Arbocel B00-V, 1% loading) showed good filtration properties (much faster than silica gel), but removed only about 27% of the residual dissolved Pd.

Charcoal type Norit CA1 (powder, 0.5% loading) removed about 79% of the dissolved Pd and showed extremely fast filtration.

Charcoal type Norit RO0.8 (granules, 0.5% loading) removed only about 35% of the Pd, and destruction of the granules during stirring led to filter blockage, i.e. prohibitively high filtration times.

Charcoal type Norit SX (powder, 0.5% loading) removed about 40% of the dissolved Pd with medium to long filtration times (slightly faster than silica gel).

Combination of reductive treatment (using sodium borohydride) with charcoal did not significantly improve Pd precipitation.

Based on the observation that the triphenylphosphine and triphenylphosphine oxide from the dimerization step seem to be completely destroyed during hydrogenation, i.e. obviously do not require removal by precipitation from hexanes and filtration, the residual dissolved palladium may be deposited on charcoal during hydrogenation, rendering palladium on charcoal the hydrogenation catalyst of choice since this type of catalyst may be reworked after production.

The residual palladium content of the dimerization mixture dropped to the detection limit of 1 ppm after hydrogenation using palladium on charcoal as the catalyst, indicating complete deposition.

Example 17a

Dimerization of Farnesene with Palladium Carbene Followed by Hydrogenation

Palladium acetylacetonate (6.1 mg, $2\times10^{-5}$ mol, 0.02 mol % based on farnesene, 5000:1 substrate to catalyst ratio) and 1,3-bis(2,6-diisopropylphenyl)-4,5-dihydroimidazolium tetrafluoroborate (95.6 mg, $2\times10^{-4}$ mol) were added to a dry 100 ml round bottom flask with a stir bar. Fifteen ml of 5% sodium isopropoxide in anhydrous isopropanol and 25.3 ml (20.4 g, 0.10 mol) of farnesene were then added under nitrogen at room temperature. The septum was replaced with an oven-dried reflux condenser and the reaction mixture was stirred under nitrogen at 90° C. for 24 hours.

The reaction was cooled to room temperature and 75 ml of 5% ethyl acetate in hexanes was added. The round bottom flask was rinsed twice with 25 ml of 5% ethyl acetate in hexanes. The combined volumes were filtered through a silica pad (10 g), and the silica pad was washed with another 375 ml of 5% ethyl acetate in hexanes. The combined organic layers were concentrated by rotary evaporation to give 20.1 g of a light yellow oil.

A mixture of farnesene dimers (10.1 g) was placed in a 1 L Parr hydrogenation vessel containing 300 ml of reagent grade heptane and 0.2 g of 5% Pd on carbon. The mixture was placed under vacuum for half an hour. The mixture was then hydrogenated at 1000 psi at 80° C. for 16 hours. The reactor was allowed to cool to 30° C. and the contents were filtered through Celite to remove the catalyst. Removal of the solvent under reduced pressure afforded 10.1 g of clear liquid. A two step distillation via Kugelrohr afforded a trace amount of C-15 material (160° C., 0.01 torr), 6.4 g of C-30 dimers (235° C., 0.08 torr), and 3.4 g of trimer and tetramer as non-distilled residue. Both the dimer fraction and the trimer/tetramer fractions were clear liquids, with the latter fraction being somewhat more viscous but free-flowing. The distilled yield of the dimer fraction over two steps (dimerization and hydrogenation) was 62%.

The main dimer products (after hydrogenation) had the same retention time (GC-FID co-injection) and fragmentation patterns (GC/MS) as those observed for the squalane and isosqualane synthesized in previous examples. The ratio of squalane to isosqualane in this experiment was 9:1 (by GC-FID).

Example 17b

Dimerization of Farnesene with Palladium Carbene Followed by Hydrogenation

Palladium acetylacetonate (122 mg, $4\times10^{-4}$ mol, 0.02 mol % based on farnesene, 5000:1 substrate to catalyst ratio) and 1,3-bis(2,6-diisopropylphenyl)-4,5-dihydroimidazolium tetrafluoroborate (606 mg, $1.27\times10^{-3}$ mol) were added to a dry 2 liter round bottom flask with a stir bar. 300 ml of 5% sodium isopropoxide in anhydrous isopropanol and 408 g (2 mol) of farnesene were then added under nitrogen at room temperature. The septum was replaced with an oven-dried reflux condenser and the reaction mixture was stirred under nitrogen at 90° C. for 6.5 hours.

The reaction was cooled to room temperature and silica filtration was performed as described in Example 17a. To the filtrate was added an equal volume of heptane and the resulting mixture was hydrogenated in two batches in a 1 liter Parr vessel with 2% by weight of 5% Pd on carbon at 1000 psi for 16 hours at 85° C. After filtration through Celite a two step distillation via Kugelrohr afforded 6.3 grams of C-15 material (160° C., 0.01 torr), 376 g of C-30 dimers (235° C., 0.08 torr), and 22 g of trimer and tetramer as non-distilled. The distilled yield of the dimer fraction over two steps (dimerization and hydrogenation) was 89%.

The main dimer products (after hydrogenation) had the same retention time (GC-FID co-injection) and fragmentation patterns (GC/MS) as those observed for the squalane and isosqualane synthesized in previous examples. The ratio of squalane to isosqualane in this experiment was 6.3:1 (by GC-FID). As shown by comparison with Example 17a, shorter reaction time results in higher overall dimer yield, lower squalane:isosqualane ratio and reduced formation of trimer-tetramer.

Example 17c

Dimerization of Farnesene with Palladium Carbene Followed by Hydrogenation

Palladium acetylacetonate (3.0 mg, $1\times10^{-5}$ mol, 0.01 mol % based on farnesene, 10000:1 substrate to catalyst ratio) and 1,3-bis(2,6-diisopropylphenyl)imidazolium chloride (4.2 mg, $1\times10^{-5}$ mol) were added to a dry 100 ml round bottom flask with a stir bar. Fifteen ml of 5% sodium isopropoxide in anhydrous isopropanol and 25.3 ml (20.4 g, 0.10 mol) of farnesene were then added under nitrogen at room temperature. The septum was replaced with an oven-dried reflux condenser and the reaction mixture was stirred under nitrogen at 85° C. for 16 hours. GC/MS showed 2.5% residual farnesene.

The reaction was cooled to room temperature and 75 ml of 5% ethyl acetate in hexanes was added. The mixture was filtered through a silica pad (10 g), and the silica pad was washed with another 120 ml of 5% ethyl acetate in hexanes.

The combined organic layers were concentrated by rotary evaporation to give 20.6 g of a light yellow oil.

A mixture of farnesene dimers (7.50 g) was placed in a 75 mL Parr hydrogenation vessel containing 30 ml of reagent grade heptane and 75 mg of 10% Pd on carbon. The mixture was then hydrogenated at 300 psi at 80° C. for 16 hours. The reactor was allowed to cool to 30° C. and the contents were filtered through Celite to remove the catalyst.

The main dimer products (after hydrogenation) had the same retention time (GC-FID co-injection) and fragmentation patterns (GC/MS) as those observed for the squalane and isosqualane synthesized in previous examples. The ratio of squalane to isosqualane in this Example was 5:1 (by GC-FID). The ratio of farnesane/dimer/trimer/tetramer was 2.9/90.1/7.0/0 respectively (by GPC).

Example 17d

Dimerization of Farnesene with Palladium Carbene Followed by Hydrogenation 1,3-Bis(2,6-diisopropylphenyl)imidazol-2-ylidene(1,4-naphthoquinone)palladium(0) dimer (13.0 mg, $1 \times 10^{-5}$ mol, 0.01 mol % based on farnesene, 10000:1 substrate to catalyst ratio) was added to a dry 100 ml round bottom flask with a stir bar. Fifteen ml of 5% sodium isopropoxide in anhydrous isopropanol and 25.3 ml (20.4 g, 0.10 mol) of farnesene were then added under nitrogen at room temperature. The septum was replaced with an oven-dried reflux condenser and the reaction mixture was stirred under nitrogen at 85° C. for 16 hours. GC/MS showed complete conversion of farnesene to dimers.

The reaction was cooled to room temperature and 75 ml of 5% ethyl acetate in hexanes was added. The mixture was filtered through a silica pad (10 g), and the silica pad was washed with another 120 ml of 5% ethyl acetate in hexanes. The combined organic layers were concentrated by rotary evaporation to give 19.9 g of a light yellow oil.

A mixture of farnesene dimers (7.50 g) was placed in a 75 mL Parr hydrogenation vessel containing 30 ml of reagent grade heptane and 75 mg of 10% Pd on carbon. The mixture was then hydrogenated at 300 psi at 80 deg° C. for 16 hours. The reactor was allowed to cool to 30 deg° C. and the contents were filtered through Celite to remove the catalyst.

The main dimer products (after hydrogenation) had the same retention time (GC-FID co-injection) and fragmentation patterns (GC/MS) as those observed for the squalane and isosqualane synthesized in previous examples. The ratio of squalane to isosqualane in this experiment was 5:1 (by GC-FID). The ratio of farnesane/dimer/trimer/tetramer was 0.8/90.8/2.7/5.8 respectively (by GPC).

Example 18

Not Used

Examples 19a-19y

Dimerization of β-Farnesene Using Zirconium or Titanium Catalysts

For each of Examples 19a-19y, Amyris β-farnesene was degassed on a high vacuum line, then filtered through activated alumina inside a glove box prior to use, and all reactions were carried out in a glove box.

Example 19a

Solid PPh3 (0.063 mg, 0.240 mmol) was weighed into a vial in a glove box. The $PPh_3$ was diluted with 2.406 mL dry toluene. $Zr(OtBu)_4$ (available from Strem Chemicals, Inc., Newburyport, Mass.) (84 mg, 0.219 mmol) was added via pipette. This mixture was cooled in the glove box freezer at −40° C. for 15 minutes. To this mixture was added 3.942 mL (3.942 mmol) of a 1.0 M solution of $Et_2AlCl$ (available from Sigma Aldrich, St. Louis, Mo.) in heptane. The mixture was allowed to warm for ~30 minutes. A 535 microL aliquot of this mixture (0.002 mol equivalents with respect to farnesene) was added to farnesene (4.972 g, 24.33 mmol; pre-cooled at −40° C.) while mixing. This mixture was heated to 100° C. and left to stir at that temperature for 24 hours. After 24 hours, the mixture was cooled, removed from the glovebox. Toluene was added, followed by dilute aqueous HCl. The mixture was dried with $K_2CO_3$ and filtered through a small plug of neutral alumina to remove any catalyst residue, and washed with excess toluene.

To this mixture was added 0.2 weight percent Pd/C hydrogenation catalyst. If necessary, the mixture was further diluted with heptane and transferred to a Parr bomb for hydrogenation. The mixture was hydrogenated overnight in a batch reactor with pressure around 1000 psi. After hydrogenation, the mixture was filtered through a plug of neutral alumina.

The crude product was distilled under vacuum in a 2-stage distillation. The first stage at 165° C. 1 Torr vacuum removed the light molecular weight fraction (farnesane and other hydrocarbons having 15 carbons or less) and the second stage at 215-265° C. 1 torr vacuum to isolate the dimer fraction (C30 compounds) from the heavier materials (trimer and tetramer). Dimer yield was measured by GPC. The relative amounts of squalane, isosqualane and neosqualane were determined by GC-MS after hydrogenation. Results are shown as Entry 1, Table 19.

Example 19b

Solid PPh3 (0.065 mg, 0.248 mmol) was weighed into a vial in the glove box. This was diluted with 2.388 mL dry toluene. $Zr(OtBu)_4$ (88 uL, 0.225 mmol) was added via pipette, to make a 0.091M solution in $Zr(OtBu)_4$. This mixture was cooled in the glove box freezer at −40° C. for 15 minutes. Farnesene (5.721 g, 28.03 mmol) was weighed into a 20 mL vial and cooled to −40° C. Farnesene was removed from the freezer. To this was added 0.929 mL (0.929 mmol) of a 1.0 M solution of $Et_2AlCl$ in heptane. To this mixture was added a 567 μL aliquot of the $Zr(OtBu)_4/PPh3$ solution. The 20 mL vial was then heated to 90° C. and left to stir at that temperature for 18 hours. After 18 hours, the mixture was cooled, removed from the glovebox. Toluene was added, followed by dilute aqueous HCl. The mixture was dried with $K_2CO_3$ and filtered through a small plug of neutral alumina to remove any catalyst residue, and washed with excess toluene. The reaction product was hydrogenated and distilled as in Example 19a. Results were similar to those in Example 19a.

Example 19c

β-Farnesene (5.259 g, 25.7 mmol) was weighed into a vial in a glove box. To this was added 1.542 mL (1.542 mmol) of a 1.0 M $Et_2AlCl$ solution in heptanes. To this mixture, solid $ZrCl_4$ (available from Strem Chemicals) (30 mg, 0.129 mmol) was added. This mixture was heated to 120° C. After 24 hours, all of the farnesene was consumed. The mixture was cooled and removed from the glovebox. Toluene was added, followed by dilute aqueous HCl. The mixture was dried with $K_2CO_3$ and filtered through a small plug of neutral alumina to remove any catalyst residue, and washed with excess toluene.

The reaction product was hydrogenated and distilled as in Example 19a. Results are shown as Entry 3, Table 19.

Examples 19d-19i

Different catalyst systems were tested in Examples 19d-19i. The reactions were carried out as in Example 19a, using the molar ratio of amount of zirconium catalyst:ligand:alkyl aluminum co-catalyst as 1:1.1:18. The molar ratio of zirconium catalyst:β-farnesene was 0.002:1. For example 19i, the molar ratio of titanium catalyst:alkyl aluminum co-catalyst was 0.8:1, and the molar ratio of β-farnesene:titanium catalyst was 500:1. The time of the reaction and the catalyst were varied as shown in Entries 4-9 in Table 19.

Examples 19i-19q

Different ligands were tested in Examples 19i-19q. The reactions were carried out as in Example 19a, using the molar ratio of amount of zirconium catalyst:ligand:alkyl aluminum co-catalyst as 1:1.1:18. The molar ratio of zirconium catalyst:farnesene was 0.002:1. The time of the reaction and the catalyst were varied as shown in Entries 10-17 in Table 19

Examples 19r-19y

Catalyst systems using $ZrCl_4$ were tested in Examples 19r-19y. The reactions were carried out as in Example 19b, using a molar ratio of zirconium catalyst:alkyl aluminum co-catalyst as 1:12, except for Example 19x (Entry 24), where the zirconium catalyst:alkyl aluminum co-catalyst was 1:18, and Example 19y (Entry 25), where the zirconium catalyst:alkyl aluminum co-catalyst was 1:6. The time of the reaction and the catalyst system were varied as shown in Entries 18-25 in Table 19.

TABLE 19

| Example | Entry | Catalyst system | T (°C.) | Reaction time (hours) | Conv. (%) | Dimer yield (%) | Dimer:(trimer + tetramer): higher oligomers | squalane: isosqualane: neosqualane: others* | Isosqualane: Squalane |
|---|---|---|---|---|---|---|---|---|---|
| 19a | 1 | $Zr(OtBu)_4$/PPh3/$Et_2AlCl$ | 100 | 24 | 100 | 57 | 57:42:1 | 1.5:91:6:1.5 | 60:1 |
| 19b | 2 | $Zr(OtBu)_4$/PPh3/$Et_2AlCl$ | 100 | 24 | 100 | 44 | NM | NM | NM |
| 19c | 3 | $ZrCl_4$/$Et_2AlCl$ | 120 | 24 | 100 | 44 | 44:56:0 | 4:82:10:3 | 20:1 |
| 19d | 4 | $Zr(OtBu)_4$/PPh3/Et3Al | 100 | days | 0 | — | — | — | |
| 19e | 5 | $Zr(OtBu)_4$/PPh3/$Oct_3Al$ | 100 | days | 0 | — | — | — | |
| 19f | 6 | $Zr(OtBu)_4$/PPh3/$iBu_3Al$ | 100 | days | 0 | — | — | — | |
| 19g | 7 | $Zr(OtBu)_4$/$Et_2AlCl$ | 100 | days | 0 | — | — | — | |
| 19h | 8 | $Zr(OEt)_4$/PPh3/$Et_2AlCl$ | 100 | 17 | 100 | 34 | 34:66:0 | — | |
| 19i | 9 | $TiCl_4$/$Oct_3Al$ | 100 | 24 | 100 | 31 | 31:60:9 | — | |
| 19j | 10 | $Zr(OtBu)_4$/P(o-OMePh)3/$Et_2AlCl$ | 100 | 3.75 | 100 | NM** | NM | 3:86:10:0 | 29:1 |
| 19k | 11 | $Zr(OtBu)_4$/$Ph_2PtBu$/$Et_2AlCl$ | 100 | 3.75 | 100 | NM | NM | 3:86:10:0 | 29:1 |
| 19l | 12 | $Zr(OtBu)_4$/P(m-OMePh)3/$Et_2AlCl$ | 100 | 3.75 | 100 | NM | NM | 3:86:10:0 | 29:1 |
| 19m | 13 | $Zr(OtBu)_4$/Bipy/$Et_2AlCl$ | 100 | 3.75 | 100 | NM | NM | 3:86:10:0 | 29:1 |
| 19n | 14 | $Zr(OtBu)_4$/DPPE/$Et_2AlCl$ | 100 | 3.75 | 100 | NM | NM | 3:86:10:0 | 29:1 |
| 19o | 15 | $Zr(OtBu)_4$/$PCy_3$/$Et_2AlCl$ | 100 | 3.75 | 100 | NM | NM | 3:86:10:0 | 29:1 |
| 19p | 16 | $Zr(OtBu)_4$/PPh3/$Et_2AlCl$ | 100 | 3.75 | 100 | NM | NM | 3:86:10:0 | 29:1 |
| 19q | 17 | $Zr(OtBu)_4$/$Et_2AlCl$ | 100 | 3.75 | 100 | NM | NM | 3:86:10:0 | 29:1 |
| 19r | 18 | $ZrCl_4$/MAO | 100 | 16 | 100 | 25 | 25:43:31 | 0:94:6:0 | — |
| 19s | 19 | $ZrCl_4$/$Oct_3Al$ | 100 | 16 | 100 | 37 | 37:63:0 | 9:76:15:0 | 8:1 |
| 19t | 20 | $ZrCl_4$/Et3Al | 100 | 16 | 100 | 37 | 37:63:0 | 11:73:16:0 | 7:1 |
| 19u | 21 | $ZrCl_4$/$Et_2Al$ | 100 | 16 | 100 | 8 | 8:92:0 | 0:100:0:0 | — |
| 19v | 22 | $ZrCl_4$/$Et_2Al(OEt)$ | 100 | 16 | 70 | 71 | 71:29:0 | 12:80:4:4 | 7:1 |
| 19w | 23 | $ZrCl_4$ | 100 | 16 | 100 | NM | 0:0:100 | NM | NM |

TABLE 19-continued

| Example | Entry | Catalyst system | T (° C.) | Reaction time (hours) | Conv. (%) | Dimer yield (%) | Dimer:(trimer + tetramer): higher oligomers | squalane: isosqualane: neosqualane: others* | Isosqualane: Squalane |
|---|---|---|---|---|---|---|---|---|---|
| 19x | 24 | ZrCl$_4$/Et$_2$AlCl | 100 | 16 | 100 | 8 | | 0:100:0 | — |
| 19y | 25 | ZrCl$_4$/Et$_2$AlCl | 100 | 16 | 100 | 9 | | 0:95:5:0 | — |

*For any squalane, isosqualane or neosqualane amounts indicated as "0" in Table 19, the amount is more accurately reflected as about 2% or less.
**NM means not measured.

Certain of the examples shown in Table 19 exhibited significant quantities of tetramers and trimers. For example, Example 19a exhibited trimers and tetramers that combined made up 42% of the reaction product, as determined by GPC. Example 19b exhibited trimers and tetramers that combined made up 46% of the reaction product. Example 19 h exhibited trimers and tetramers that combined made up 66% of the reaction product. Example 19i exhibited trimers and tetramers that combined made up 60% of the reaction product, and oligomers larger than tetramers that made up 9% of the reaction product. Example 19r exhibited trimers and tetramers that combined made up 43% of the reaction product, and 31% oligomers larger than tetramers. Examples 19s-19t showed 63% trimers and tetramers combined. Example 19u showed 92% trimers and tetramers combined. Example 19v showed 29% trimers and tetramers combined. Examples 19x and 19y exhibited 93% and 91% trimers and tetramers combined, respectively.

Figure 18A:
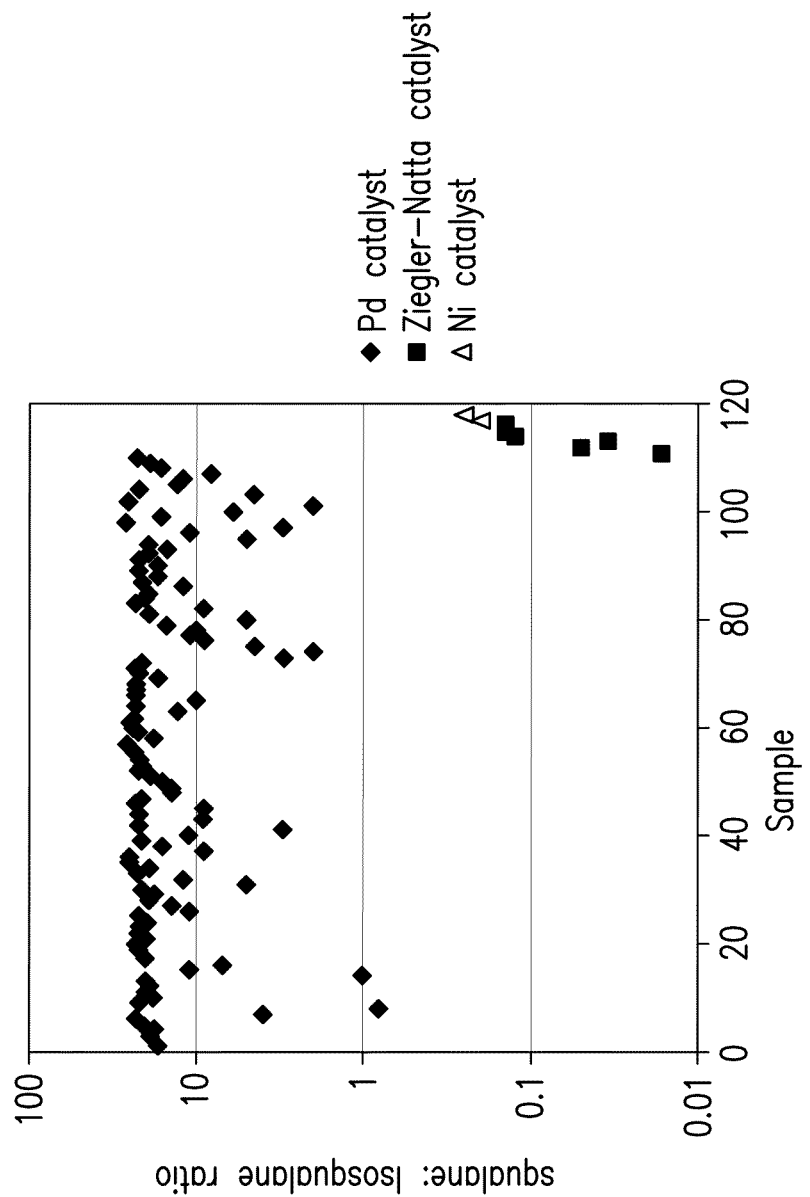
FIG. 18A provides a compilation of the squalane:isosqualane ratios obtained for compositions made in Examples 1-14 and Examples 19a-19y.
Figure 18B:
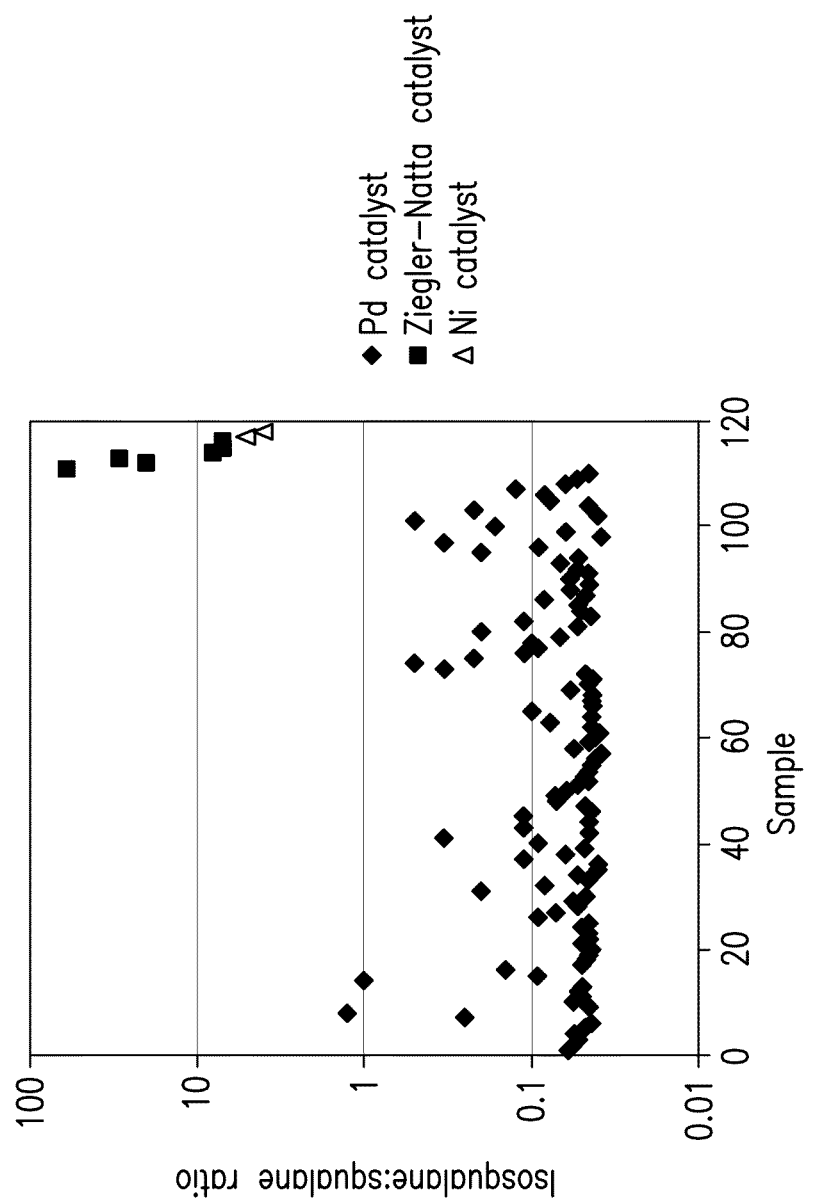
FIG. 18B provides a compilation of the isosqualane:squalane ratios obtained for compositions made in Examples 1-14 and Examples 19a-19y.

FIGS. 18A-18B provide graphical compilations of squalane:isosqualane ratios and isosqualane:squalane ratios obtained for Examples 1-14 and 19a-19y. As seen, for palladium catalyzed reactions (Examples 1-14), squalane:isosqualane ratios ranging from about 1 to 26 (and corresponding isosqualane:squalane ratios ranging from 0.04 to about 1) are obtained. For nickel catalyzed reactions, Example 14, squalane:isosqualane ratios from about 0.2-0.25 are obtained (and corresponding isosqualane:squalane ratios from about 4 to 5) are obtained. For Ziegler-Natta catalyzed reactions, Examples 19a-19y, squalane:isosqualane ratios from about 0.01 to about 0.15 (and corresponding isosqualane:squalane ratios from about 7 to 60) are obtained.

Examples 20-22 and Comparative Examples 2-3

Squalane Compositions Described Herein Compared to Squalane Derived from Shark Oil and Squalane Derived from Vegetable Oil Squalane derived from shark oil and squalane derived from olive oil are each compared by GC-MS analysis and by $^{13}$C NMR spectroscopy to a representative sample comprising squalane and isosqualane as described herein. Table 20 provides details regarding Examples 20-22 and Comparative Examples 1 and 2:

TABLE 20

| Example or Comparative Example # | Sample ID | Squalane % | Isosqualane % | Source |
|---|---|---|---|---|
| Example 20 | PPD110410 | 90 area %* | 4.2 area %* | Amyris |
| Example 21 | PPD063010 | 91.6 area %* | 5 area %* | Amyris |
| Example 22 | SJS-429-59-D2** | 1.5 area %* | 80 area %* | Amyris |

TABLE 20-continued

| Example or Comparative Example # | Sample ID | Squalane % | Isosqualane % | Source |
|---|---|---|---|---|
| Comparative Example 2 | SJS-429-86-001 Jedwards Lot 536 | 99.7% | 0 | Shark oil squalane, from Jedwards Int'l, Quincy MA |
| Comparative Example 3 | SJS-429-86-002 Jedwards Lot 1275 | 92% | 0 | Olive oil squalane, from Jedwards Int'l, Quincy MA |

*Area % in Table 20 were measured by GC-FID.
**Note that sample SJS-429-59-D2 was estimated to contain about 10% trimer. Sample SJS-429-59-D3 was obtained by taking a portion of SJS-429-D2 and subjecting it to a subsequent distillation at 265° C. and 1 torr vaccuum to remove more of the trimer component.

For Examples 20 and 21, the following typical experimental procedure was used. 18 L of 2-propanol was added to the stirred 30 L jacketed vessel followed by 6.25 kg β-farnesene, 36.2 g triphenylphosphine and 25 g Palladium (II) acetylacetonate. The mixture was then heated at 80° C. for 19 hours. GCMS shows a ratio of 92:8 linear dimer to farnesene after 8 hr. The reaction was cooled to room temperature and then drained from the reactor and then filtered through Norit CA-1 activated carbon which was washed with an additional 4 L isopropanol. The combined isopropanol filtrates were filtered through paper and then concentrated in vacuo to give the crude dimer as a yellow oil. Hydrogenation was carried out in a batch mode in a 1 L reactor, with typical conditions as follows: To each liter of dimer was added 400 g activated HTC Ni 500 RP 1.2 catalyst (available from Johnson Matthey, Pasadena, Tex.). The reactor was pressurized to 500 psig, and the reaction was carried out at 100° C.-160° C. until hydrogen uptake had ceased. The catalyst was removed by filtration through a silica or alumina column, and solvent was removed by evaporation. The isolated hydrocarbon was then distilled using a wiped film distillation apparatus as follows: The hydrocarbon was put under vacuum at 25 Torr at about 160° C.-173° C. to remove farnesane and other low molecular weight species in a first pass. Subsequently, the hydrocarbon was put under vacuum at 1 torr at 230° C. to distill off the desired product in a second pass.

Samples of squalane are evaluated by carbon-NMR ($^{13}$C-NMR) spectroscopy to establish characteristics of carbon-carbon bonds within the molecular structure. The number of hydrogen atoms and carbon atoms that are bound to an individual carbon atom affects electron density and length of the bond. Isosqualane has a methyl (—CH$_3$) group bonded to an ethyl carbon (—CH2—), which gives rise to unique spectra for isosqualane, which is not observed in commercial squalane products.

Samples of squalane are evaluated for characteristic boiling points under controlled conditions of vaporization, by using gas chromatography with flame ionization detection (GC-FID). This technique is able to separate squalane and isosqualane from hydrocarbons of similar molecular weight, and provides a quantitative measure of purity based on changes in electrical current measured during combustion of the hydrocarbons.

Samples of squalane are further evaluated for characteristic molecular ion fragments by first separating squalane and isosqualane by gas chromatography and then subjecting the compounds to high voltage electrons in a quadrupole mass spectrophotometer (GC-MS). Squalane and isosqualane both have the empirical formula $C_{30}H_{62}$, molecular weight 422 atomic mass units (amu). Isosqualane has a characteristic loss of ethyl (—$C_2H_5$, mw 29 amu), which yields an ion fragment with 393 m/z (mass/charge). The fragmentation patterns are matched against the National Institute of Standards and Technology (NIST) mass spectral reference library.

The chemical structure for squalane ($C_{30}H_{62}$, molecular weight 422 amu), is:

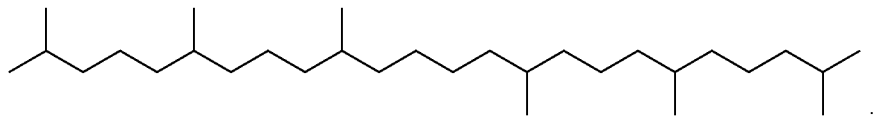 [SMILES: CC(C)CCCC(C)CCCC(C)CCCCC(C)CCCC(C)CCCC(C)C]

The chemical structure for isosqualane ($C_{30}H_{62}$, molecular weight 422 amu) is:

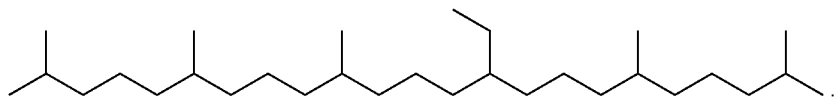 [SMILES: CCC(CCCC(C)CCCC(C)C)CCCC(C)CCCC(C)CCCC(C)C]

Materials and Methods

Amyris Squalane, Lot PPD063010, purity 91% (w/w) squalane (Example 21); Amyris Squalane, Lot PPD110410, purity 85% (w/w) squalane (Example 20); Amyris Isosqualane SJS-429-59-D2 (Example 22), technical, approximate purity 80% isosqualane (purity is area % by GC-FID); Squalane, derived from Shark Liver Oil, JEdwards International, Lot 536, manufacturer's purity 99.7% (Comparative Example 2); Squalane, derived from Olive Oil, JEdwards International, Lot 1275, manufacturer's purity 92% (Comparative Example 3).

Gas Chromatograph, Agilent 6890, equipped with Agilent 5973 Mass Spectrometry Detector (GC-MS). The analytical column is Agilent P/N 19091Z-005, HP-1, 50 m×0.20 mm, 0.10 film, 100% dimethyl-polysiloxane stationary phase.

Gas Chromatograph, Agilent 7890, equipped with Flame Ionization Detector (GC-FID). The analytical column is identical to that used for GC-MS analysis, Agilent P/N 19091Z-005, HP-1, 50 m×0.20 mm, 0.10 film, 100% dimethylpolysiloxane stationary phase. GC-FID can be used to determine purity as a wt % as follows: A known quantity of tetradecane is used as an internal standard for calibration of GC-FID response. The sample for which purity is to be determined is diluted in hexane and an aliquot is analyzed by GC-FID. Quantitation is based on peak area of squalane, identified by matching the GC retention time for a known analytical reference standard of squalane having a purity of 99% or higher, e.g., a known squalane standard having a purity of 99.7% from Jedwards, International, as described below.

For mass spectrometry analysis, an aliquot of squalane is diluted to 0.2% (v/v) in hexane and injected (50:1 split ratio) into the gas chromatography system. Isosqualane and squalane are separated based on approximate boiling point and small structural differences using an oven ramp from 150° C. to 270° C.; the heating rate is controlled at 25° C./minute to 250° C., then slowed to 2° C./min to 270° C. The analytes are identified by their retention time and mass spectra. The system is equipped with a library of spectra that allows matching of the mass spectra of analytes with authenticated spectra in the NIST library based on a peak and pattern matching algorithm that assigns a match ranking ranging from 100 (perfect match) to 0 (no match). Analytes that exhibit co-incident retention times, and have spectral match quality values above 90, have very high probability of being identical. Small differences between close numbers are considered insignificant. Amyris squalane typically exhibits a match quality of >94 when compared with NIST mass spectra for squalane (Library Revision 08). For $^{13}$C-NMR analysis, an aliquot of the compound (squalane or isosqualane) is dissolved in CDCl$_3$ at approximately 5-10 mg/mL. The sample is analyzed in the NMR spectrometer for 400-4000 scans. Peaks are assigned based on comparison of chemical shifts to carbons in analogous chemical environments.

For quantitative purity analysis (e.g., wt %), an aliquot of approximately 100 milligrams of squalane is weighed and diluted with hexane. A known quantity of tetradecane is added as an internal standard for calibration of GC-FID response. The mixture is further diluted in hexane to a final concentration of approximately 0.02% (w/v) squalane, and an aliquot is injected (50:1 split ratio) into the gas chromatography system. Squalane is separated from other hydrocarbons based on boiling point using an oven ramp from 60° C. to 320° C. Quantitation is based on peak area of squalane, identified by matching the GC retention time for a known analytical reference standard of squalane.

Analytical Results

Figure 10:
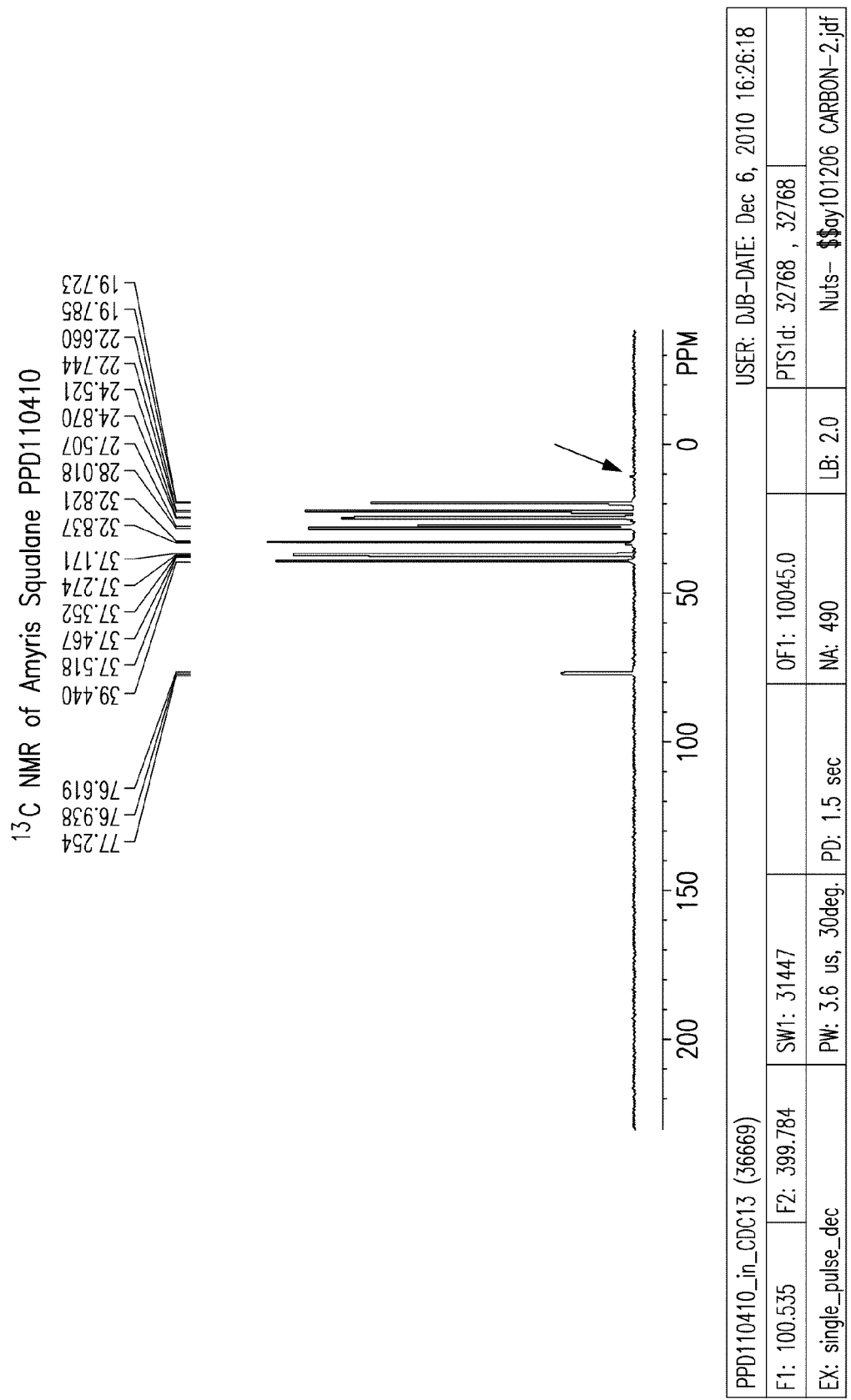
FIG. 10 provides a $^{13}$C NMR spectrum for Example 20, Amyris Squalane lot PPD110410.

The $^{13}$C-NMR spectrum for commercially available squalane derived from shark oil (sample SJS429-86-001) is shown in FIGS. 9A and 11A-11F. The $^{13}$C-NMR spectrum for commercially available squalane derived from olive oil (sample SJS429-86-002) is shown in FIG. 9B and FIGS. 11A-11F. The 13C-NMR spectrum for Amyris squalane, lot PPD110410 is shown in FIG. 10 and in FIGS. 11A-11F. The $^{13}$C-NMR spectrum for Amyris squalane, Lot PPD063010, is shown in Figure FIGS. 11A-11F. In order to identify spectral peaks that are unique to the isosqualane isomer, an analytical standard of isosqualane was synthesized, purified, and confirmed by GC-MS to have a mass spectral pattern consistent with $C_{30}H_{62}$, molecular weight 422 amu. The $^{13}$C-NMR spectra for this isosqualane analytical standard SJS-429-59-D3 is shown in FIG. 8 and FIGS. 11A-11F.

Figure 11A:
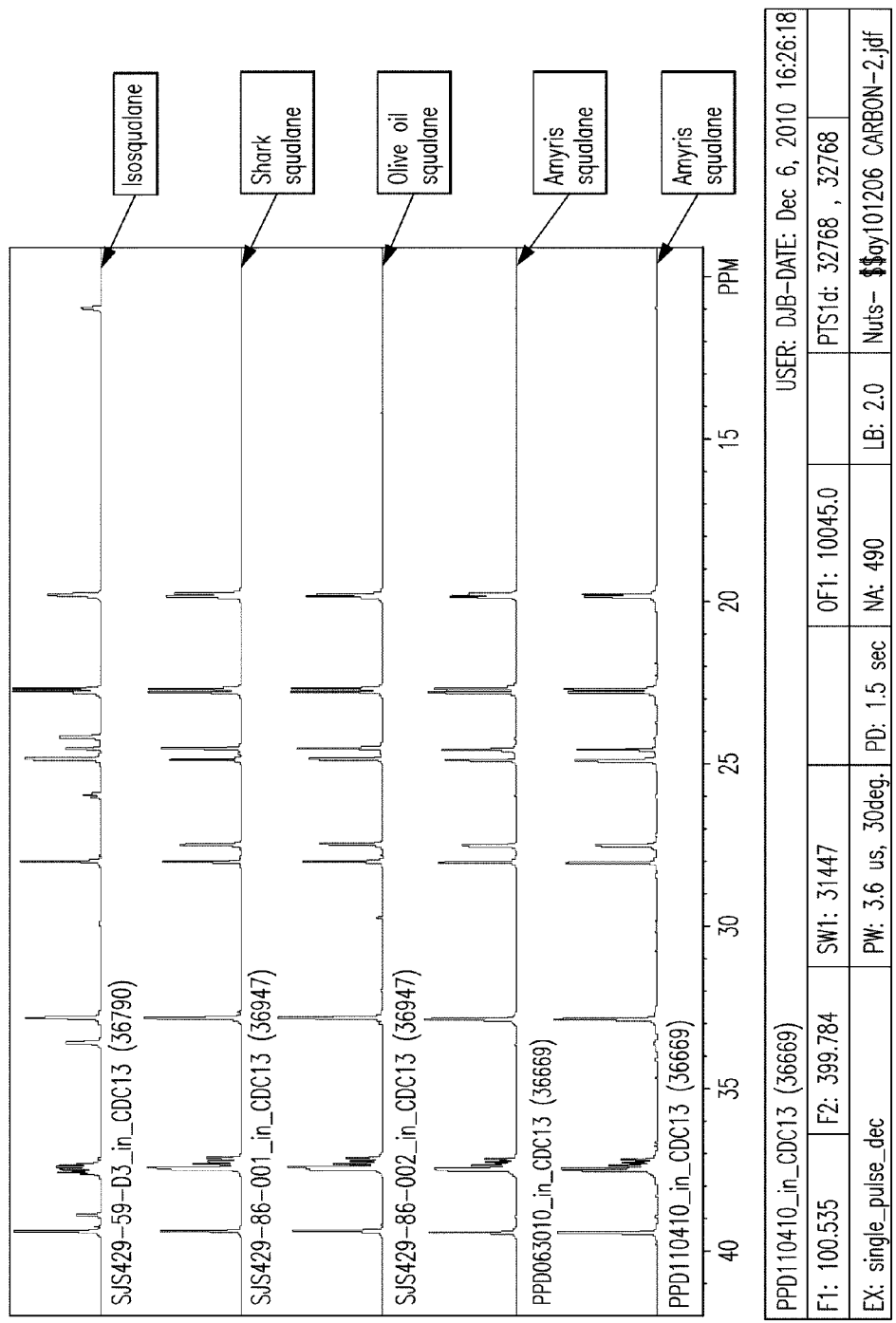
FIGS. 11A-11B provide an overlay of $^{13}$C NMR spectra for Examples 20-22, and Comparative Examples 2 and 3 over the region 9 ppm to 42 ppm.
Figure 11B:
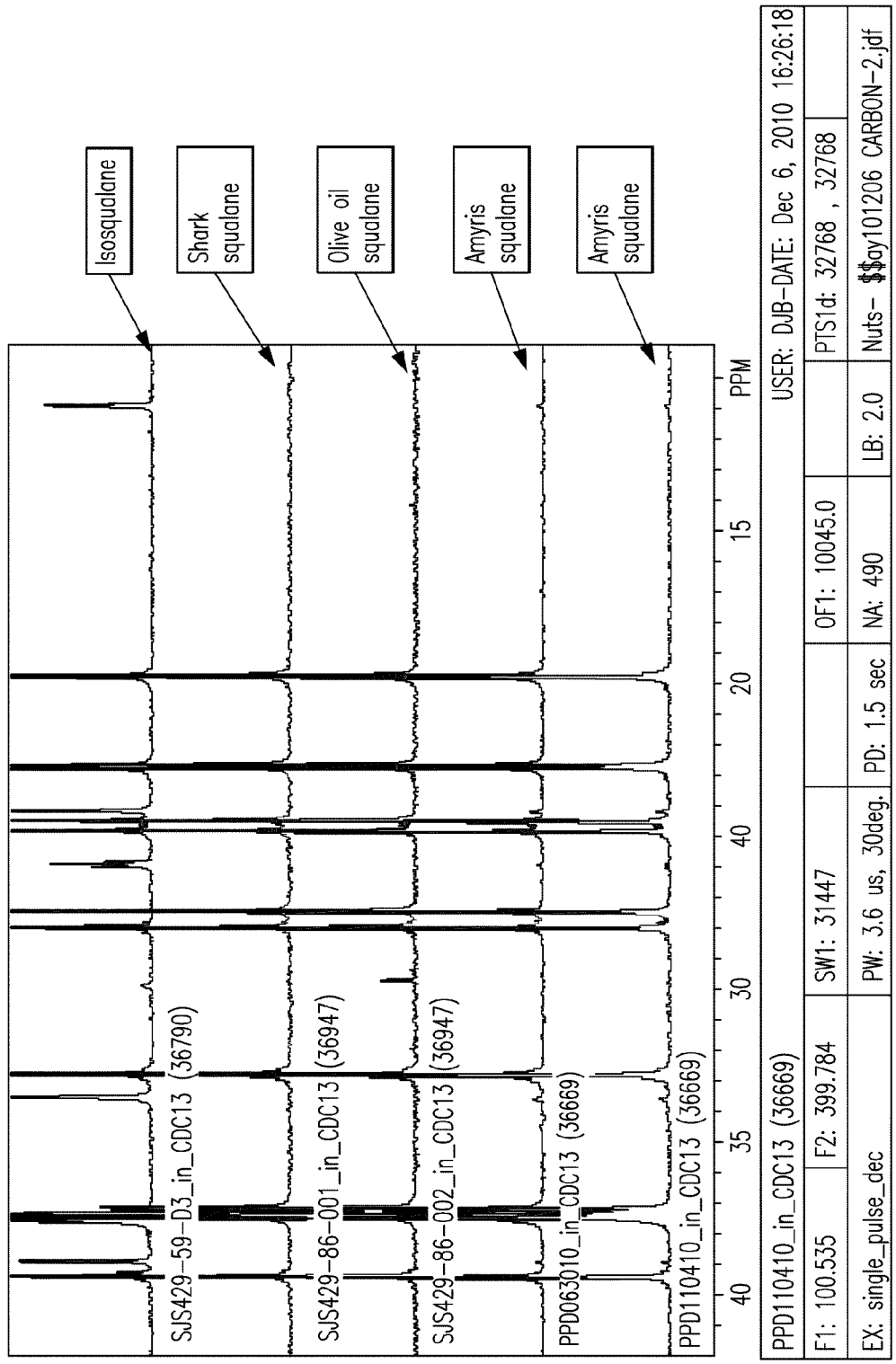
Figure 11C:
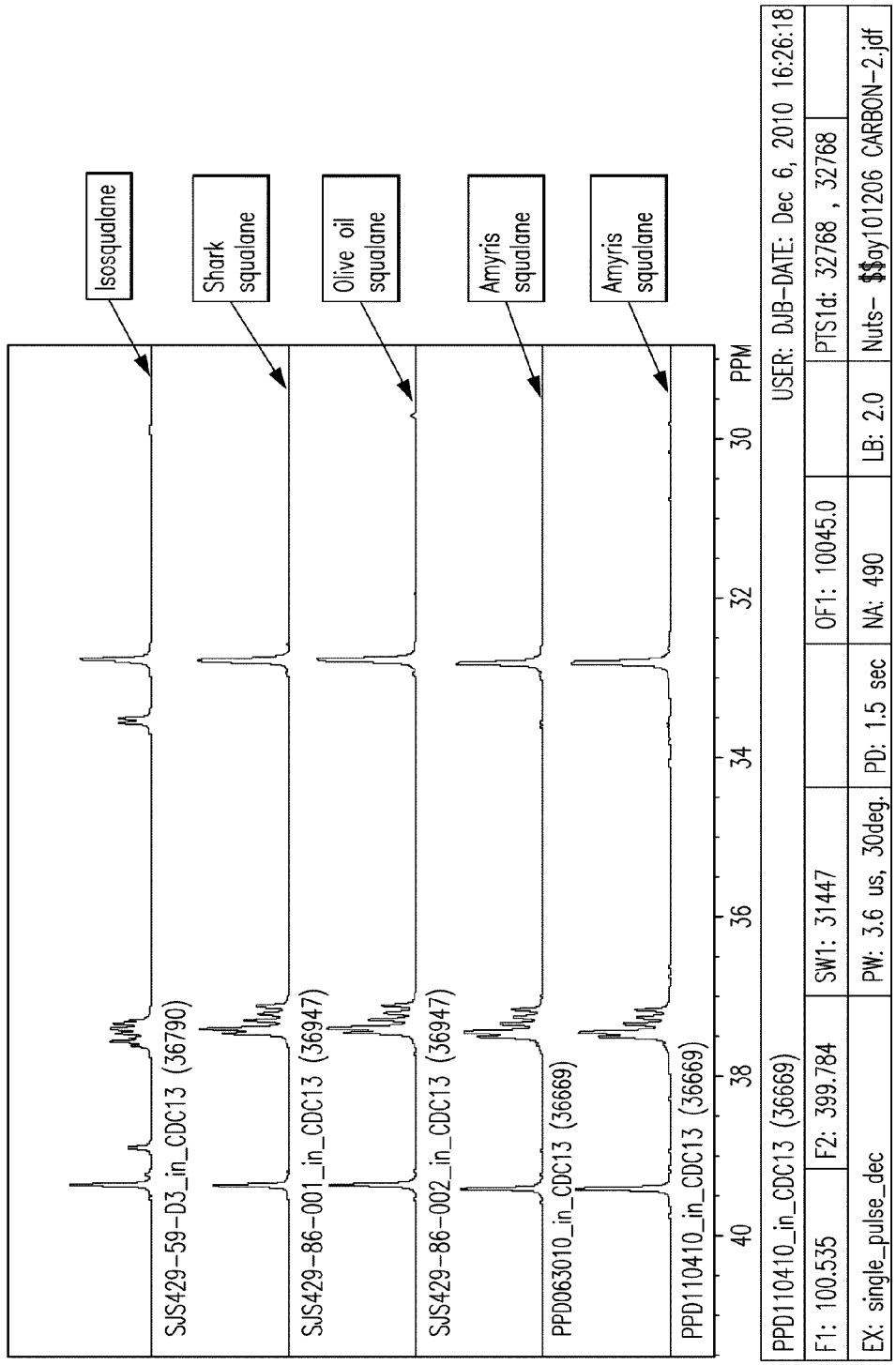
FIG. 11C provides an overlay of $^{13}$C NMR spectra for Examples 20-22 and Comparative Examples 2 and 3 over the region 29 ppm-41 ppm.
Figure 11D:
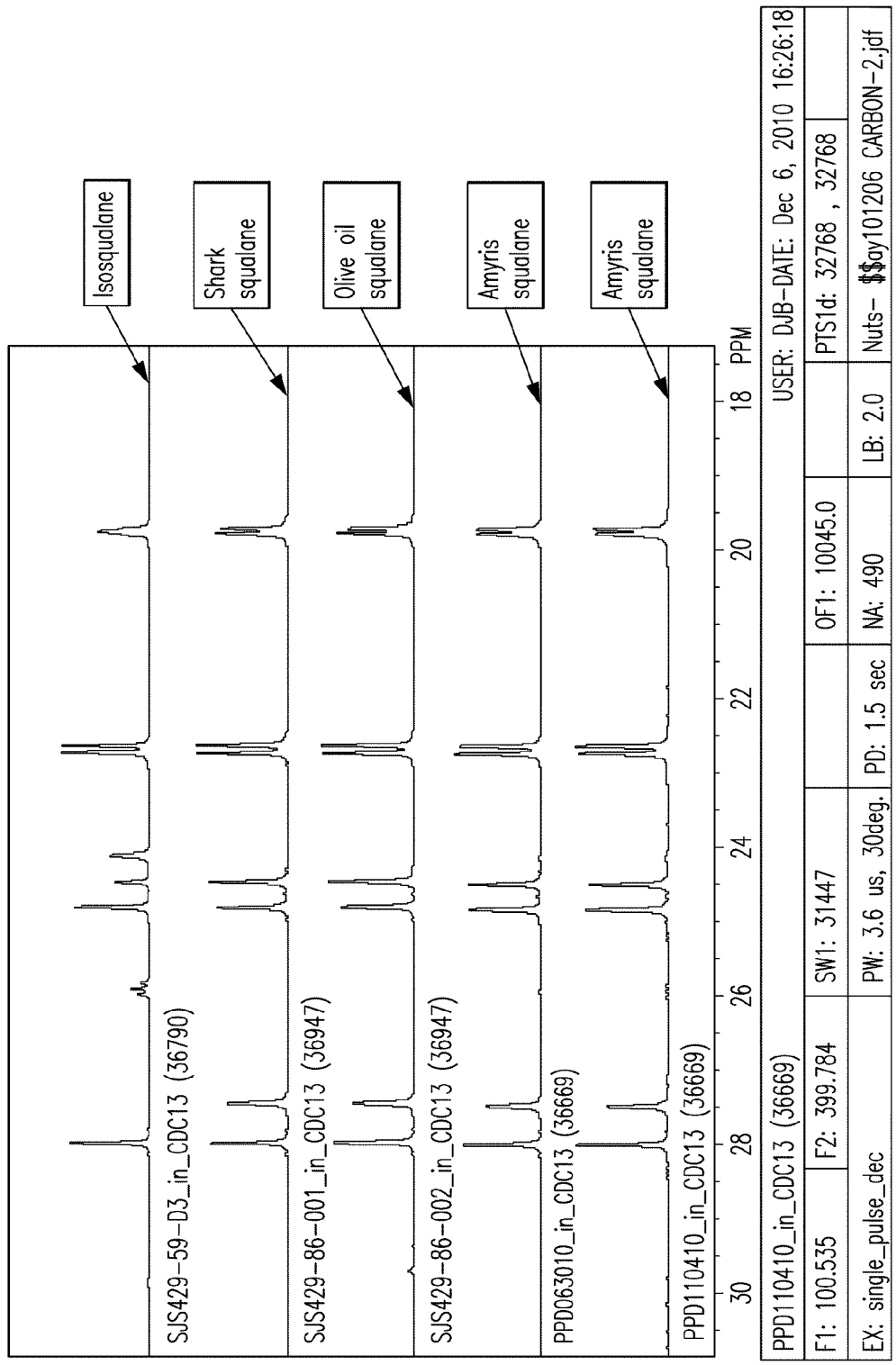
FIG. 11D provides an overlay of $^{13}$C NMR spectra for Examples 20-22 and Comparative Examples 2 and 3 over the region 18 ppm-30 ppm.
Figure 11E:
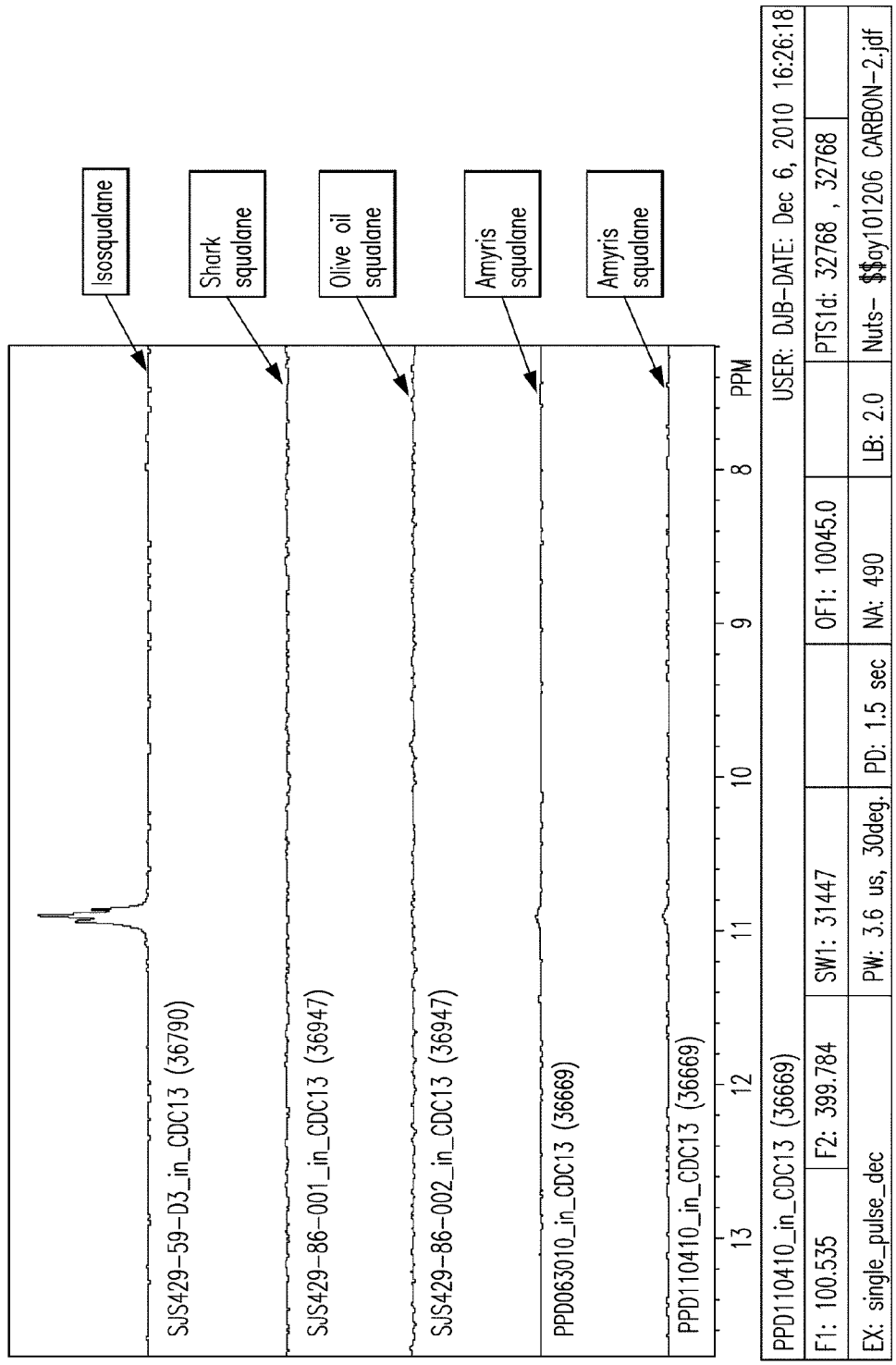
FIGS. 11E-11F provide an overlay of $^{13}$C NMR spectrum Examples 20-22 and for Comparative Examples 2 and 3 over the region 7 ppm-14 ppm.
Figure 11F:
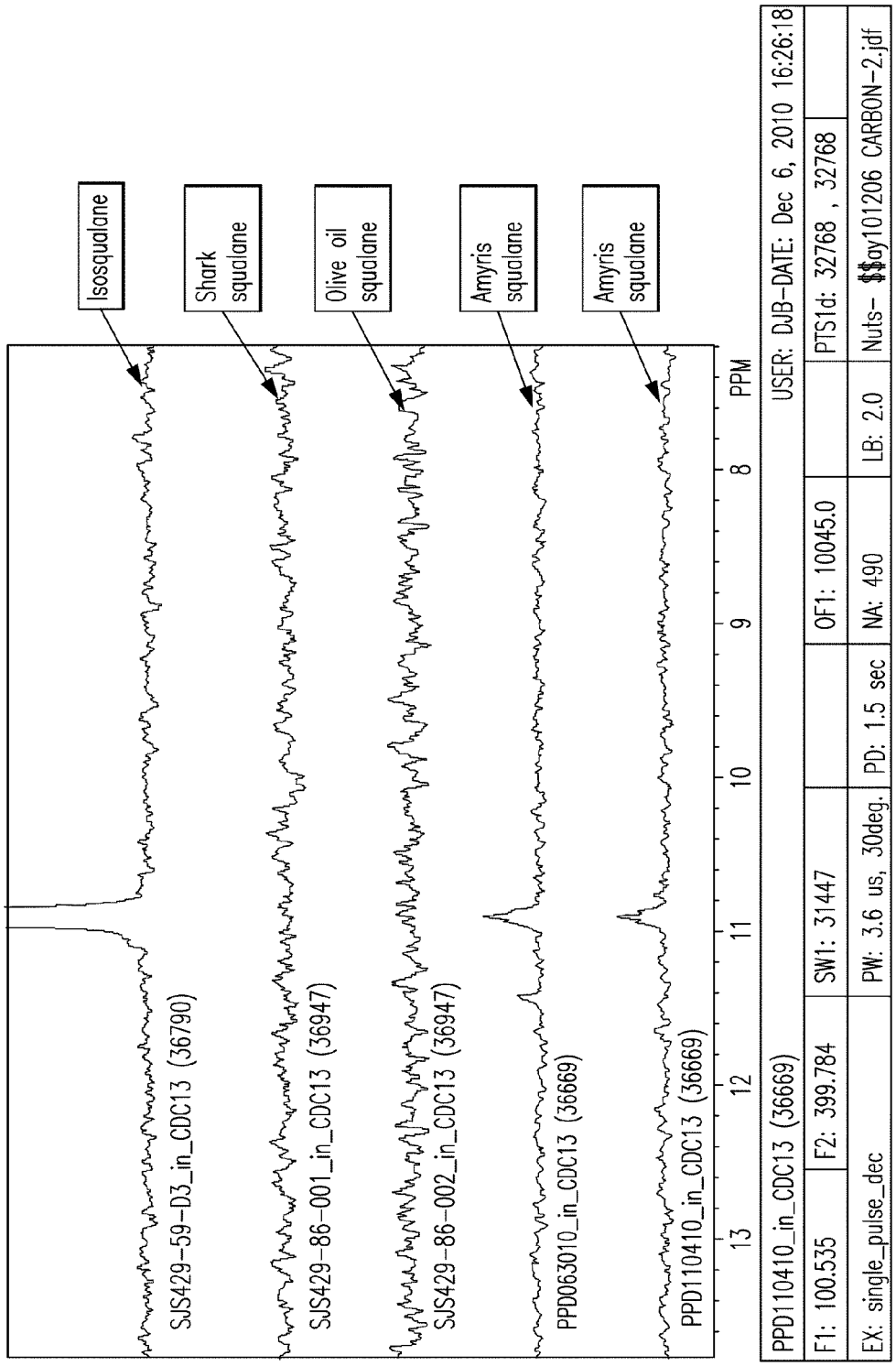
Figure 12:
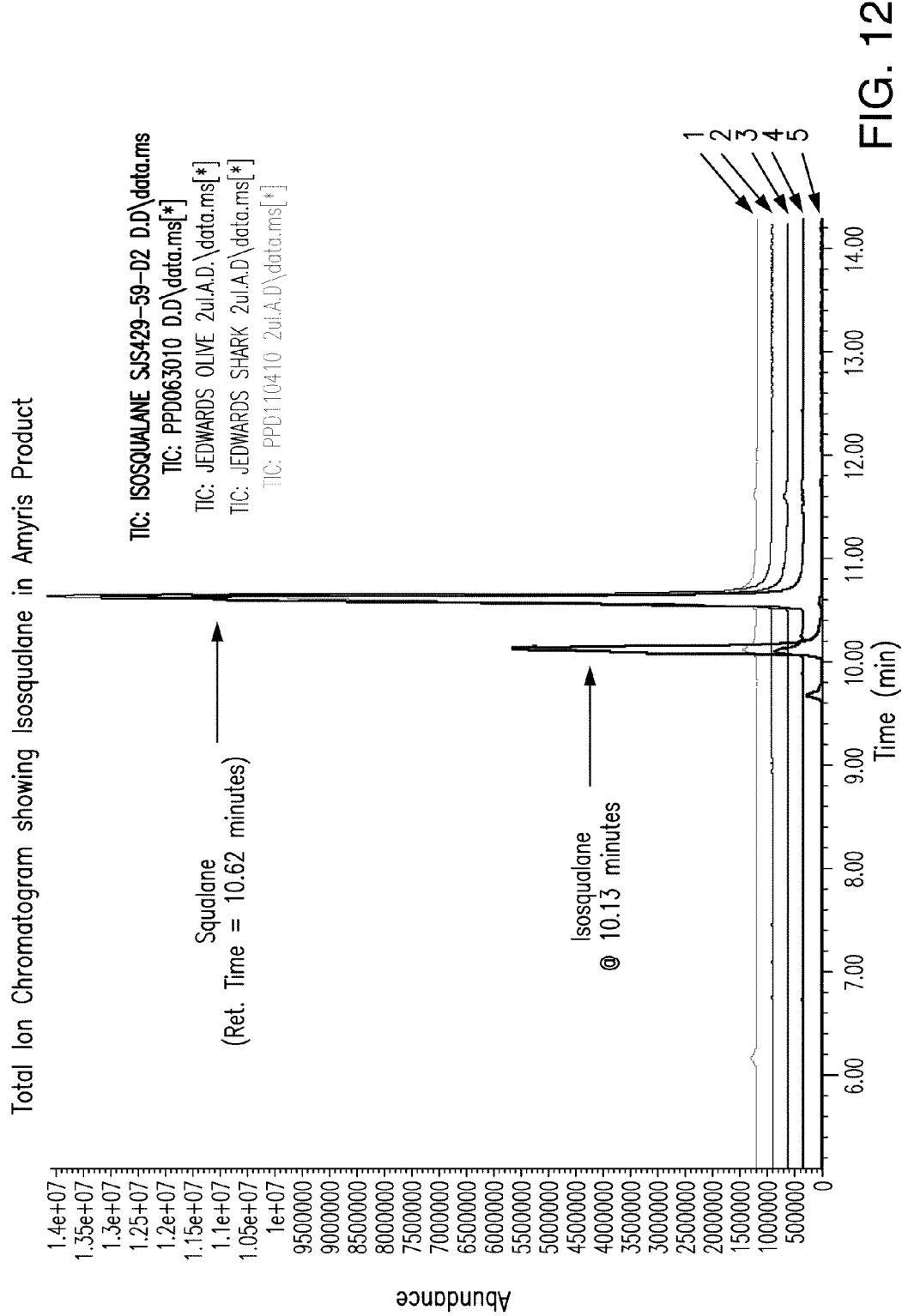
FIG. 12 provides GC-MS spectra for Examples 20-22 and Comparative Examples 2 and 3.

Amyris isosqualane SJS-429-59-D3 has many unique peaks as compared to olive oil and shark squalane. Peaks at 39, 37.5, 33.5, 26, 24 ppm are not seen in shark or olive oil squalane. The peak at 27.5 ppm in shark and olive oil squalane is not present in isosqualane. Amyris isosqualane SJS-429-59-D3 shows a distinct peak at ~11 ppm as shown most clearly in FIGS. 11E-11F; this peak can be assigned to the methyl group on ethyl branch, as shown by the arrow in FIG. 8. As shown in FIGS. 11E-11F, Amyris squalane Lots PPD110410 and PPD0603010 which have purities of 85 wt % and 91 wt %, respectively, each show the presence of the peak at ~11 ppm, which confirms the structural assignment of isosqualane in Amyris squalane product.

The presence of the peak at 11 ppm in Amyris squalane provides conclusive evidence of the presence of isosqualane in Amyris squalane. The absence of this peak in olive oil and shark squalane show that there is no isosqualane detected in these squalane samples.

Figure 13A:
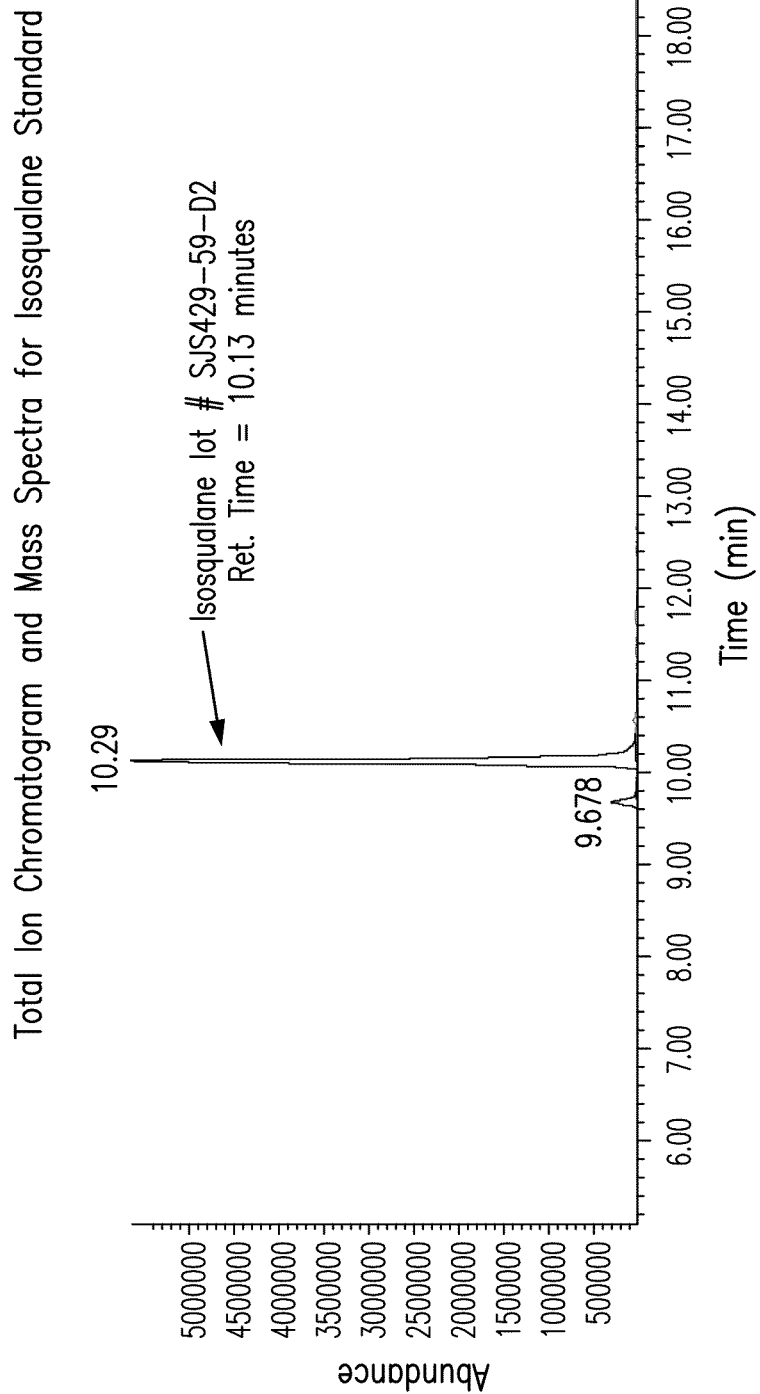
FIGS. 13A-13B provide GC-MS spectra for Example 22 (Isosqualane standard).
Figure 13B:
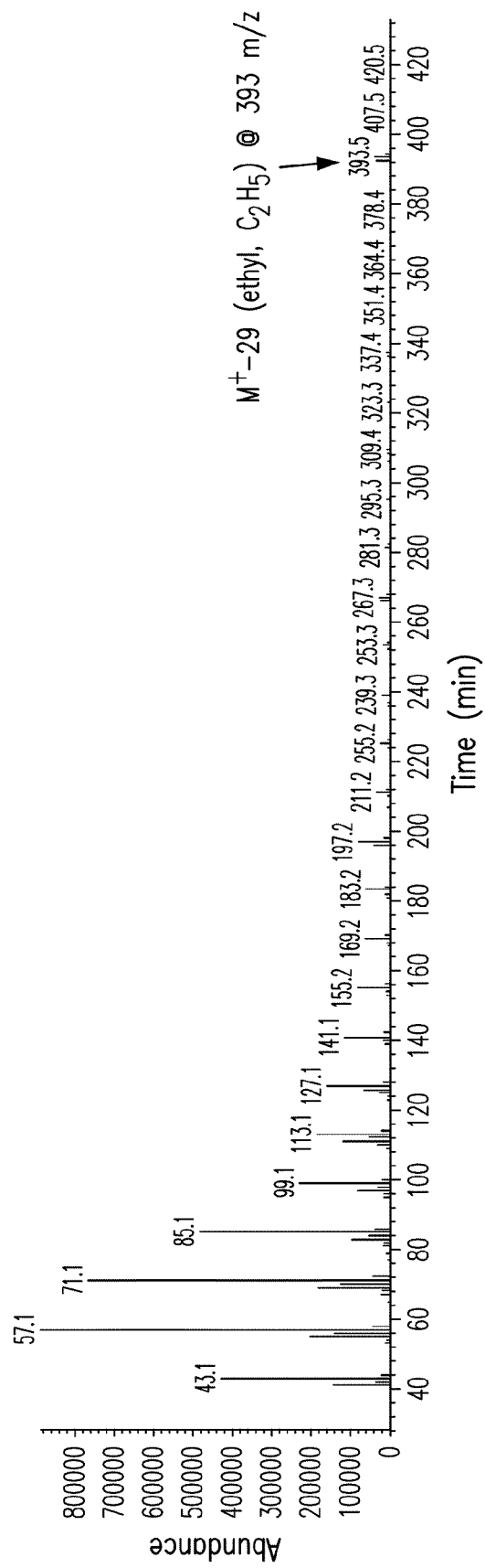
Figure 14A:
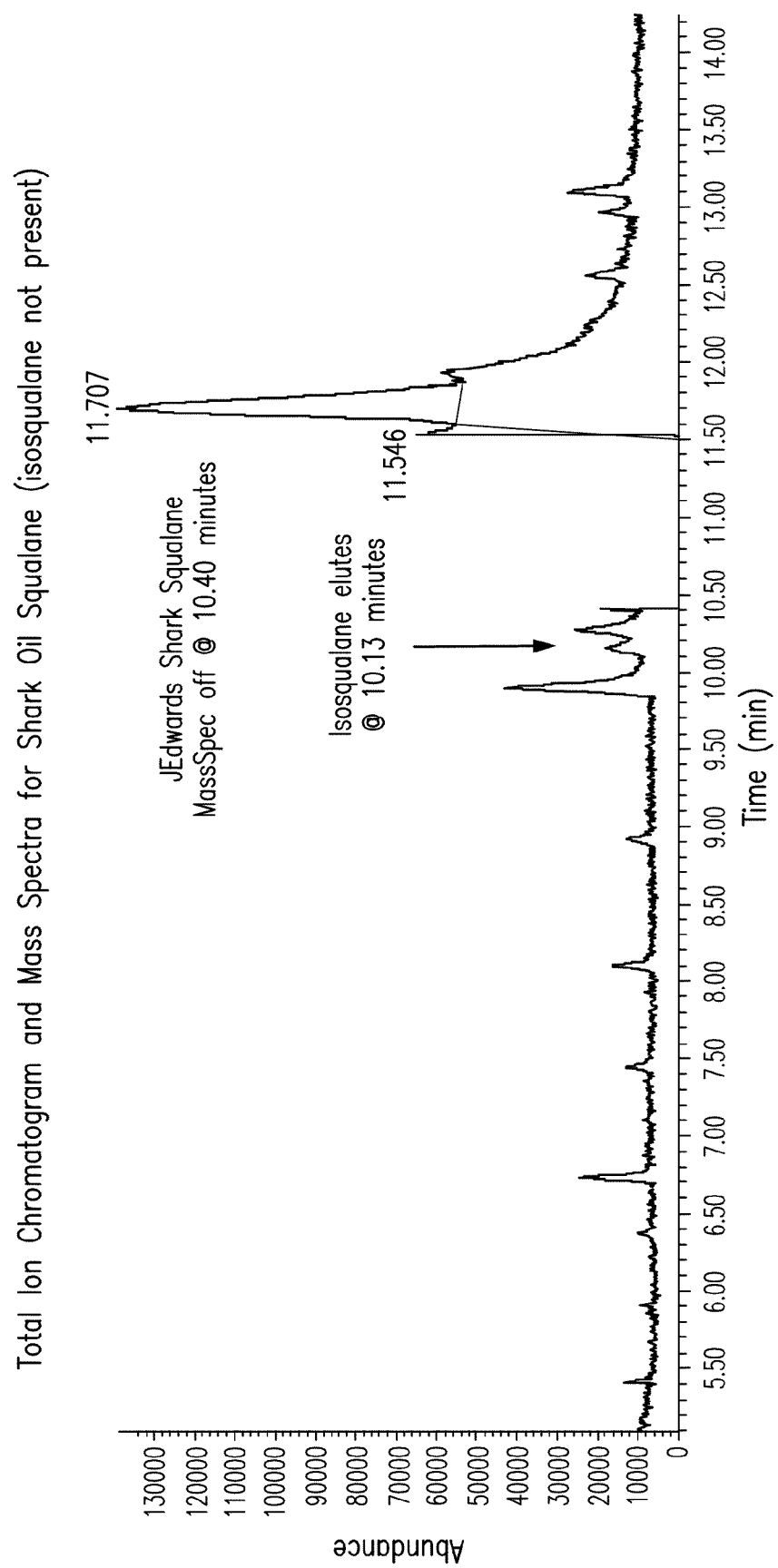
FIGS. 14A-14B provide GC-MS spectra for Comparative Example 2 (shark oil squalane).
Figure 14B:
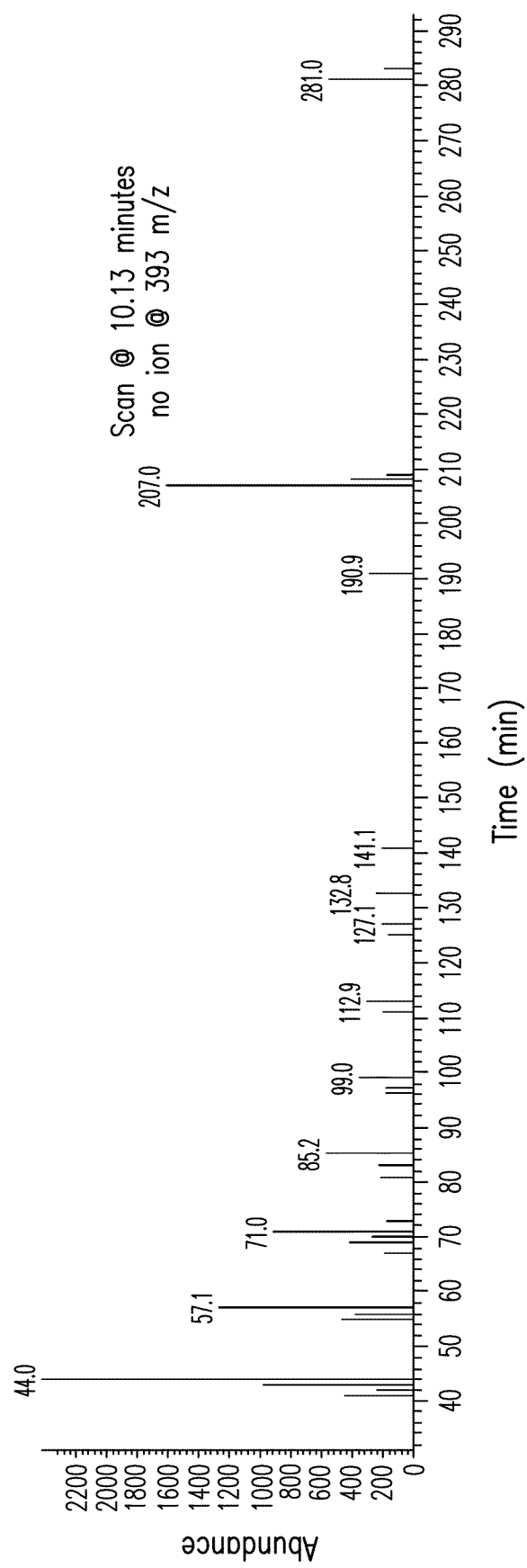
Figure 15A:
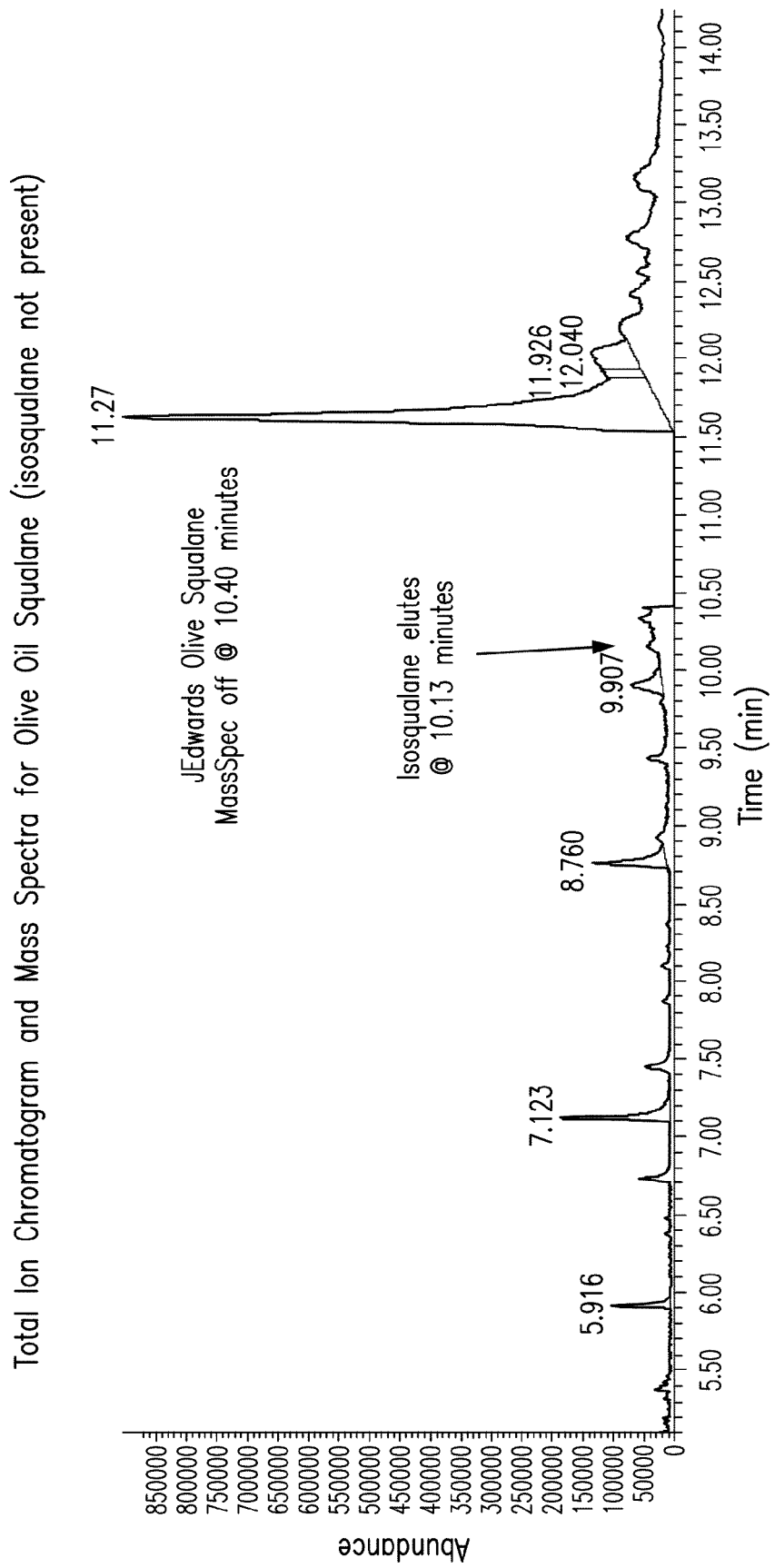
FIGS. 15A-15B provide GC-MS spectra for Comparative Example 3 (olive oil squalane).
Figure 15B:
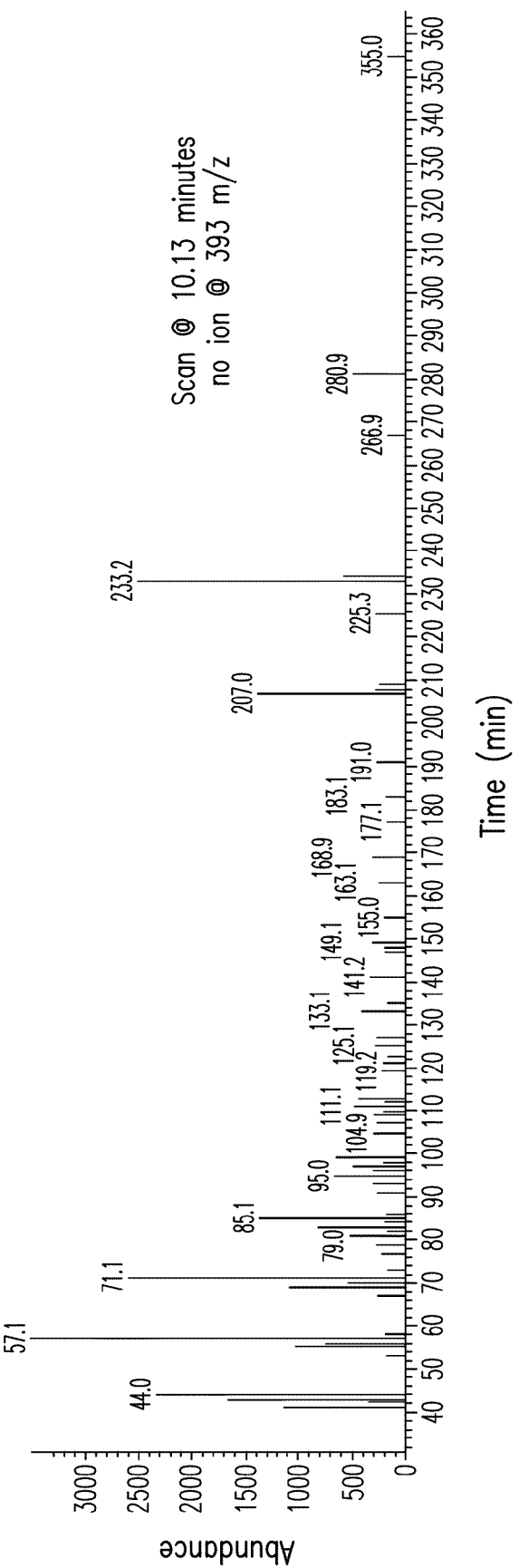
Figure 16A:
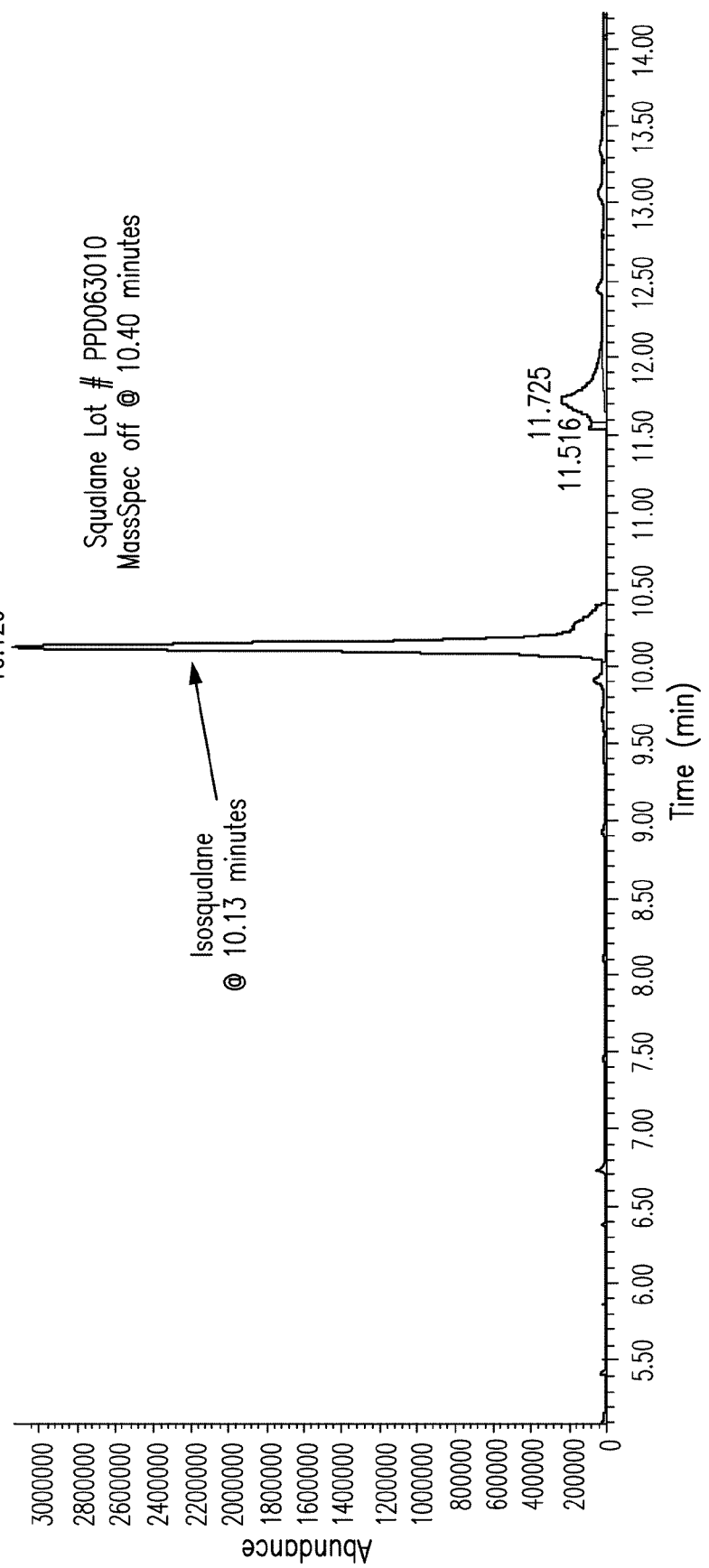
FIGS. 16A-16B provide GC-MS spectra for Example 21, Amyris squalane lot PPD063010.
Figure 16B:
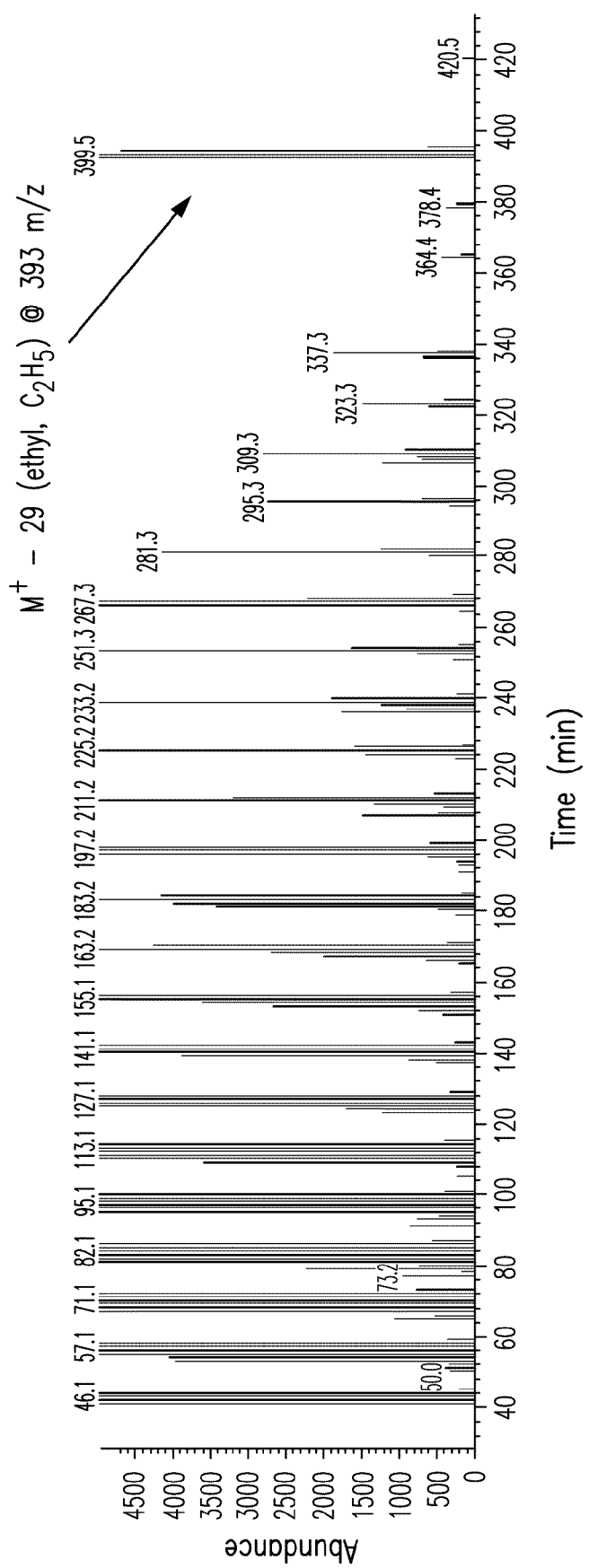
Figure 17A:
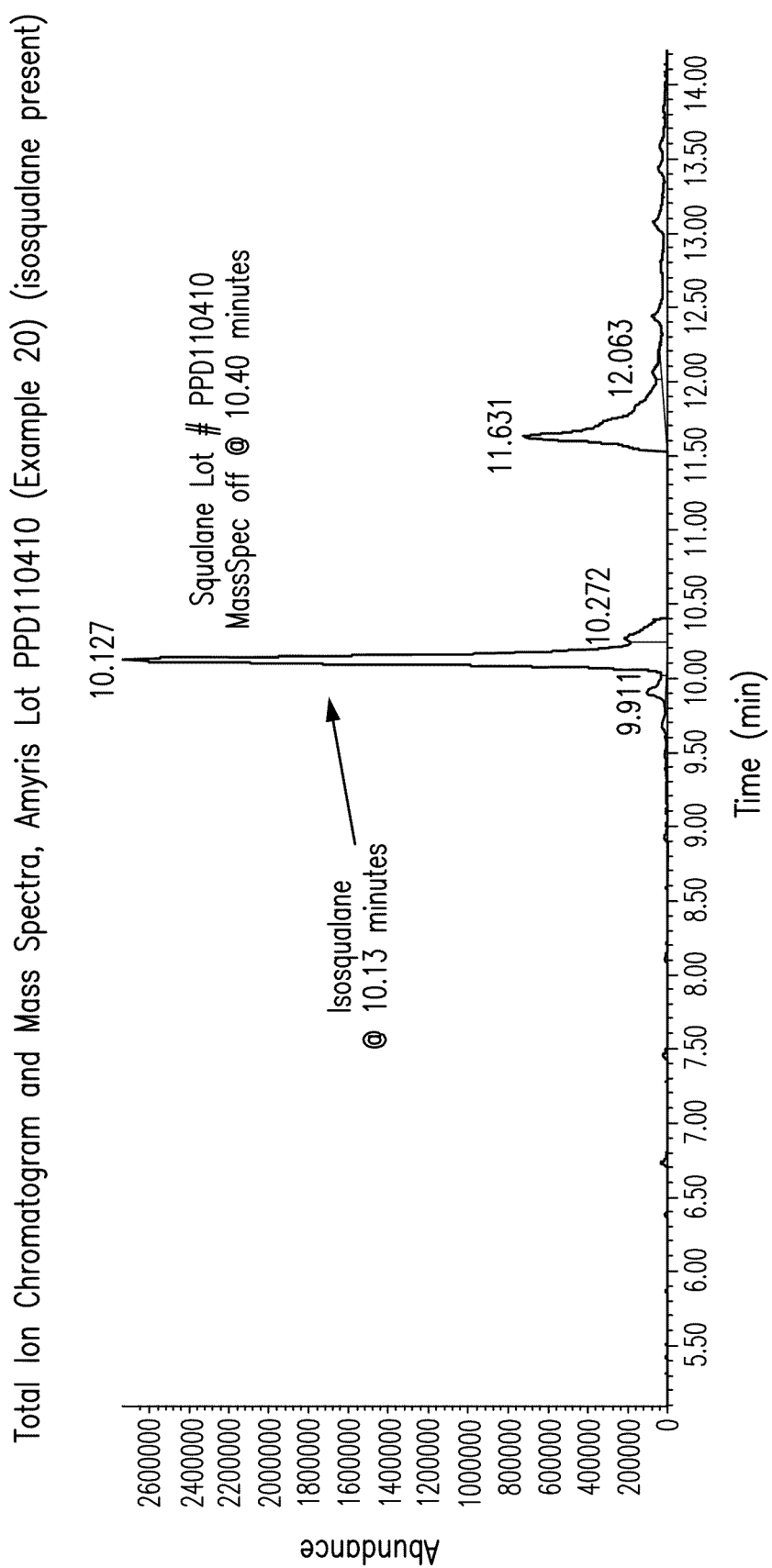
FIGS. 17A-17B provide GC-MS spectra for Example 20, Amyris squalane lot PPD110410.
Figure 17B:
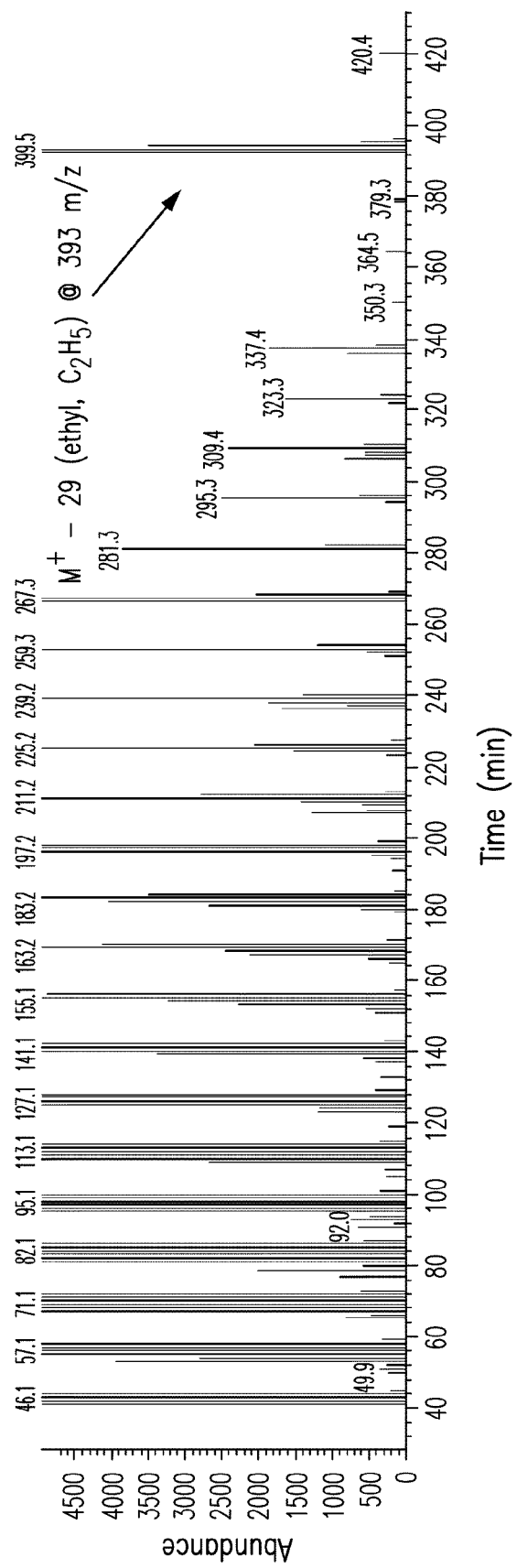

The gas chromatography with mass spectrometry data for Examples 20, 21, 22 and Comparative Examples 2 and 3 are shown in FIGS. 12, 13A, 13B, 14A-14B, 15A-15B, 16A-16B, and 17A-17B. The total ion chromatogram (TIC) traces for Amyris Squalane (Lot PPD063010, Example 21; Lot PPD110410, Example 20), Amyris Isosqualane (SJS-429-59-D2, Example 22) and commercially available squalane (derived from shark oil, Comparative Example 2; and derived from olive oil, Comparative Example 3) are overlaid in FIG. 12. The retention times for squalane are co-incident for all products, however only the Amyris squalane products, Lots PPD110410 and PPD063010 show isosqualane peaks co-incident with the analytical standard of isosqualane SJS-429-59-D2. Isosqualane is present in Amyris squalane Lot PPD063010 (trace 4), and Amyris Lot PPD010410 (trace 1), and in the analytical standard for isosqualane SJS-429-59-D3 (trace 5). Isosqualane is not present in squalane derived from shark oil (trace 2), or in squalane derived from olive oil (trace 3). The total ion chromatogram and mass spectra for the isosqualane standard SJS-429-59-D2 (Example 22) is shown in FIGS. 13A and 13B. As seen in FIGS. 13A and 13B, the characteristic mass spectra is shown for isosqualane analytical standard, which elutes at 10.13 minutes. The total ion chromatogram and mass spectra for shark oil squalane (Comparative Example 2) is shown in FIGS. 14A and 14B. As seen in FIGS. 14A and 14B, the characteristic mass spectra for isosqualane is not present in shark oil squalane at the retention time of 10.13 minutes, where isosqualane would elute if present. The total ion chromatogram and mass spectra for olive oil squalane (Comparative Example 3) is shown in FIGS. 15A and 15B. As seen in FIGS. 15A and 15B, the characteristic mass spectra for isosqualane is not present in shark oil squalane at the retention time of 10.13 minutes, where isosqualane would elute if present. The total ion chromatogram and mass spectra for Amyris squalane lot PPD063010 (Example 21) is shown in FIGS. 16A and 16B. As seen in FIGS. 16A and 16B, the characteristic mass spectra for isosqualane is present in Amyris Squalane Example 21 at the retention time where isosqualane elutes. In FIG. 16B, the spectra are shown on an expanded scale to demonstrate characteristic isotope fragments, for example at m/z=393 for loss of the ethyl group. The total ion chromatogram and mass spectra for Amyris squalane lot PPD110410 (Example 20) is shown in FIGS. 17A and 17B. As seen in FIGS. 17A and 17B, the characteristic mass spectra for isosqualane is present in Amyris Squalane Example 20 at the retention time where isosqualane elutes. In FIG. 17B, the spectra are shown on an expanded scale to demonstrate characteristic isotope fragments, for example at m/z=393 for loss of the ethyl group.

The TIC and mass spectra for the isosqualane analytical standard are shown in FIGS. 13A-13B. Characteristic spectra are obtained at approximately m/z=393. Spectra characteristic of isosqualane are not present in samples of commercially available squalane, when the gas chromatogram traces are scanned at the characteristic retention time for isosqualane. TIC and mass spectra for shark oil squalane are shown in FIGS. 14A-14B, and for olive oil squalane in FIGS. 15A-15B.

The TIC and mass spectra for Amyris squalane consistently show the presence of isosqualane at the characteristic retention time and characteristic m/z fragments. Isosqualane is confirmed for Amyris Lot PPD063010 in FIGS. 16A-16B, and for Amyris Lot PPD110410 in FIGS. 17A-17B.

Data presented from three orthogonal methods of chemical analysis has shown that a unique isomer of squalane is present in Amyris squalane, and not detected in samples of commercially available squalane derived from animal product (shark oil) or derived from plant material (olive oil). Carbon-13 NMR spectra show the presence of a distinct peak at ~11 ppm that confirms structural assignment of a methyl ($-CH_3$) group bonded to an ethyl carbon ($-CH_2-$), consistent with isosqualane in two lots of Amyris product. Gas chromatograms show co-incident retention times for isosqualane analytical standard and for the Amyris product lots, while isosqualane is not detected in the other commercial squalane. Finally, mass spectra show characteristic mass to charge fragments at m/z=393 for isosqualane in the Amyris product lots, which are not detected in the other commercial squalane.

Example 23

Hydraulic Fluid Composition

A lubricant composition suitable for use as a hydraulic fluid was blended using: 811.4 g of Amyris squalane base oil comprising 89% squalane and 4% isosqualane (measured as area %, using GC-FID), 811.6 g SPECTRASYN™ 8 polyalphaolefin (PAO) fluid (available from ExxonMobil Chemical Company, Houston, Tex.), 17.1 g LUBRIZOL 5703 additive (available from Lubrizol, Corp., Wickliffe, Ohio), 210.0 g VISCOPLEX® 8-219 viscosity index improver for hydraulic lubricants (available from Evonik RohMax USA, Inc., Horsham, Pa.), and 7.5 g ESTEREX™ A41 adipate ester synthetic fluid (available from ExxonMobil Chemical Company, Houston, Tex.). The Amyris squalane base oil was prepared according the procedure of Examples 20 and 21, and had a kinematic viscosity at 100° C. of 4.16 cSt. The mixture was heated to 80° C. for 30 minutes, and vortexed using a SCIENTIFIC INDUSTRIES VORTEX GENIE 2 for 1-2 seconds to form the finished lubricant formulation. The resulting lubricant formulation was measured to have a low temperature viscosity at −40° C. of 12440 cPs following ASTM D2983, and a pour point of −54° C. following ASTM D97.

Examples 24a-24 g

Examples of Dimerization of β-farnesene using Pd(acac)$_2$ Precursor

Examples 24a-24 g illustrate additional non-limiting examples in which dimerization of β-farnesene is catalyzed using Palladium (II) acetylacetonate with triphenyl phosphine in isopropanol. These Examples illustrate reactions in which a substrate to catalyst ratio ranging from 400:1 to 2000:1 is used, a ligand:catalyst ratio is varied from 2.0 to 2.8, and the molar concentration (M) of β-farnesene in total solution (volume farnesene+volume isopropanol) is varied from 1M to 3.1M. Some of the results are summarized in Table 21.

Example 24a 0.05 Mol % Pd; Mol Ligand/Mol Pd=2.8; 1.15 M β-Farnesene in Isopropanol Isopropanol used in this reaction was degassed for 30 min by sparging with nitrogen using a gas dispersion tube. Palladium (II) acetylacetonate (0.206 g, 0.67 mmol) and triphenylphosphine (0.496 g, 1.89 mmol) were added to degassed isopropanol (842 ml) in an inerted round bottom flask equipped with reflux condenser, internal thermometer and magnetic stir bar. After stirring under nitrogen for about twenty minutes β-farnesene (276 g, 1.35 mol) was added and the mixture was heated to 85° C. with magnetic stirring under nitrogen. Brief nitrogen sparging steps were also carried out after addition of catalyst/ligand, and farnesene. GC-FID analysis of the reaction mixture after 24 h indicated that residual β-farnesene was 18% of total reaction mixture. Most of the isopropanol was stripped on a rotavap and the residue taken up in 5% ethyl acetate in hexanes and filtered through a pad of silica gel. The solvent was removed in vacuo and the residue taken up in 2× volumes of heptane before hydrogenation in a Parr pressure reactor at 850 psi and 85° C. using 1 wt % of 10 wt % Pd on carbon for 16 hrs. After cooling, the catalyst solution was filtered through Celite and solvent removed in vacuo. GC-FID indicated that squalane was 93.4% of the C-30 fraction (peaks eluting between 14.5- and 17.4 min). The squalane/isosqualane ratio was 20.5:1.

Example 24b 0.25 Mol % Pd; Mol Ligand/Mol Pd=2.8; 1M β-Farnesene in Isopropanol Isopropanol used in this reaction was degassed for 30 min by sparging with nitrogen using a gas dispersion tube. Palladium (II) acetylacetonate (0.894 g, 2.93 mmol) and triphenylphosphine (2.156 g, 8.2 mmol) were added to isopropanol (881 ml) in an inerted round bottom flask equipped with reflux condenser, internal thermometer and magnetic stir bar. After stirring under nitrogen for about twenty minutes β-farnesene (Amyris, Inc., 240 g, 1.174 mol) was added and the mixture was heated to 85° C. with magnetic stirring under nitrogen. Brief nitrogen sparging steps were also carried out after addition of catalyst/ligand, and farnesene. GC-FID analysis of the reaction mixture after 23 h indicated that residual farnesene was less than 1% of total. Carbon Norit (10 g) was added when the solution had cooled to 50° C., and the mixture was stirred at that temperature for 1 hour. The mixture was cooled and filtered through Celite, and the pad was washed with 10 ml isopropanol. The product mixture was hydrogenated in a Parr pressure reactor at 350 psi and 150° C. for 16 h using Pricat Ni 61/15P (catalyst weight was 0.5 wt/wt % of the 1M Fene solution in isopropanol). After cooling, the catalyst solution was filtered through Celite and the isopropanol of the filtrate evaporated to yield a clear liquid. GC-FID indicated that squalane was 93.6% of the C-30 fraction (peaks eluting between 14.5- and 17.4 min). The squalane/isosqualane ratio was 22.4:1.

Example 24(c)

0.12 Mol % Pd; Mol Ligand/Mol Pd=2; 2.3 M β-Farnesene in Isopropanol

Isopropanol used in this reaction was degassed for 30 min by sparging with nitrogen using a gas dispersion tube. Palladium (II) acetylacetonate (0.731 g, 2.4 mmol) and triphenylphosphine (1.259 g, 4.8 mmol) were added to isopropanol (372 ml) in an inerted round bottom flask equipped with reflux condenser, internal thermometer and magnetic stir bar. After stirring under nitrogen for about twenty minutes β-farnesene (408.6 g, 2.0 mol) was added and the mixture was heated to 85° C. with magnetic stirring under nitrogen. Brief nitrogen sparging steps were also carried out after addition of catalyst/ligand, and farnesene. GC-FID analysis of the reaction mixture after 22 h indicated that residual farnesene was 2% of total. Carbon Norit (10 g) was added when the solution had cooled to 50° C., and the mixture was stirred at that temperature for 1 hour. The mixture was cooled and filtered through Celite, and the pad was washed with 10 ml isopropanol. The product mixture was hydrogenated in a Parr pressure reactor at 350 psi and 150° C. for 16 h using Pricat Ni 61/15P (catalyst weight was 1.2 wt/wt % of the 2.3 M β-farnesene solution in isopropanol). After cooling, the catalyst solution was filtered through Celite and the IPA of the filtrate evaporated to yield a clear liquid. GC-FID indicated that squalane was 92.1% of the C-30 fraction (peaks eluting between 14.5- and 17.4 min). The squalane/isosqualane ratio was 20.5:1.

Example 24(d)

0.15 Mol % Pd; Mol Ligand/Mol Pd=2; 1.8 M β-Farnesene in Isopropanol

Isopropanol used in this reaction was degassed for 30 min by sparging with nitrogen using a gas dispersion tube. Palladium (II) acetylacetonate (0.914 g, 3 mmol) and triphenylphosphine (1.574 g, 6 mmol) were added to isopropanol (624 ml) in an inerted round bottom flask equipped with reflux condenser, internal thermometer and magnetic stir bar. After stirring under nitrogen for about twenty minutes β-farnesene (408.6 g, 2.0 mol) was added and the mixture was heated to 85° C. with magnetic stirring under nitrogen. Brief nitrogen sparging steps were also carried out after addition of catalyst/ligand, and farnesene. GC-FID analysis of the reaction mixture after 14 h indicated that residual farnesene was less than 1% of total. Carbon Norit (10 g) was added when the solution had cooled to 50° C., and the mixture was stirred at that temperature for 1 hour. The mixture was cooled and filtered through Celite, and the pad was washed with 10 ml IPA. The product mixture was hydrogenated in a Parr pressure reactor at 350 psi and 150° C. for 16 h using Pricat Ni 61/15P (catalyst weight was 0.9 wt/wt % of the 1.8 M farnesene solution in isopropanol). After cooling, the catalyst solution was filtered through Celite and the isopropanol of the filtrate evaporated to yield a clear liquid. GC-FID indicated that squalane was 93.5% of the C-30 fraction (peaks eluting between 14.5- and 17.4 min). The squalane/isosqualane ratio was 21.6:1.

Example 24(e)

0.075 Mol % Pd; Mol Ligand/Mol Pd=2.8; 2.5 M β-Farnesene in Isopropanol

Isopropanol used in this reaction was degassed for 30 min by sparging with nitrogen using a gas dispersion tube. Palladium (II) acetylacetonate (0.457 g, 1.5 mmol) and triphenylphosphine (1.102 g, 4.2 mmol) were added to isopropanol (624 ml) in an inerted rbf equipped with reflux condenser, internal thermometer and magnetic stir bar. After stirring under nitrogen for about twenty minutes farnesene (408.6 g, 2.0 mol) was added and the mixture was heated to 85° C. with magnetic stirring under nitrogen. Brief nitrogen sparging steps were also carried out after addition of catalyst/ligand, and farnesene. GC-FID analysis of the reaction mixture after 56 h indicated that residual farnesene was 4% of total. Carbon Norit (10 g) was added when the solution had cooled to 50° C., and the mixture was stirred at that temperature for 1 hour. The mixture was cooled and filtered through Celite, and the pad was washed with 10 ml IPA. The product mixture was hydrogenated in a Parr pressure reactor at 350 psi and 150° C. for 16 h using Pricat Ni 61/15P (catalyst weight was 1.25 wt/wt % of the 2.5 M β-farnesene solution in isopropanol). After cooling, the catalyst solution was filtered through Celite and the isopropanol of the filtrate evaporated to yield a clear liquid. GC-FID indicated that squalane was 90.8% of the C-30 fraction (peaks eluting between 14.5- and 17.4 min). The squalane/isosqualane ratio was 19.5:1.

Example 24f 0.12 Mol % Pd; Mol Ligand/Mol Pd=2.0; 3.1M β-farnesene in Isopropanol Isopropanol used in this reaction was degassed for 30 min by sparging with nitrogen using a gas dispersion tube. Palladium (II) acetylacetonate (0.731 g, 2.4 mmol) and triphenylphosphine (1.259 g, 4.8 mmol) were added to isopropanol (149 ml) in an inerted round bottom flask equipped with reflux condenser, internal thermometer and magnetic stir bar. After stirring under nitrogen for about twenty minutes, β-farnesene (408.6 g, 2.0 mol) was added and the mixture was heated to 85° C. with magnetic stirring under nitrogen. Brief nitrogen sparging steps were also carried out after addition of catalyst/ligand, and β-farnesene. GC-FID analysis of the reaction mixture after 16 h indicated that residual β-farnesene was less than 3% of total reaction mixture. Carbon Norit (10 g) was added when the solution had cooled to 50° C., and the mixture was stirred at that temperature for 1 hour. The mixture was cooled and filtered through Celite, and the pad was washed with 10 ml isopropanol. The product mixture was hydrogenated in a Parr pressure reactor at 350 psi and 150° C. using Pricat Ni 61/15P (catalyst weight was 1.5 wt/wt % of the ~3 M β-farnesene solution in isopropanol). After cooling, the catalyst solution was filtered through Celite and the isopropanol of the filtrate evaporated to yield a clear liquid (419 g). GC-FID indicated that squalane was 86.2% of the total, and 93.5% of the C-30 fraction (peaks eluting between 14.5- and 17.4 min). The squalane/isosqualane ratio was 23.2:1. Distillation via Kugelrohr gave three fractions: 1) C-15 fraction (monomers) distilled at 160° C. and 0.1 torr; 2) C-30 (dimers) at 230° and 0.1 torr and 3) C-45 (trimers) remained undistilled. The C-30 fraction contained 367 g (87% yield) of a colorless oil.

Example 24(g)

0.1 Mol % Pd; Mol Ligand/Mol Pd=2.8; 3.1M β-Farnesene in Isopropanol

Isopropanol used in this reaction was degassed for 30 min by sparging with nitrogen using a gas dispersion tube. Palladium (II) acetylacetonate (0.610 g, 2 mmol) and triphenylphosphine (1.469 g, 5.6 mmol) were added to isopropanol (624 ml) in an inerted rbf equipped with reflux condenser, internal thermometer and magnetic stir bar. After stirring under nitrogen for about twenty minutes farnesene (408.6 g, 2.0 mol) was added and the mixture was heated to 85° C. with magnetic stirring under nitrogen. Brief nitrogen sparging steps were also carried out after addition of catalyst/ligand, and β-farnesene. GC-FID analysis of the reaction mixture after 33 h indicated that residual farnesene was 2% of total. Carbon Norit (10 g) was added when the solution had cooled to 50° C., and the mixture was stirred at that temperature for 1 hour. The mixture was cooled and filtered through Celite, and the pad was washed with 10 ml isopropanol. The product mixture was hydrogenated in a Parr pressure reactor at 350 psi and 150° C. for 16 h using Pricat Ni 61/15P (catalyst weight was 1.55 wt/wt % of the 3.1 M farnesene solution in isopropanol). After cooling, the catalyst solution was filtered through Celite and the isopropanol of the filtrate evaporated to yield a clear liquid. GC-FID indicated that squalane was 92.6% of the C-30 fraction (peaks eluting between 14.5- and 17.4 min). The squalane/isosqualane ratio was 21.8:1.

TABLE 21

Summary of results for Examples 24a-24g.

| Example | Pd mol % | TPP mol % | Mol ligand/ mol Pd | Isopropanol (IPA) (ml) | M β-farnesene in IPA | Squalane: isosqualane |
|---|---|---|---|---|---|---|
| 24a | 0.05 | 0.14 | 2.8 | 842 | 1.15 | 20.5:1 |
| 24b | 0.25 | 0.70 | 2.8 | 881 | 1 | 22.4:1 |
| 24c | 0.12 | 0.24 | 2.0 | 372 | 2.3 | 20.5:1 |
| 24d | 0.15 | 0.30 | 2.0 | 624 | 1.8 | 21.6:1 |
| 24e | 0.075 | 0.21 | 2.8 | 298 | 2.5 | 19.5:1 |
| 24f | 0.12 | 0.24 | 2.0 | 149 | 3.1 | 23.2:1 |
| 24g | 0.10 | 0.28 | 2.8 | 149 | 3.1 | 21.8:1 |

All publications and patent applications mentioned in this specification are herein incorporated by reference to the same extent as if each individual publication or patent application was specifically and individually indicated to be incorporated by reference. Although the foregoing has been described in some detail by way of illustration and example for purposes of clarity of understanding, it will be readily apparent to those of ordinary skill in the art in light of the teachings herein that certain changes and modifications may be made thereto without departing from the spirit or scope of the appended claims.

What is claimed is:

1. A composition comprising isosqualane and neosqualane.

2. A composition comprising squalane and isosqualane, wherein the composition has a ratio of (quantity squalane):(quantity isosqualane) in a range from about 1:60 to about 14:1.

3. The composition of claim 2, wherein the ratio (quantity squalane):(quantity isosqualane) represents (mass squalane):(mass isosqualane).

4. The composition of claim 2, wherein the ratio (quantity squalane):(quantity isosqualane) represents (area squalane):(area isosqualane), and (area squalane) and (area isosqualane) are each peak areas measured by gas chromatography.

5. The composition of claim 2, wherein the composition is prepared according to a method comprising:
   A) contacting β-farnesene with
      i) a palladium carbene in the presence of a base in a protic solvent, or
      ii) a zirconium catalyst; and
   B) hydrogenating the product of step (A).

6. The composition of claim 2, wherein the ratio (quantity squalane):(quantity isosqualane) is in a range from about 1:60 to about 1:7.

7. The composition of claim 6, further comprising neosqualane.

8. The composition of claim 2, wherein the ratio (quantity squalane):(quantity isosqualane) is in a range from about 1:1 to about 10:1.

9. A lubricant base oil comprising the composition of claim 2.

10. A lubricant composition comprising at least about 20 wt. % of the lubricant base oil of claim 9.

11. A lubricant formulation comprising the lubricant base oil of claim 9, and further comprising an additive selected from the group consisting of a rust inhibitor, a viscosity modifier, an antioxidant, a flame retardant, an antiwear agent, a pour point modifier, a dispersant, a seal swell agent, a corrosion inhibitor, a demulsifier, a dispersant, a solubilizer, and any combination of two or more thereof.

12. The lubricant formulation of claim 11, adapted for use as a hydraulic fluid.

13. A machine comprising the lubricant formulation of claim 11, wherein the lubricant formulation lubricates a component of the machine.

14. A composition comprising squalane and isosqualane, wherein an amount of squalane in the composition is about 5 wt % or greater and an amount of isosqualane in the composition is about 10 wt % or greater.

15. The composition of claim 14, wherein the amount of squalane is about 50 wt % or greater.

16. The composition of claim 14, wherein the amount of squalane is about 80 wt % or greater.

* * * * *